(12) United States Patent
Samsoondar

(10) Patent No.: US 9,470,673 B2
(45) Date of Patent: Oct. 18, 2016

(54) JOINT SPECTROSCOPIC AND BIOSENSOR SYSTEM FOR POINT-OF-CARE TESTING

(71) Applicant: ChroMedX Corp., Toronto (CA)

(72) Inventor: James Samsoondar, Markham (CA)

(73) Assignee: CHROMEDX CORP., Toronto, Ontario (CA)

(*) Notice: Subject to any disclaimer, the term of this patent is extended or adjusted under 35 U.S.C. 154(b) by 0 days.

(21) Appl. No.: 15/144,073

(22) Filed: May 2, 2016

(65) Prior Publication Data
US 2016/0245793 A1  Aug. 25, 2016

Related U.S. Application Data

(63) Continuation of application No. PCT/CA2015/050455, filed on May 20, 2015.

(60) Provisional application No. 62/114,700, filed on Feb. 11, 2015, provisional application No. 62/006,066, filed on May 31, 2014.

(51) Int. Cl.
*G01N 33/49* (2006.01)
*B01L 3/00* (2006.01)

(52) U.S. Cl.
CPC .............. *G01N 33/49* (2013.01); *B01L 3/502* (2013.01); *B01L 3/561* (2013.01); *B01L 2200/10* (2013.01); *B01L 2300/04* (2013.01); *B01L 2300/0636* (2013.01)

(58) Field of Classification Search
CPC ............. G01N 33/49; G01N 33/5011; G01N 33/5008; G01N 15/05; G01N 15/1434; B01L 3/00; A61B 5/14532; A61B 5/1455; C12Q 1/04; C12Q 1/02; C12Q 1/18
See application file for complete search history.

(56) References Cited

U.S. PATENT DOCUMENTS

| | | | |
|---|---|---|---|
| 5,096,669 A | 3/1992 | Lauks et al. | |
| 7,740,804 B2 | 6/2010 | Samsoondar | |
| 2005/0197596 A1* | 9/2005 | Bellucci | A61B 5/1427 600/573 |
| 2006/0228259 A1 | 10/2006 | Samsoondar | |

OTHER PUBLICATIONS

Office Action from corresponding CA Patent Application No. 2,911,318 dated Jan. 15, 2016.
Written Opinion of the International Searching Authority for PCT/CA2015/050455.

* cited by examiner

*Primary Examiner* — Abdullahi Nur

(57) ABSTRACT

Some embodiments of the invention provide a system for measurement of at least two hemoglobin species in a patient's blood sample by spectroscopy, and measurement of at least pH of the blood sample by biosensor. The system comprises a disposable cartridge adapted for insertion into a slot of an analyzer, and the results are used to monitor the acid-base status of a patient. A method for monitoring the acid-base status of a patient using the system is also provided.

21 Claims, 21 Drawing Sheets

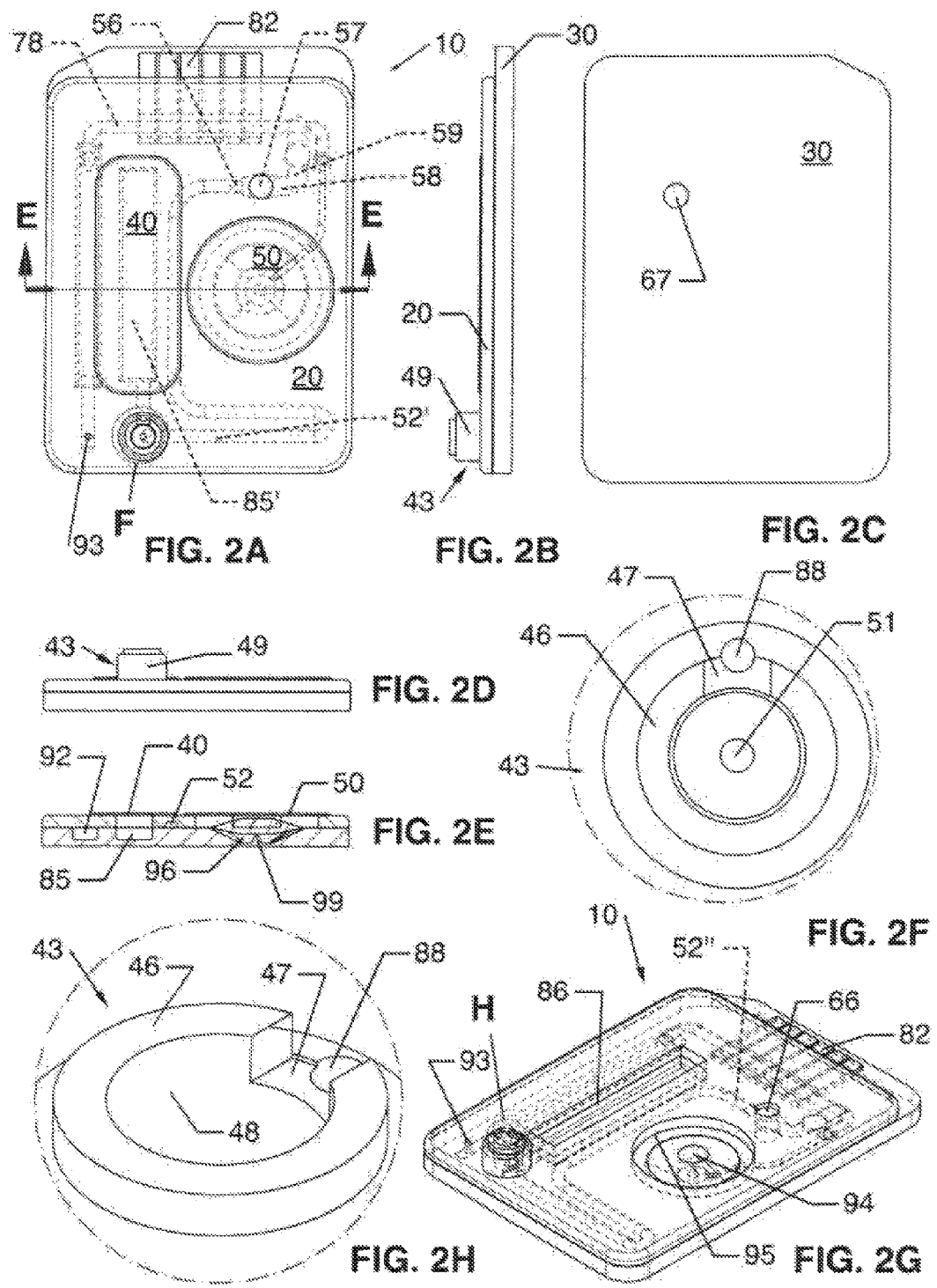

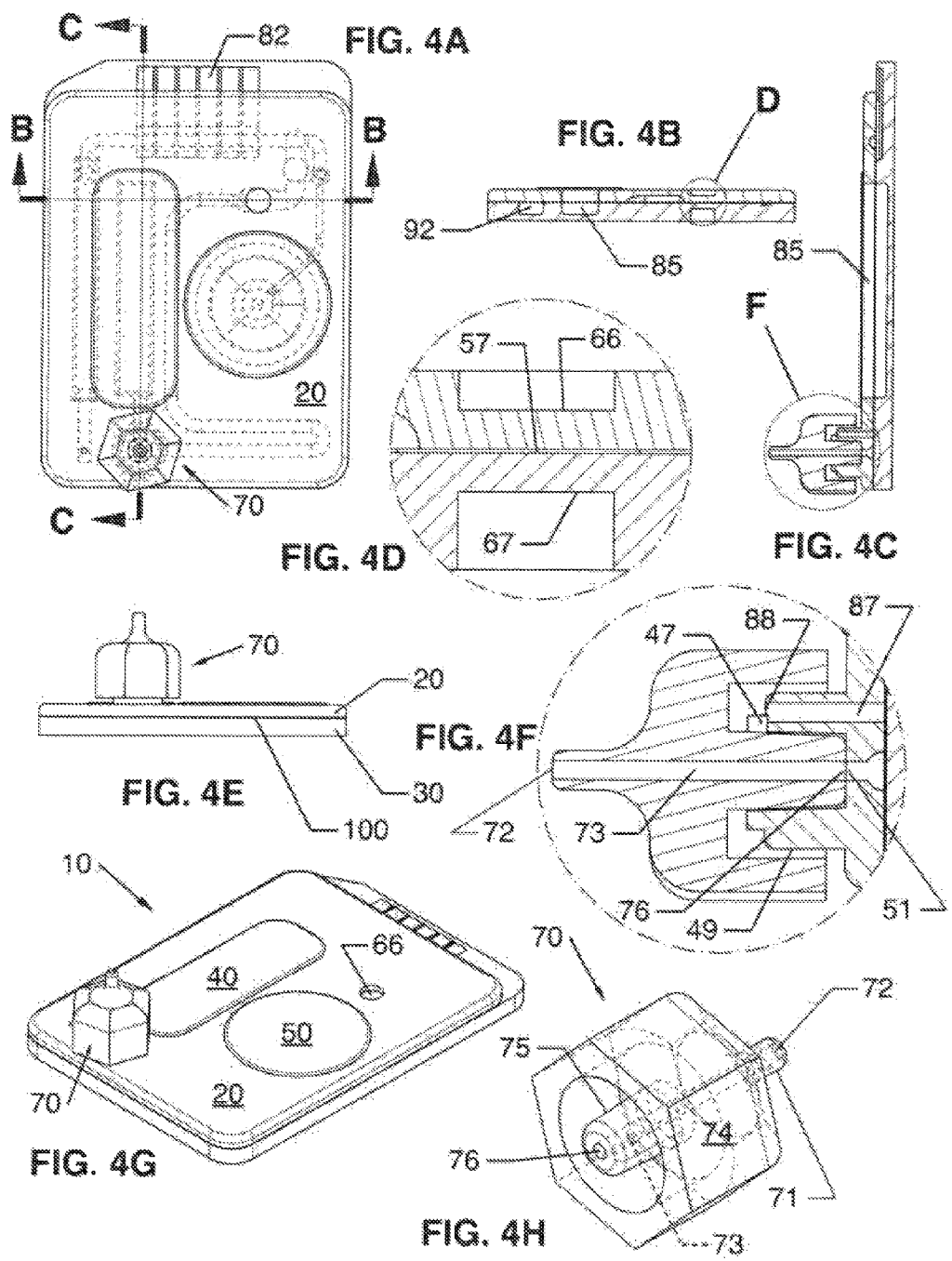

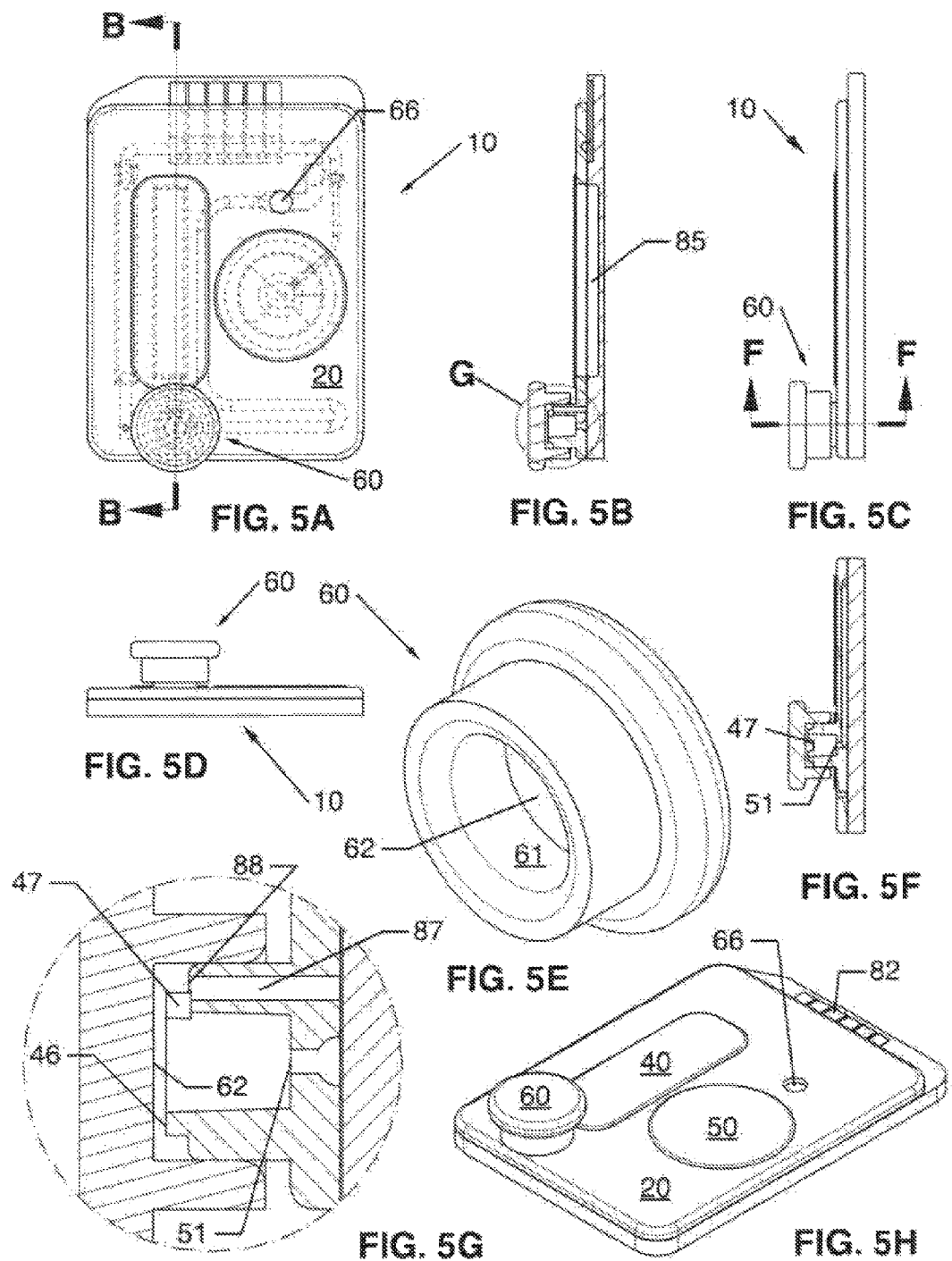

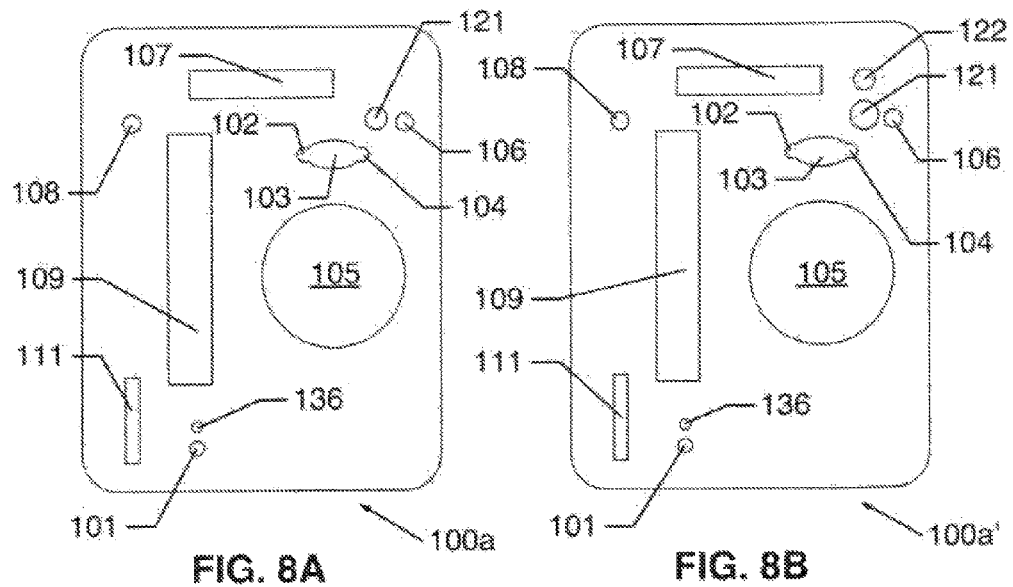
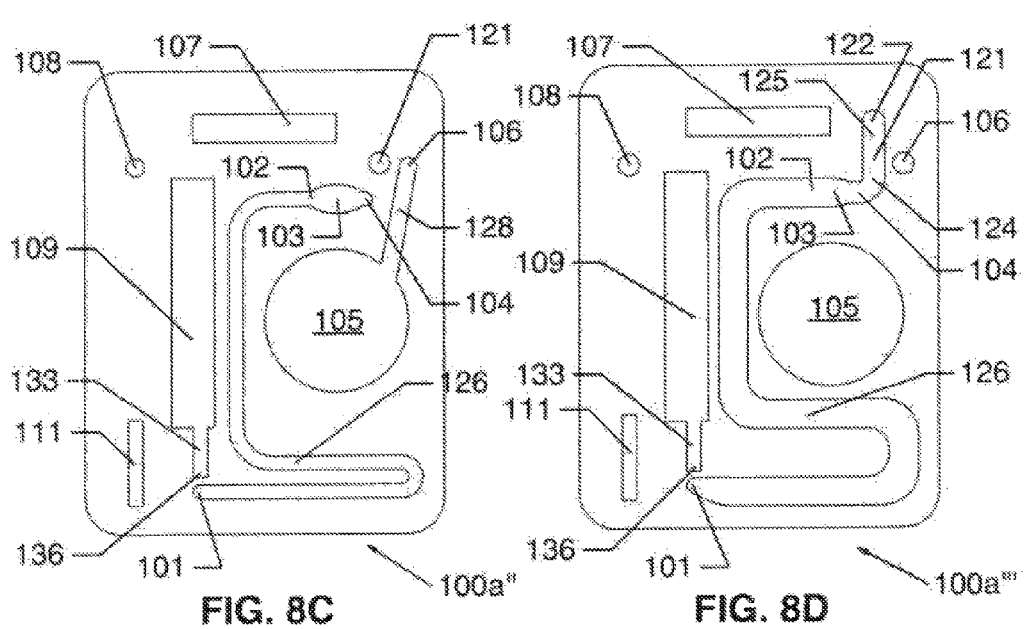

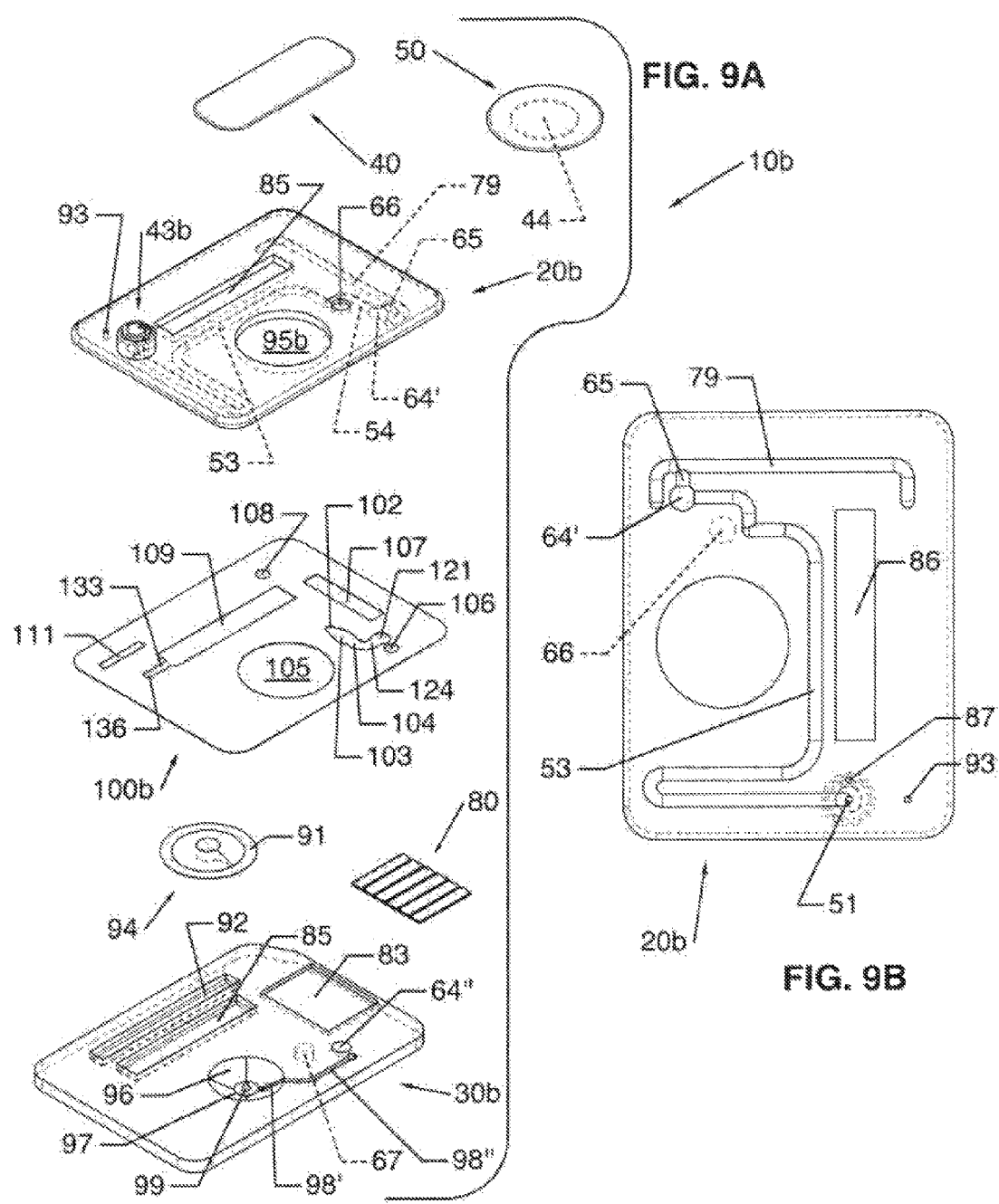

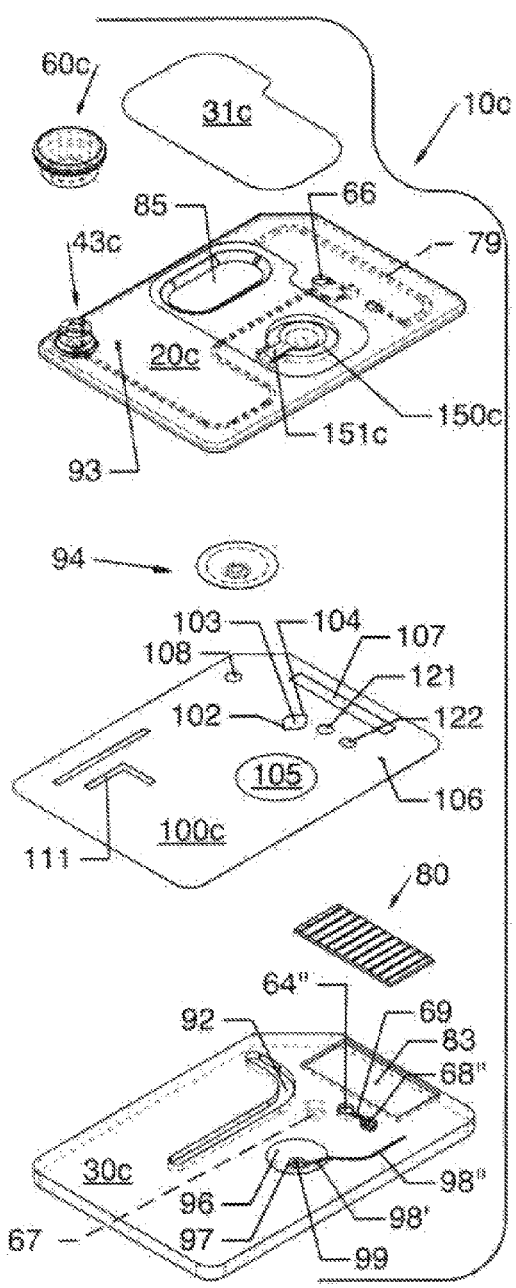
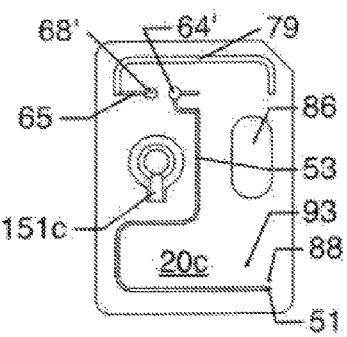
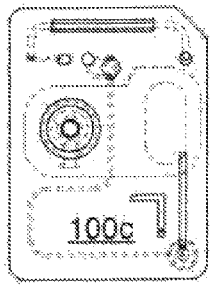
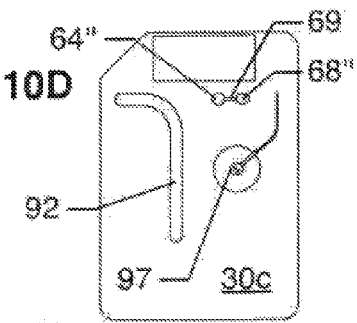
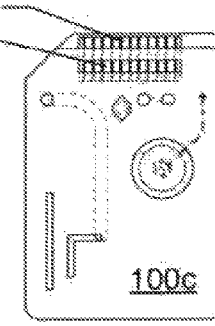

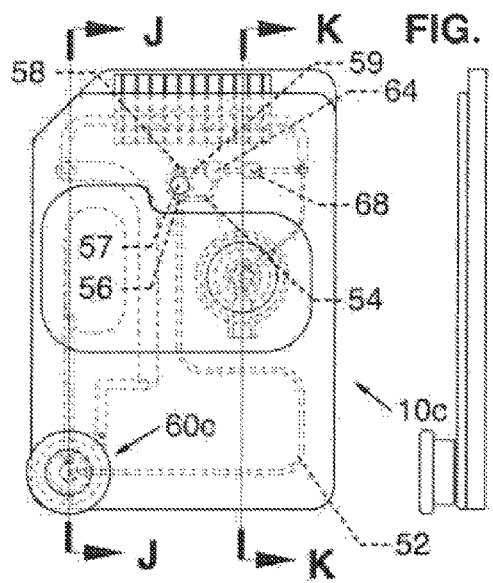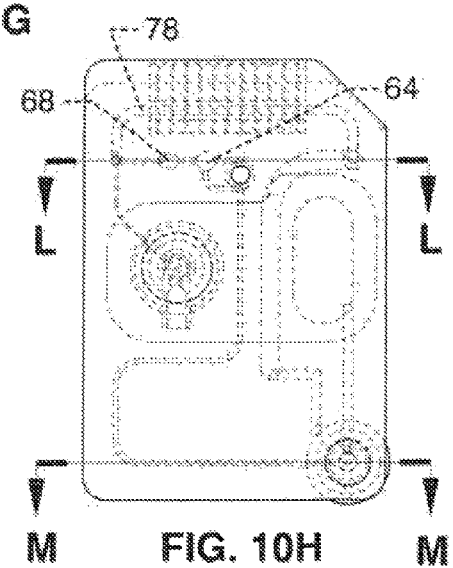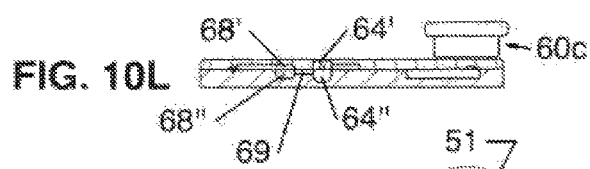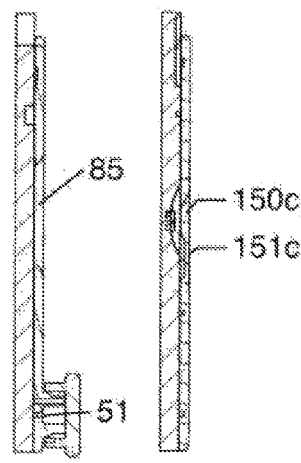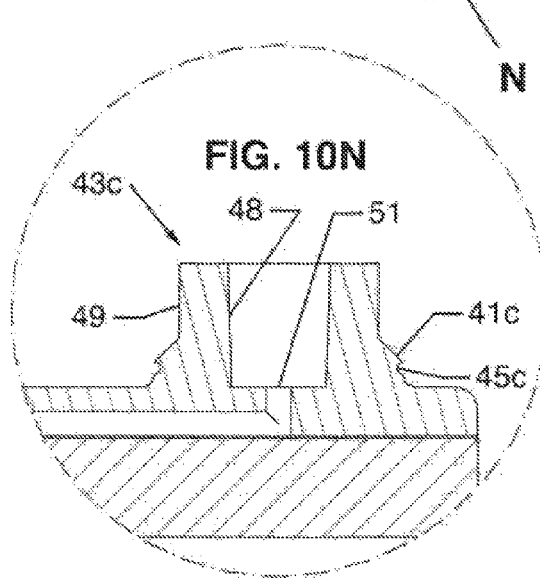
FIG. 10F
FIG. 10G
FIG. 10H
FIG. 10L
FIG. 10M
FIG. 10J  FIG. 10K
FIG. 10N

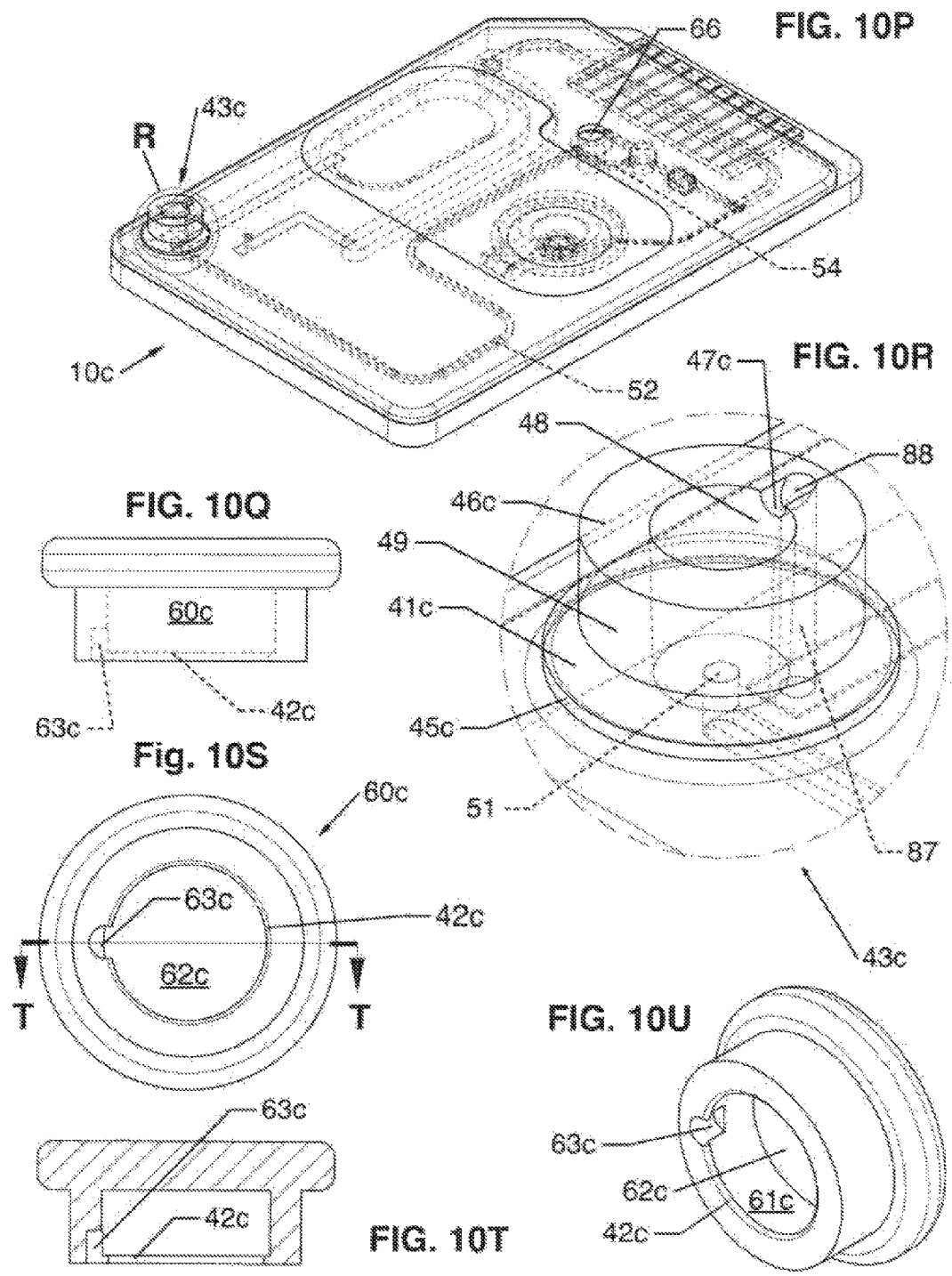

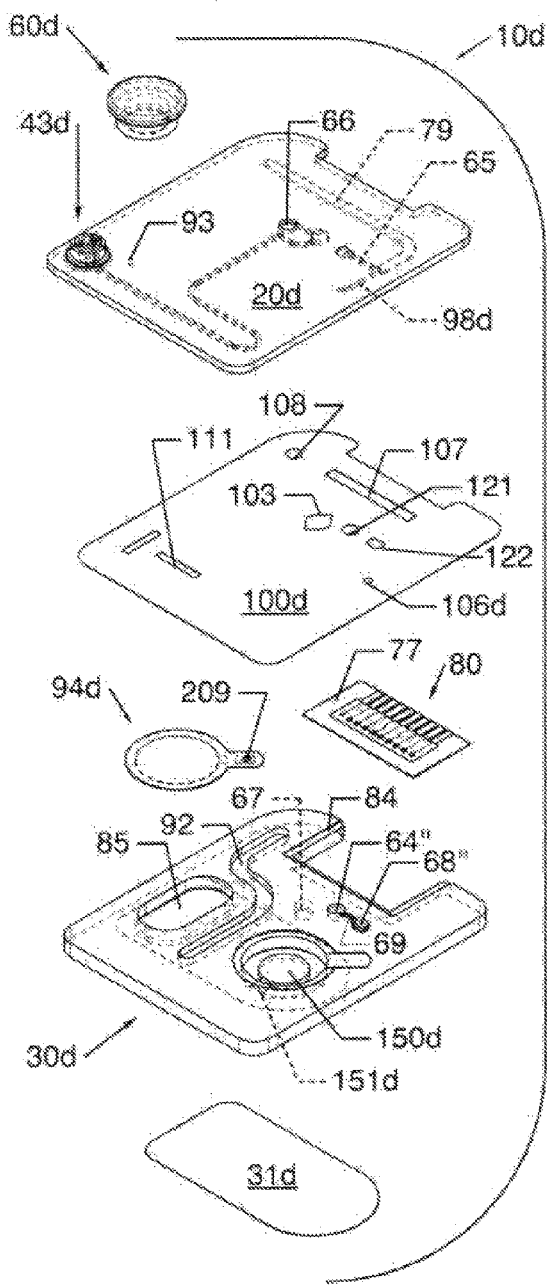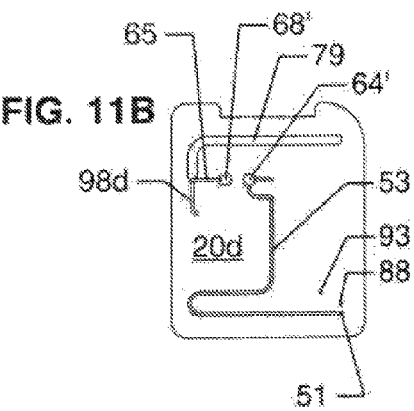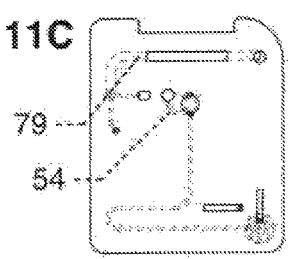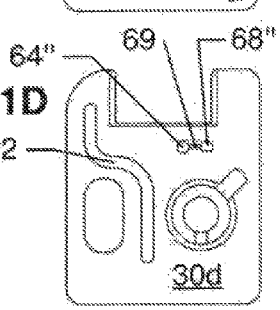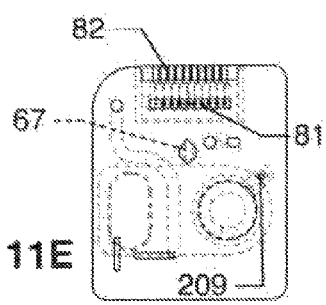

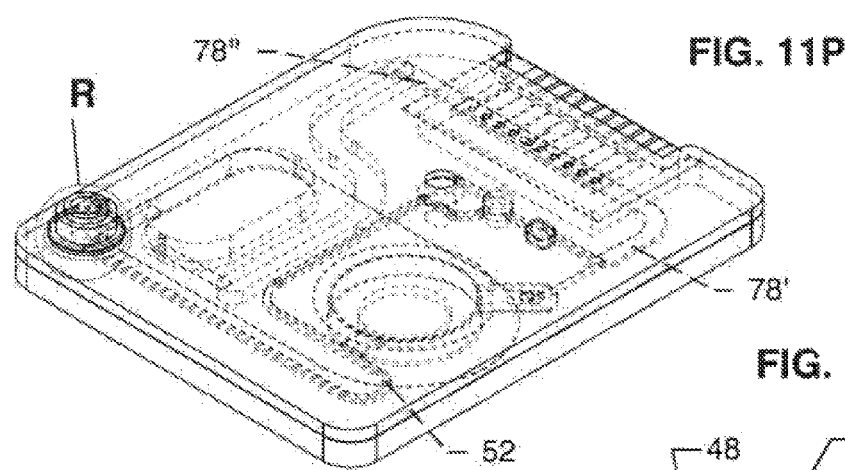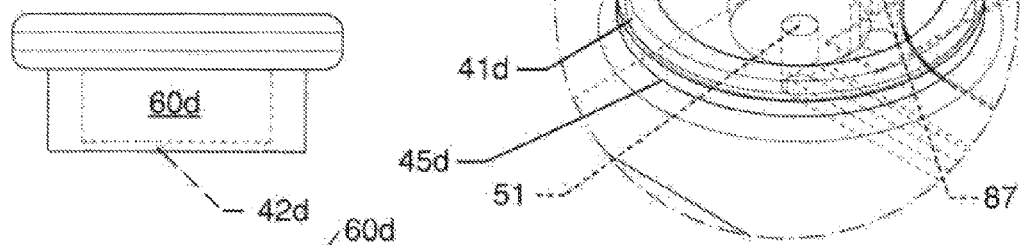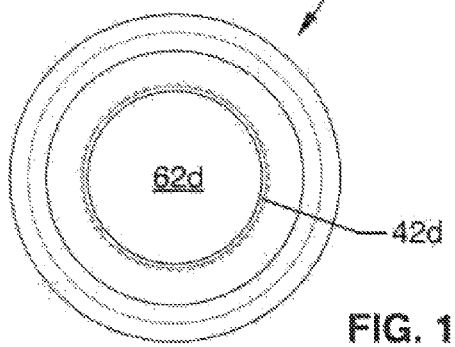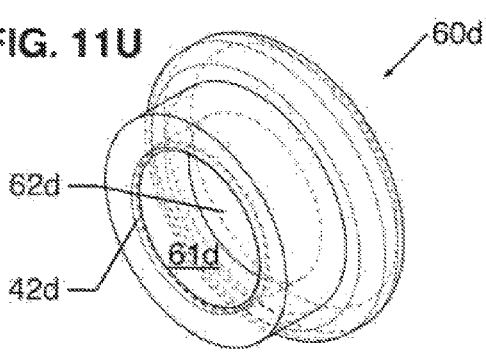

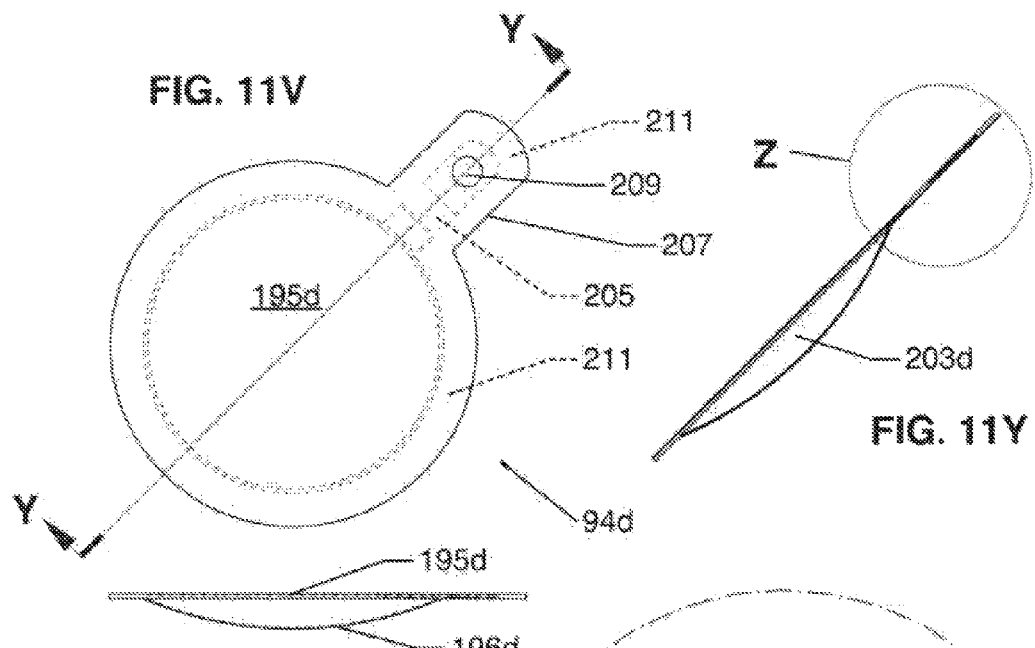
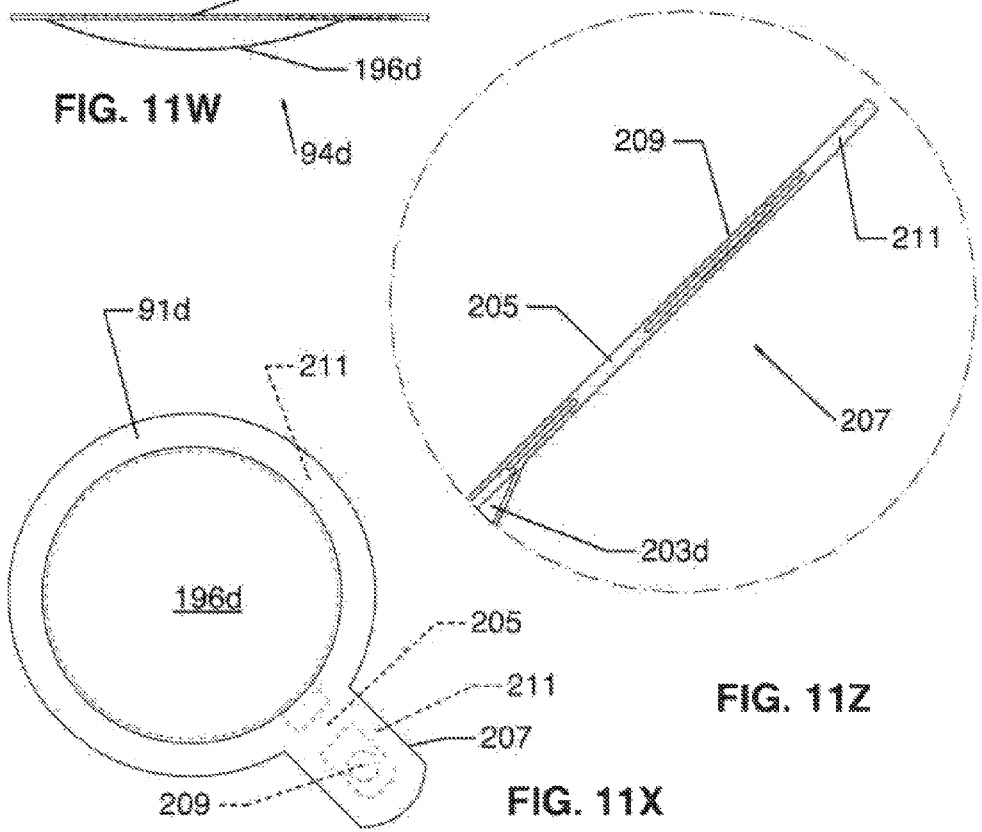

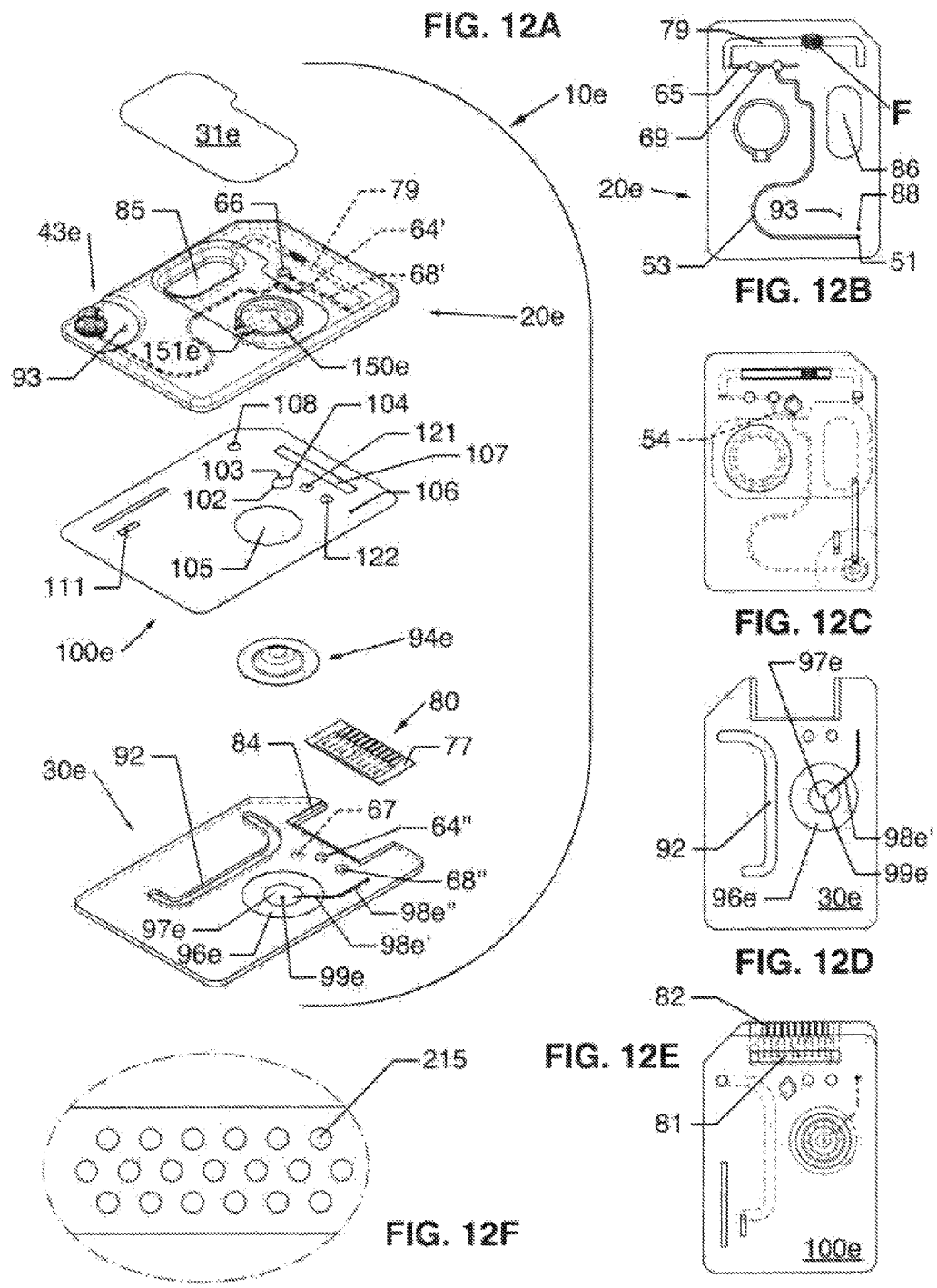

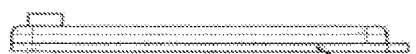
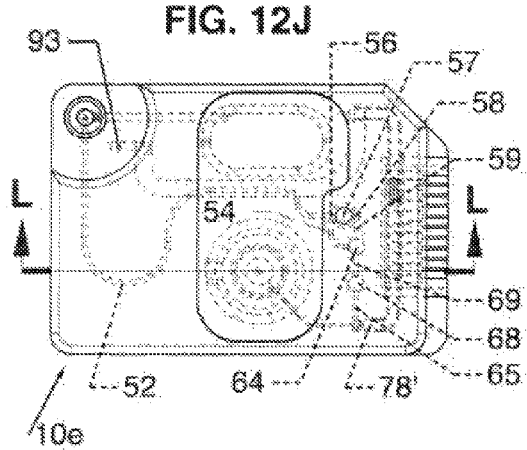
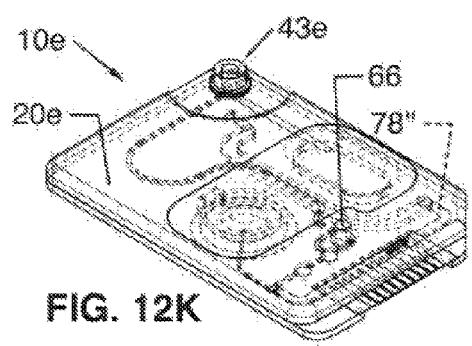
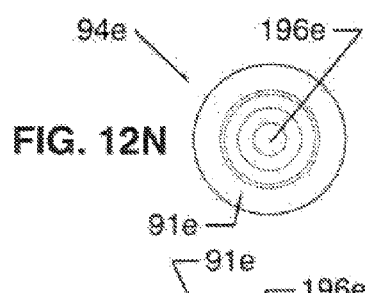
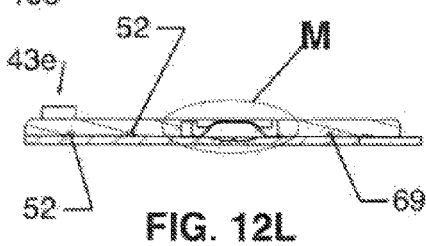
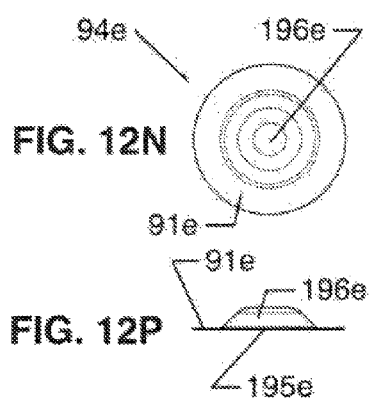
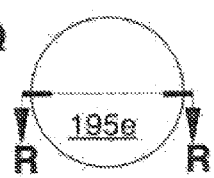

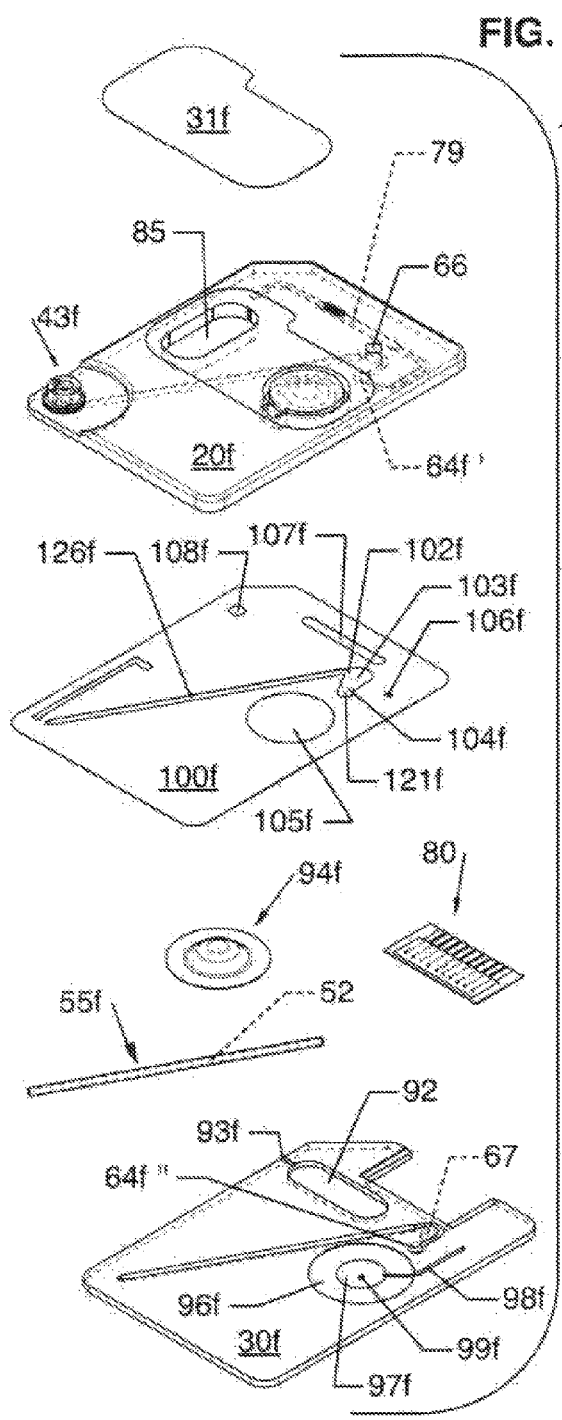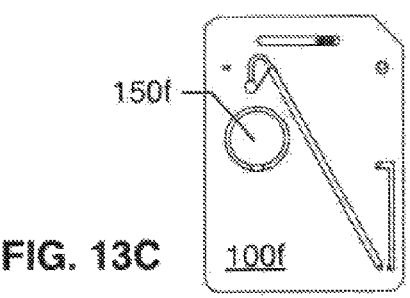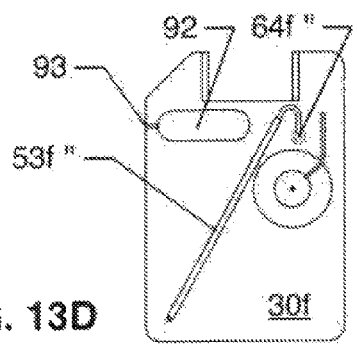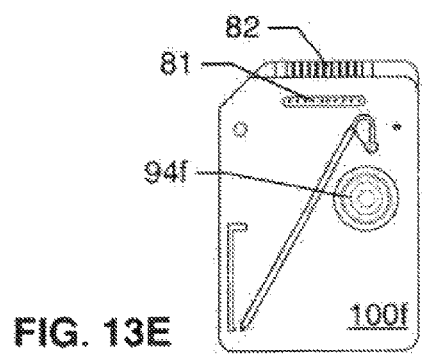

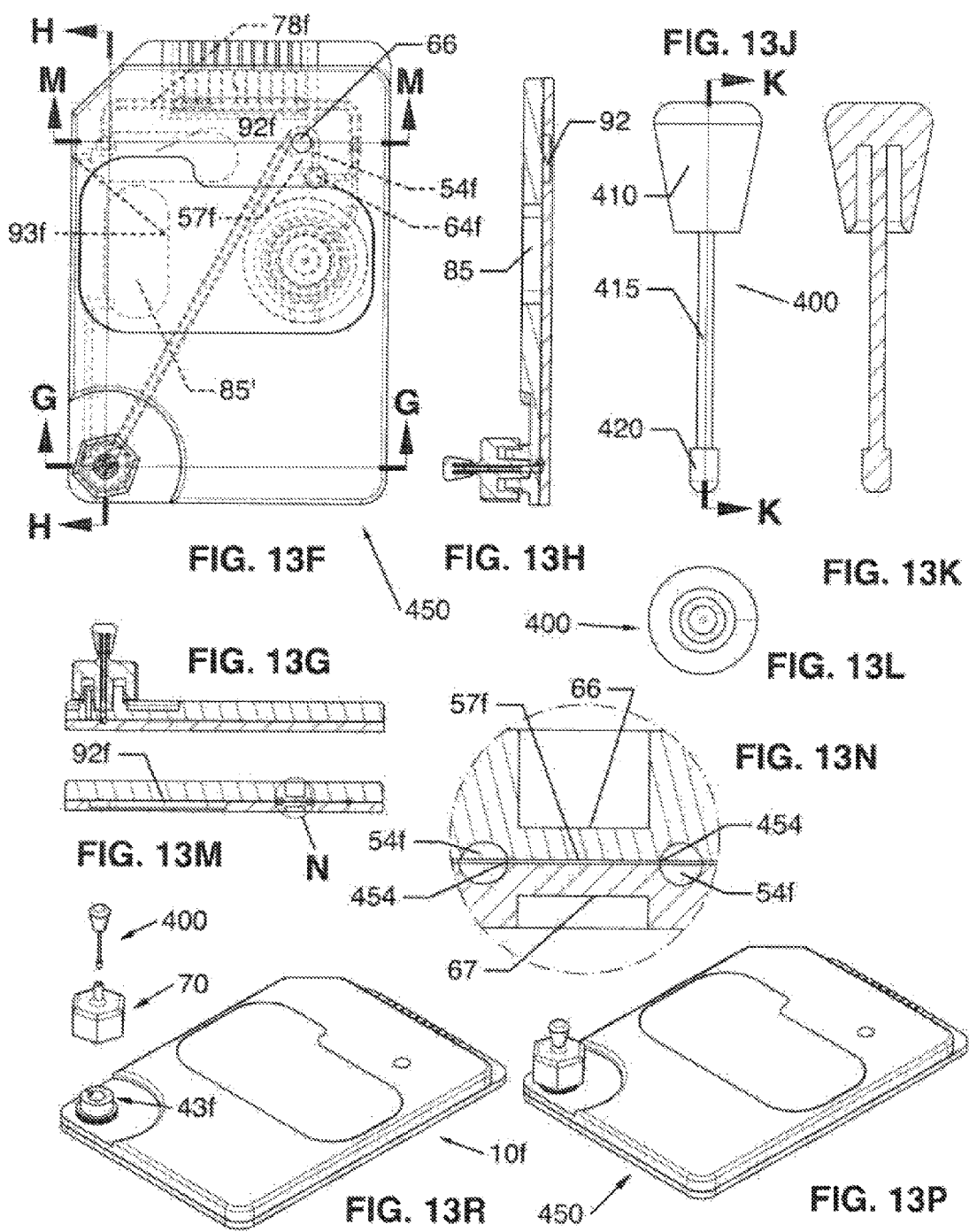

JOINT SPECTROSCOPIC AND BIOSENSOR SYSTEM FOR POINT-OF-CARE TESTING

RELATED APPLICATIONS

This application is a continuation of PCT Application No. PCT/CA2015/050455, filed on May 20, 2015; U.S. Provisional Patent Application No. 62/114,700, filed on Feb. 11, 2015; and U.S. Provisional Patent Application No. 62/006,066, filed on May 31, 2014; entitled, "JOINT SPECTROSCOPIC AND BIOSENSOR SYSTEM FOR POINT-OF-CARE TESTING". All of these previously filed applications are hereby incorporated by reference.

FIELD OF THE INVENTION

The invention relates to a disposable cartridge and an analyzer for point-of-care testing (POCT) of a patient's blood, using a combination of spectroscopic and biosensor measurements.

BACKGROUND OF THE INVENTION

There are many medical diagnostic tests that require a fluid, for example, blood (sometimes referred to as whole blood), serum, plasma, cerebrospinal fluid, synovial fluid, lymphatic fluid, calibration fluid, and urine. With respect to blood, a blood sample is typically withdrawn in either an evacuated tube containing a rubber septum, or a syringe, and sent to a central laboratory for testing. The eventual transfer of blood from the collection site to the testing site results in inevitable delays. Moreover, the red blood cells are alive and continue to consume oxygen during any delay in testing, which in turn changes the chemical composition of the blood sample, from the time the blood sample is collected to the time the blood sample is analyzed, measured or tested.

One example of a blood analysis technique that is affected by delay in testing and transfer of blood from the blood collection device to the analyzer, is CO-oximetry. CO-oximetry is a spectroscopic technique that is used to measure the different Hemoglobin (Hb) species present in a blood sample, for example, Oxy-Hb, Deoxy-Hb, Met-Hb, Carboxy-Hb and Total-Hb. Some Co-oximeters can also measure Sulf-Hb and Fetal-Hb. The results of CO-oximetry is used to provide Hb Oxygen Saturation ($sO_2$) measurements in two ways: 1) Functional $sO_2$ is defined as the ratio of Oxy-Hb to the sum of Oxy-Hb and Deoxy-Hb; and 2) Fractional $sO_2$ is defined as the ratio of Oxy-Hb to the Total-Hb.

If the blood sample is exposed to air, the $sO_2$ measurements may become falsely elevated, as oxygen from the air is absorbed into the blood sample. CO-oximetry usually requires hemolyzing the red blood cells (hemolysis) using a sound generator, in order to make the blood sample more transparent for spectroscopic measurement; blood with intact red cells scatter significantly more electromagnetic radiation (EMR) than hemolyzed blood. Hemolysis can also be accomplished by mixing a chemical for example a detergent, with the blood. Parameters that can be measured in blood by spectroscopic techniques (or spectroscopy, sometimes referred to as spectrometry) are limited by the amount of EMR absorbed by the analytes measured. In contrast, for example without limitation, hydrogen ions (which determine pH) and electrolytes (e.g. sodium, potassium, and chloride) do not absorb EMR in the approximate wavelength range of about 300 nm to 2500 nm. Therefore, if this wavelength range is used to conduct spectroscopic measurements of Hb species, then these important parameters, i.e., hydrogen ions and electrolytes, must be measured by another means.

Another example of a blood analysis technique that is affected by the aforementioned sources of error is blood gases. Traditionally, blood gas measurement includes the partial pressure of oxygen ($pO_2$), the partial pressure of carbon dioxide ($PCO_2$), and pH. From these measurements, other parameters can be calculated, for example, $sO_2$, bicarbonate, base excess and base deficit. Blood gas and electrolyte measurements usually employ biosensors, also referred to as electrochemical sensors or electrochemical detectors. Bench-top analyzers are available, which perform the following: (1) measurement of blood gases, (2) CO-oximetry, or (3) measurement of blood gases and CO-oximetry. Some combinations of diagnostic measurement instruments also include electrolytes, and other measurements for example lactate and creatinine. Because these instruments are large and expensive, they are usually located in central laboratories. Biosensor technology is also limited by the blood parameters biosensors can measure. To the inventor's knowledge, biosensors are not currently available for performing CO-oximeters. U.S. Pat. Nos. 5,096,669 and 7,094,330 to Lauks et al, as examples, describe in details cartridges that employ biosensor technology for POCT. In particular, they teach about pH measurement (a potentiometric measurement), blood gas measurement (a potentiometric and an amperometric measurement for $pCO_2$ and $pO_2$ respectively), and hematocrit measurement (a conductivity measurement). U.S. Pat. No. 7,740,804 to Samsoondar (the present inventor) teaches disposable cartridges for spectroscopic measurement (e.g. CO-oximetry) for POCT using unaltered blood. U.S. Pat. Nos. 5,430,542 and 6,262,798 to Shepherd describes a method for making disposable cuvettes having a pathlength in the range of 80 to 130 micrometers for performing CO-oximetry measurement on unaltered blood.

Blood tests for assessing a patient's oxygenation and acid-base status may include pH, $sO_2$, $CO_2$, and Total Hb. The leading POCT analyzers used to assess a patients acid-base status estimate $sO_2$ from a measured partial $pO_2$, and estimate Total Hb from a measured hematocrit. Both hematocrit and $pO_2$ are measured using biosensors.

$sO_2$ calculated from $pO_2$ is criticized in the literature because: 1) $pO_2$ measures the $O_2$ dissolved in the blood plasma, which accounts for only about 1% of the total oxygen in blood—the remaining 99% of blood oxygen is bound to Hb; 2) it is assumed that the patient's red blood cells (RBC) contain normal levels of 2,3-diphosphoglycerate; and 3) the patient has normal levels of dyshemoglobins e.g., Carboxy-Hb and Met-Hb. Dyshemoglobins are onnfunctional Hbs. Temperature and pH which are also sources of error are usually corrected for.

Total Hb estimated from hematocrit measurement by conductivity is criticized in the literature because: 1) a certain RBC Hb concentration is assumed for all patients; 2) alteration in plasma protein, electrolytes, white cells, and lipids are sources of errors in hematocrit measurement. These assumptions can lead to significant errors in managing seriously ill patients. Moreover, Hb measurement is preferred over hematocrit measurement for evaluating chronic anemia and blood loss. Unnecessary blood transfusion due to underestimation of Hb from hematocrit is a major concern.

In choosing a POCT analyzer, a user must understand clearly the parameters that are actually measured and the parameters that are calculated from measured parameters.

Measurement of Total Hb and $sO_2$ performed by spectroscopy provide the best measurement of a patient's oxygenation status, because they are more accurate than results calculated from hematocrit and $pO_2$ respectively. Lab analyzers can easily combine biosensor and spectroscopic technologies because analyzer size is not a limitation. Currently, no small POCT analyzer is available that provides blood gases (includes pH) and CO-oximetry. Some POCT vendors provide a solution in the form of a separate POCT analyzer just for performing CO-oximetry, which complements their blood gas POCT analyzer.

Since CO-oximetry measures functional Hb species, and non-functional Hb species like Carboxy-Hb and Met-Hb, a physician can continue to confidently monitor a patient's oxygenation status non-invasively using a Pulse Oximeter. According to best practice, pulse oximetry should only be used after verifying that the patient's blood does not contain significant amount of non-functional Hb. The presence of elevated non-functional hemoglobin is a source of error in pulse oximetry. The present invention can use capillary blood as well as arterial blood, which provides a major advantage for babies. Obtaining arterial blood is painful, must be performed by a qualified person like a physician, and the resulting blood loss in babies is clinically significant. This cartridge of the present invention will also facilitate monitoring Met-Hb in neonates during treatment with nitric oxide for respiratory distress, and facilitate measuring bilirubin for assessing neonatal jaundice. The use of capillary blood also makes the present invention an attractive tool for monitoring $sO_2$, Carboxy-Hb (increased due to carbon monoxide poisoning resulting from smoke inhalation) and pH in firefighters and other victims of smoke inhalation. Most of these victims will be treated with oxygen, which elevates the $pO_2$, therefore $pO_2$ cannot be used to assess the blood oxygen content. CO-oximetry is therefore essential to victims of smoke inhalation. Capillary blood is usually obtained from a finger, heel or ear lobe prick. The capillary blood can be altered to more closely resemble arterial blood by applying a heating pad to the site that will be pricked.

U.S. Pat. No. 8,206,650 to Samsoondar (the present inventor) teaches the combination of spectroscopy and biosensor technologies in one disposable cartridge, and can therefore provide pH, blood gases and CO-oximetry on a small POCT analyzer. The users are provided with the convenience of applying the sample once, as opposed to using a first analyzer that employs biosensor technology alone, and a second analyzer that employs spectroscopy alone. However, U.S. Pat. No. 8,206,650 does not provide details required by a person with ordinary skill in the art, for making a functional cartridge, and further does not provide details that can be applied to a cartridge manufacturing process.

U.S. Pat. No. 8,206,650 provides a single cartridge option that can be used to test blood from a syringe like arterial blood, and capillary blood at the surface of a body part, which is a very important consideration when the patient is a neonate. However, the option for obtaining capillary blood is limited. A person of ordinary skill in the art of blood gases will appreciate that the $pO_2$ will be overestimated significantly due to atmospheric contamination; current practice includes inserting the open of a capillary tube inside the drop of blood, quickly sealing the ends of the capillary tube, and taking the sample to an analyzer.

U.S. Pat. No. 8,206,650 teaches the use of an air chamber/bladder to force blood from an optical chamber into a biosensor conduit, but it does not teach any means for mitigating blood flow into the air bladder when the optical chamber receives the blood from the cartridge inlet. Since blood is very precious, especially from a baby, it is not desirable that any of the blood should be wasted. It is possible that when blood is drawn into the cartridge taught in U.S. Pat. No. 8,206,650, blood could at least enter the conduit connecting the air chamber with the inlet chamber. This blood will not contribute to filling the biosensor conduit for biosensor measurements. Other limitations of the cartridge described in U.S. Pat. No. 8,206,650 will become apparent as the various embodiments of the present invention are described.

SUMMARY OF THE INVENTION

In accordance with an aspect of an embodiment of the present invention, there is provided a system for measurement of at least two hemoglobin species in a patient's blood sample by spectroscopy, and measurement of at least pH of the blood sample by biosensor, for assessing the patient's oxygenation and acid-base status. The system comprises a disposable cartridge for processing a portion of the blood sample, the cartridge comprising a housing; a cartridge inlet in the housing for engaging one of a syringe containing the blood sample and a capillary adaptor for transferring a portion of the blood sample from a puncture site of a body part of the patient to the cartridge; a blood storage conduit within the housing having a proximal end close to the cartridge inlet and a distal end away from the cartridge inlet; a blood storage conduit entrance at the proximal end of the blood storage conduit; an optical chamber for receiving the blood from the distal end of the blood storage conduit and for measuring the at least two hemoglobin species; an optical chamber overflow chamber fluidly connected with the optical chamber; at least one optical window, wherein at least a portion of the at least one optical window is in alignment with at least a portion of the optical chamber; a biosensor conduit within the housing for receiving the blood from the optical chamber overflow chamber, the biosensor conduit comprising at least a portion of a pH biosensor; an air bladder; an air bladder exit port, having an arrangement with the blood storage conduit entrance for providing pressurized air to the blood storage conduit via the blood storage conduit entrance, for urging the blood into the biosensor conduit; a waste receptacle for receiving liquid waste from the biosensor conduit; and a waste receptacle vent for relieving pressure in the waste receptacle. The system further comprises a cap for sealing the cartridge inlet; and an analyzer comprising an analyzer housing; a slot in the analyzer housing for receiving the disposable cartridge containing the blood sample; a source of EMR; at least one photodetector; a processor for controlling the analyzer; and at least two calibration algorithms installed on the processor for measuring the at least two hemoglobin species. The system is adjustable between a sealed configuration and an unsealed configuration. In the sealed configuration, and not in the unsealed configuration, the system comprises a closed air passage connecting the air bladder exit port to the blood storage conduit entrance for communicating the pressurized air from the air bladder exit port to the blood storage conduit entrance. In the unsealed configuration, and not in the sealed configuration, the blood storage conduit entrance is configured to receive the blood.

In accordance with an aspect of another embodiment of the present invention, there is provided a disposable cartridge for operation with a joint spectroscopic and biosensor blood analyzer for measurement of at least two hemoglobin species in a patient's blood sample by spectroscopy, and measurement of at least pH of the blood sample by biosensor, for assessing the patient's oxygenation and acid-base status, the cartridge comprising a housing having at least a first housing member and a second housing member bonded together by a gasket. The housing comprises a cartridge inlet; a blood storage conduit within the housing having a proximal end close to the cartridge inlet and a distal end away from the cartridge inlet; an optical chamber within the housing for receiving the blood from the distal end of the blood storage conduit and for measuring the at least two hemoglobin species, the optical chamber comprising an optical chamber depth dimension orthogonal to the gasket; an optical chamber overflow chamber fluidly connected with the optical chamber; a biosensor conduit within the housing for receiving the blood from the optical chamber overflow chamber, the biosensor conduit comprising a proximal end, a distal end and at least a portion of a pH biosensor; a calibration fluid pouch nested in the housing and containing calibration fluid for at least calibrating the pH biosensor; a calibration fluid conduit for transporting released calibration fluid to the biosensor conduit; a waste receptacle for receiving liquid waste from the biosensor conduit; a vent for relieving pressure in the waste receptacle; and an air bladder and an air bladder exit port within the housing for providing pressurized air for urging blood from the blood storage conduit into the biosensor conduit. The first housing member comprises one of a first optical window and a first reflecting member. The second housing member comprises one of a second optical window and a second reflecting member, positioned to align with at least a portion of the optical chamber and at least a portion of the one of a first optical window and a first reflecting member. The gasket has a plurality of cut-outs comprising at least a first gasket cut-out positioned to provide fluid connection between the blood storage conduit and the optical chamber, wherein at least a portion of the first gasket cut-out is positioned to align with at least a portion of the optical chamber for collecting spectroscopic data from blood in that portion of the optical chamber; a second gasket cut-out positioned to provide fluid connection between the calibration fluid conduit and the biosensor conduit, the second gasket cut-out disposed around the proximal end of the biosensor conduit; a third gasket cut-out positioned to at least align with the active area of the pH biosensor; a fourth gasket cut-out positioned to provide fluid connection between the distal end of the biosensor conduit and the waste receptacle; and a fifth gasket cut-out positioned to provide fluid connection between the air bladder and the air bladder exit port.

In accordance with an aspect of yet another embodiment of the present invention there is provided a disposable cartridge adapted for insertion along an insertion plane into the slot of a joint spectroscopic and biosensor analyzer for measurement of at least two hemoglobin species in a patient's blood sample by spectroscopy, and measurement of at least pH of the blood sample by biosensor, for assessing the patient's oxygenation and acid-base status. The cartridge comprises a housing; a cartridge inlet in the housing for receiving the blood sample; a blood storage conduit within the housing having a proximal end close to the cartridge inlet and a distal end away from the cartridge inlet; an optical chamber within the housing for receiving the blood from the distal end of the blood storage conduit and for measuring the at least two hemoglobin species, the optical chamber comprising an optical depth dimension orthogonal to the insertion plane; at least one optical window in the housing positioned to align with at least a portion of the optical chamber for collecting spectroscopic data from blood in that portion of the optical chamber; an optical chamber overflow chamber in fluid connection with the optical chamber for receiving blood from the optical chamber; a blood shunt for providing fluid connectivity between the distal end of the blood storage conduit and the optical chamber overflow chamber, the blood shunt having a maximum shunt depth dimension orthogonal to the insertion plane, and wherein the maximum shunt depth dimension is substantially larger than the optical chamber depth dimension, for a more efficient blood flow from the distal end of the blood storage conduit to the biosensor conduit; a biosensor conduit within the housing for receiving the blood from the optical chamber overflow chamber, the biosensor conduit having at least one biosensor for measuring the at least pH of the blood sample; an air bladder and an air bladder exit port within the housing for providing pressurized air for urging blood from the blood storage conduit into the biosensor conduit; a waste receptacle for receiving waste liquid from the biosensor conduit; and a waste receptacle vent for relieving pressure in the waste receptacle.

In accordance with an aspect of an implementation of the present invention there is provided a method for assessing a patient's oxygenation and acid-base status. The method comprises providing a disposable cartridge comprising a cartridge inlet for receiving blood from one of a syringe containing the blood from the patient and a capillary adaptor for transferring a portion of blood from a puncture site of a body part of the patient to the cartridge; a blood storage conduit having a proximal end and a distal end, wherein the proximal end is fluidly connected to the cartridge inlet; an optical chamber fluidly connected to the blood storage conduit at the distal end; a biosensor conduit comprising at least a pH biosensor to measure blood pH, the biosensor conduit being fluidly connected to the optical chamber; a calibration fluid pouch containing calibration fluid; and an air bladder. The method further comprises providing a cap for sealing the cartridge inlet; providing an analyzer comprising a slot, a source of EMR, and a processor comprising at least two calibration algorithms for facilitating measurement of at least two hemoglobin species; filling the blood storage conduit and the optical chamber with blood from the patient; sealing the cartridge inlet with the cap to provide a sealed cartridge, after filling. When the cartridge inlet is sealed and not when filling the blood storage conduit with blood, the method further comprises providing a pathway for pressurized air from the air bladder exit port to the proximal end of the blood storage conduit. When filling the blood storage conduit with blood and not when the cartridge inlet is sealed, the method further comprises blocking a portion of the blood storage conduit receiving the blood from the air bladder exit port to isolate the air bladder exit port from the blood. The method further comprises inserting the sealed cartridge into the slot of the analyzer; irradiating the blood in the optical chamber with the source of EMR and collecting spectroscopic data; applying the at least two calibration algorithms to the spectroscopic data and obtaining concentrations of the at least two hemoglobin species; calculating hemoglobin oxygen saturation from the concentrations of the at least two hemoglobin species; calibrating the pH biosensor by at least releasing calibration fluid from the calibration fluid pouch and bringing the calibration fluid in contact with the pH biosensor; activating the air bladder to provide a pressurized air flow through the pathway for the pressurized air to the proximal end of the blood storage conduit to bring some of the blood sample in contact with the pH biosensor, after the step of calibrating; and measuring the blood pH, after the steps of irradiating the optical chamber and activating the air bladder. The hemoglobin oxygen saturation and the blood pH provide an assessment of the patients oxygenation and acid-base status.

Other aspects and features of the present invention will become apparent to those having ordinary skill in the art, upon review of the following description of the specific embodiments of the invention.

BRIEF DESCRIPTION OF THE DRAWINGS

For a better understanding of the present invention, and to show more clearly how it may be carried into effect, reference will now be made, by way of example, to the accompanying drawings, which illustrate aspects of embodiments of the present invention and in which:

FIG. 2A is a schematic drawing showing details of a top view of the cartridge shown in FIG. 1;

FIG. 2B is a right side view of the cartridge shown in FIG. 2A;

FIG. 2C is a bottom view of the cartridge shown in FIG. 2A;

FIG. 2D is a front view of the cartridge shown in FIG. 2A;

FIG. 2E is a cross-sectional view through the cartridge shown in FIG. 2A along line E-E FIG. 2F is a first detailed view of the detail F of the cartridge shown in FIG. 2A;

FIG. 2G is a perspective view of the cartridge shown in FIG. 2A, with elements 40 and 50 hidden;

FIG. 2H is a second detailed view of the detail H of the cartridge shown in FIG. 2G;

FIG. 4A is a schematic drawing showing details of a top view of the cartridge shown in FIG. 1A, with a capillary adaptor engaged at the cartridge inlet 43;

FIG. 4B is a first cross-sectional view through the cartridge shown in FIG. 4A along line B-B;

FIG. 4C is a second cross-sectional view through the cartridge and the capillary adaptor shown in FIG. 4A along line C-C;

FIG. 4D is a detailed view of detail D of the cartridge shown in FIG. 4B;

FIG. 4E is a front view of the cartridge and capillary adaptor shown in FIG. 4A;

FIG. 4F is a detailed view of detail F of the cartridge shown in FIG. 4C;

FIG. 4G is a perspective view of the cartridge and capillary adaptor shown in FIG. 4A;

FIG. 4H is a perspective view of the capillary adaptor 70 shown in FIG. 4A;

FIG. 5A is a schematic drawing showing details of a top view of the cartridge shown in FIG. 1A, with a cap 60 engaged at the cartridge inlet 43;

FIG. 5B is a first cross-sectional view through the cartridge and cap shown in FIG. 5A along line B-B;

FIG. 5C is a right side view of the cartridge and cap shown in FIG. 5A;

FIG. 5D is a front view of the cartridge and cap shown in FIG. 5A;

FIG. 5E is a perspective view of the cap 60 shown in FIGS. 5C, 5D and 5H;

FIG. 5F is a second cross-sectional view through the cartridge and cap shown in FIG. 5C along line F-F;

FIG. 5G is a detailed view of the detail G of the cartridge shown in FIG. 5B;

FIG. 5H is a perspective view of the cartridge and cap 60 shown in FIG. 5A;

FIG. 8A is a top view of an embodiment of a gasket 100a incorporated in the second embodiment of a cartridge shown collectively in FIG. 7A-FIG. 7E;

FIG. 8B is a top view of an embodiment of a gasket 100a' for use with a modified embodiment (not shown) of a cartridge 10a;

FIG. 8C is a top view of an embodiment of a gasket 100a" for use with a modified embodiment (not shown) of a cartridge 10a;

FIG. 8D is a top view of an embodiment of a gasket 100a''' for use with a modified embodiment (not shown) of a cartridge 10a;

FIG. 9A is an exploded view of a spectroscopic and biosensor cartridge 10b for use with a joint-diagnostic spectroscopic and biosensor analyzer, according to a third embodiment of the cartridge;

FIG. 9B is a detailed view of the underside of the first housing member 20b of the cartridge shown in FIG. 9A.

FIG. 10A is an exploded view of the spectroscopic and biosensor cartridge 10c and cap 60c for use with a joint-diagnostic spectroscopic and biosensor analyzer, according to a fourth embodiment of the cartridge;

FIG. 10B is a bottom view of the first housing member 20c of the cartridge shown in FIG. 10A;

FIG. 10C is a bottom view of the first housing member 20c shown in FIG. 10B, overlaid by and in alignment with the gasket 100c shown in FIG. 10A;

FIG. 10D is a top view of the second housing member 30c of the cartridge shown in FIG. 10A;

FIG. 10E is a top view of the second housing member 30c shown in FIG. 10D (including the biosensor array 80 and calibration fluid pouch 94 shown in FIG. 10A), overlaid by and in alignment with the gasket 100c shown in FIG. 10A;

FIG. 10F is a top view of the cartridge shown in FIG. 10A, with a cap 60c engaged at the cartridge inlet 43c;

FIG. 10G is a right side view of the cartridge and cap shown in FIG. 10F;

FIG. 10H is a bottom view of the cartridge and cap shown in FIG. 10F;

FIG. 10J is a first cross-sectional view through the cartridge and cap shown in FIG. 10F along line J-J;

FIG. 10K is a second cross-sectional view through the cartridge shown in FIG. 10F along line K-K;

FIG. 10L is a third cross-sectional view through the cartridge shown in FIG. 10H along line L-L;

FIG. 10M is a fourth cross-sectional view through the cartridge and cap shown in FIG. 10H along line M-M;

FIG. 10N is a detailed view of the detail N of the cartridge shown in FIG. 10M, absent the cap 60c;

FIG. 10P is a perspective view of the cartridge shown in FIG. 10A and FIG. 10F, absent the cap 60c;

FIG. 10Q is a front view of the cap 60c shown in FIG. 10A;

FIG. 10R is a detailed view of the detail R of the cartridge shown in FIG. 10P;

FIG. 10S is a bottom view of the cap 60c shown in FIG. 10Q;

FIG. 10T is a cross-sectional view through the cap 60c shown in FIG. 10S along line T-T;

FIG. 10U is a perspective view of the cap 60c shown in FIG. 10Q;

FIG. 11A is an exploded view of the spectroscopic and biosensor cartridge 10d and cap 60d for use with a joint-diagnostic spectroscopic and biosensor analyzer, according to a fifth embodiment of the cartridge;

FIG. 11B is a bottom view of the first housing member 20d of the cartridge shown in FIG. 11A;

FIG. 11C is the bottom view of the first housing member 20d shown in FIG. 11B, overlaid by and in alignment with the gasket 100d shown in FIG. 11A;

FIG. 11D is a top view of the second housing member 30d of the cartridge shown in FIG. 11A;

FIG. 11E is the top view of the second housing member 30d shown in FIG. 11D (including the biosensor array 80 shown in FIG. 11A), overlaid by and in alignment with the gasket 100d shown in FIG. 11A;

FIG. 11P is a perspective view of the cartridge shown in FIG. 11A and FIG. 11F;

FIG. 11R is a second detailed view of the detail R of the cartridge shown in FIG. 11P;

FIG. 11S is a front view of the cap 60d shown in FIGS. 11A and 11F;

FIG. 11T is a bottom view of the cap 60d shown in FIG. 11S;

FIG. 11U is a perspective view of the cap 60d shown in FIG. 11S;

FIG. 11V is a top view of a calibration fluid pouch 94d having a frangible seal 205;

FIG. 11W is a front view of the calibration fluid pouch 94d shown in FIG. 11V;

FIG. 11X is a bottom view of the calibration fluid pouch 94d shown in FIG. 11V;

FIG. 11Y is a cross-sectional view of the calibration fluid pouch 94d shown in FIG. 11V along line Y-Y;

FIG. 11Z is a detailed view of the detail Z of the calibration fluid pouch 94d shown in FIG. 11Y.

FIG. 12A is an exploded view of the spectroscopic and biosensor cartridge 10e for use with a joint-diagnostic spectroscopic and biosensor analyzer, according to a sixth embodiment of the cartridge;

FIG. 12B is a bottom view of the first housing member 20e of the cartridge shown in FIG. 12A;

FIG. 12C is the bottom view of the first housing member 20e shown in FIG. 12B, overlaid by and in alignment with the gasket 100e shown in FIG. 12A;

FIG. 12D is a top view of the second housing member 30e of the cartridge shown in FIG. 12A;

FIG. 12E is the top view of the second housing member 30e shown in FIG. 12D (including the biosensor array 80 shown in FIG. 12A), overlaid by and in alignment with the gasket 100e shown in FIG. 12A;

FIG. 12F is a detailed view of the detail F of the cartridge shown in FIG. 12B; showing a plurality of blind holes 215 disposed at the roof of the biosensor conduit, for trapping air;

FIG. 12G is a right side view of the cartridge 10e shown in FIG. 12A;

FIG. 12H is a back view of the cartridge 10e shown in FIG. 12G;

FIG. 12J is a top view of the cartridge 10e shown in FIG. 12G;

FIG. 12K is a perspective view of the cartridge 10e shown in FIG. 12A;

FIG. 12L is a cross-sectional view through the cartridge shown in FIG. 12J along line L-L;

FIG. 12M is a detailed view of the detail M of the cartridge shown in FIG. 12L;

FIG. 12N is a top view of a calibration fluid pouch 94e shown in FIG. 12A;

FIG. 12P is a front view of a calibration fluid pouch 94e shown in FIG. 12N;

FIG. 12Q is a bottom view of a calibration fluid pouch 94e shown in FIG. 12N;

FIG. 12R is a cross-sectional view through the calibration fluid pouch 94e shown in FIG. 12Q along line R-R.

FIG. 13A is an exploded view of the spectroscopic and biosensor cartridge 10f for use with a joint-diagnostic spectroscopic and biosensor analyzer, according to a seventh embodiment of the cartridge;

FIG. 13B is a bottom view of the first housing member 20f of the cartridge shown in FIG. 13A;

FIG. 13C is the bottom view of the first housing member 20f shown in FIG. 13B, overlaid by and in alignment with the gasket 100f shown in FIG. 13A;

FIG. 13D is a top view of the second housing member 30f of the cartridge shown in FIG. 13A;

FIG. 13E is the top view of the second housing member 30f shown in FIG. 13D (including the biosensor array 80 and calibration fluid pouch 94f shown in FIG. 13A), overlaid by and in alignment with the gasket 100f shown in FIG. 13A;

FIG. 13F is a top view of joint-diagnostic spectroscopic and biosensor system 450 showing an embodiment of the cartridge 10f shown collectively in FIGS. 13A-13E and an embodiment of a piston assembly 400 shown in FIG. 13J for a capillary adaptor 70 shown in FIG. 4H;

FIG. 13G is a first cross-sectional view through the system 450 shown in FIG. 13F along line G-G;

FIG. 13H is a second cross-sectional view through the system 450 shown in FIG. 13F along line H-H;

FIG. 13J is a front view of an embodiment of a piston assembly 400 for a capillary adaptor;

FIG. 13K is a cross-sectional view through the piston assembly 400 shown in FIG. 13J along line K-K;

FIG. 13L is a top view of the embodiment of a piston assembly 400 shown in FIG. 13J;

FIG. 13M is a third cross-sectional view through the system 450 shown in FIG. 13F along line M-M;

FIG. 13N is a detailed view of the detail N of the system 450 shown in FIG. 13M;

FIG. 13P is a perspective view of the system 450 shown in FIG. 13F;

FIG. 13R is a partially exploded view of the system 450 shown in FIG. 13P;

FIG. 14A is a perspective view of a joint-diagnostic spectroscopic and biosensor system showing an embodiment of an analyzer 310, and an embodiment of a cartridge 10f;

Figure 14A:
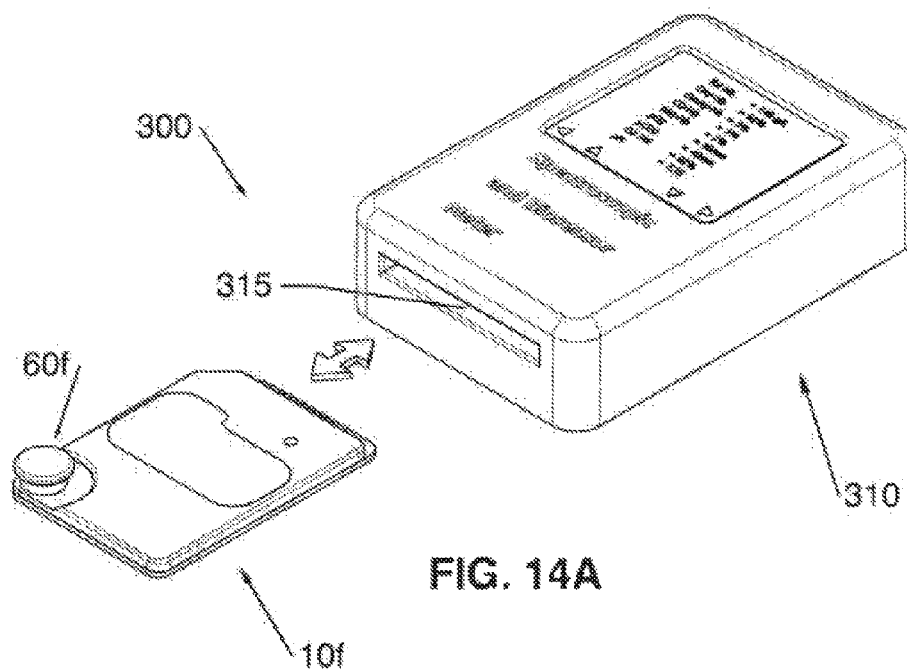
Figure 14B:
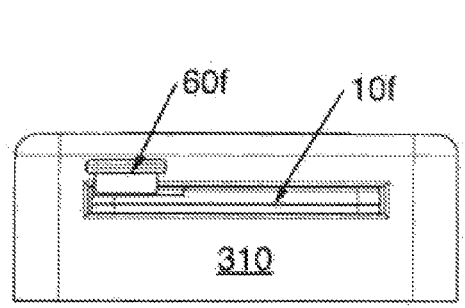
Figure 14C:
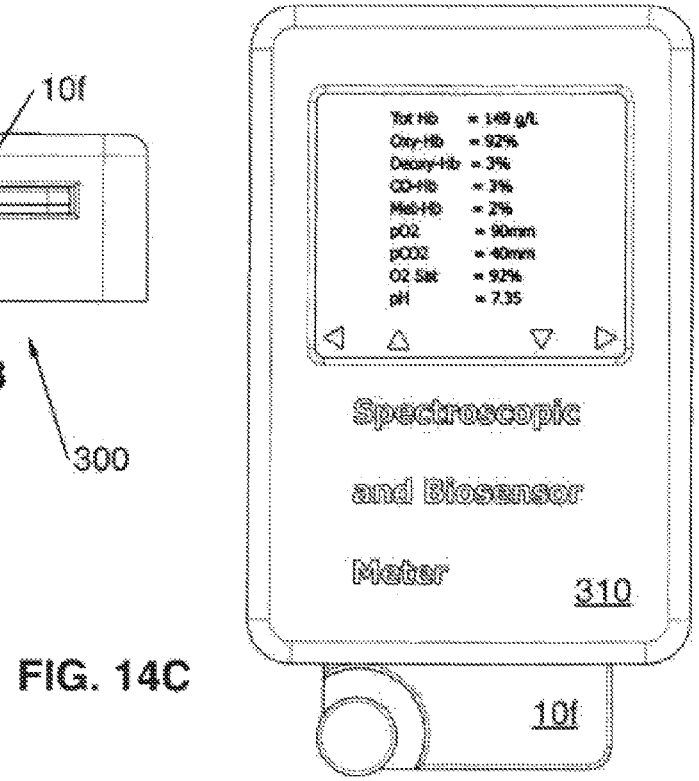

FIG. 14B is a front view of the joint-diagnostic spectroscopic and biosensor system show in FIG. 14A, with the cartridge 10f fully inserted into the slot 315 of the analyzer 310; and FIG. 14C is a top view of the joint-diagnostic spectroscopic and biosensor system show in FIG. 14B.

DETAILED DESCRIPTION OF PREFERRED ASPECTS OF THE INVENTION

The invention provides a system for joint spectroscopic and biosensor measurement of at least two hemoglobin species in a patient's blood sample by spectroscopy, and measurement of at least the blood pH by biosensor. The terms biosensor, electrochemical sensor and electrochemical detector are sometimes used interchangeably, and they have the same meaning in this description. The system comprises a disposable cartridge adapted for insertion into a slot of an analyzer, and the results are used for assessing a patient's oxygenation and acid-base status.

Some embodiments of the system include: an analyzer described in part in U.S. Pat. No. 8,206,650, the analyzer having some of the following: i) a power supply, which is optionally in the form of disposable or rechargeable batteries; ii) a source of electromagnetic radiation (EMR), for example one or more LEDs, a tungsten lamp, one or more lasers, or any combination thereof; iii) a slot in the analyzer housing for receiving a disposable cartridge, which will be described in details later; iv) a photodetector for measuring EMR transmitted through or reflected from a blood sample within the optical chamber and for providing an EMR-based signal derived from the EMR transmitted through or reflected from the blood sample; v) a processor for controlling the analyzer and in communication with the photodetector for receiving the EMR-based signal, and at least one calibration algorithm installed in the processor for transforming the EMR-based signal into a hemoglobin specie concentration; vi) an input contact in the slot for receiving the sample biosensor data wherein the sample biosensor data is used to prepare a biosensor test result, for example pH; vii) means for releasing the calibration fluid from the pouch and transporting released calibration fluid to the biosensor conduit for calibrating at least the pH biosensor prior to measuring the pH of the blood sample; and viii) means for maintaining the active area of the biosensor at a predetermined temperature.

When the electrical input contact mates with the biosensor electrical contact of the cartridge, the optical chamber of the cartridge becomes positioned to receive the EMR from the EMR source.

Some embodiments of the system also include: viii) means for handling the blood sample, for example, a) a syringe containing the blood, and b) a capillary adaptor capable of transferring capillary blood directly from punctured skin of the body part of a patient to the cartridge; and ix) a cap for sealing the cartridge inlet.

The means for calibrating the at least one biosensor includes: a) a pouch within the housing containing calibration fluid; b) means for releasing fluid from the calibration pouch; and c) a calibration fluid conduit for transporting the released calibration fluid to the biosensor conduit. Those skilled in the art will appreciate that the electrical signals generated from the biosensor after it comes in contact with a calibration fluid of know composition, and the known concentration of the analyte in the calibration fluid, can be used to generate a calibration algorithm for the analyte, and therefore for the sake of brevity, the mathematics involved in biosensor calibration will not be discussed here. The biosensor calibration also requires mating of the cartridge biosensor electrical contacts and the analyzer electrical input connection.

The current practice when testing capillary blood on a blood gas analyzer or a CO-oximeter is to collect the capillary blood in a capillary tube, and subsequently transfer the blood from the capillary tube to the analyzer. This transfer of blood from the capillary tube to the analyzer presents sources or error, for example: a) cellular metabolism continues after blood is collected, and the error is proportional to the delay in testing; and b) opportunity for atmospheric contamination by incorporation of air bubbles in the capillary tube, which is subsequently mixed into the blood; an external magnet is used to move a piece of wire located inside the capillary tube, forward and backward along the capillary tube, in order to mix the sample. The present invention provides a capillary adaptor designed to eliminate this step of sample transfer. The atmosphere contains about 21% oxygen, therefore for direct measurement (CO-oximetry) or indirect measurement (i.e. calculating $sO_2$ from measured $pO_2$) of oxygen saturation, the blood must be protected from atmospheric contamination in order to minimize errors.

When a cartridge is inserted properly in the slot of the analyzer, the cartridge biosensor electrical contact mates with the analyzer electrical contact, bringing the optical chamber of the cartridge in position to receive EMR from the EMR source. Those skilled in the art will appreciate that the EMR could also be channeled to the optical chamber by optical fibers. The EMR transmitted through the blood sample in the cartridge, or reflected from the blood sample, impinges upon one or more photodetectors within the analyzer. Calibration algorithms for spectroscopic measurements are preferably installed within the processor of the analyzer, for transforming the spectroscopic signals into analyte measurements. Calibration algorithms for biosensor measurements are preferably installed within the processor of the analyzer, for transforming the biosensor signals into analyte measurements, but some biosensors require calibration prior to sample measurement. The measurements are usually in concentration units, but those skilled in the art will appreciate that other parameters can be measured, for example without limitations, the ratio of the concentrations of two different analytes.

In some embodiments, the joint-diagnostic spectroscopic and biosensor analyzer further comprises a display screen for viewing the results and aiding the operator in use of the analyzer, as well as buttons for manipulating the display function. Those skilled in the art will appreciate that the analyzer could be connected to a host computer. Therefore, some embodiments of the system also comprise at least one communication port for interfacing with other instruments. Other non-limiting examples of other instruments are a printer, and diagnostic testing instruments like a pulse oximeter or some other non-invasive testing instrument. The optional communication port is also used to upgrade information in the analyzer's processor, as well as to upload information from the analyzer's processor. Another optional port in the housing of some embodiments of the joint-diagnostic spectroscopic and biosensor analyzer is provided for charging the power supply within the analyzer. Those skilled in the art will appreciate that a single port can be used for both data transfer and a power supply, for example without any limitation, a USB (Universal Serial Bus) port. In some embodiments of a system, data transfer to and from the analyzer is accomplished by wireless means that are known by one of skill in the art, and therefore for the sake of brevity wireless communication means will not be discussed here.

Some embodiments of the joint-diagnostic spectroscopic and biosensor analyzer comprise one photodetector (photodiode), or more than one photodetector assembled as an array of detectors in a spectrometer, wherein the spectrometer comprises a grating for dispersing EMR emerging from the fluid sample, into wavelength components. The analyzer optionally comprises one or more focusing lenses between the disposable cartridge and the spectrometer. A person of ordinary skill in the art will appreciate that other forms of optical detection, for example CCD (charged-couple device) can be used, and are therefore considered to be within the scope of the invention.

In some embodiments, the interior walls of the cartridges are treated with a hydrophillic coating to promote even spreading of the blood within the optical chamber, and to promote movement of blood along the flow path by capillary action.

The optical chamber is located along a flow path, and the optical chamber has at least one optical window for spectroscopic analysis of the blood. The at least one optical window is in alignment with at least a portion of the optical chamber. A flow path may also contain one or more reagents, anywhere along the flow path, for example without limitation, an anticoagulant, a hemolyzing reagent, or a reagent that reacts with an analyte to enhance the absorbance of EMR. The optical chamber is specifically designed to reduce the average attenuation of EMR due to scattering of EMR by the intact red blood cells in a blood sample, without having to hemolyze the red blood cells using sound waves or hemolyzing chemicals. Preferably the depth of the optical chamber, i.e., the internal distance between the optical windows, is in an approximate range of about 50 microns to about 200 microns. In a preferred embodiment, the depth of the optical chamber is substantially uniform across the optical windows. In some embodiments, the depth of the optical chamber is not uniform across the optical windows, and is within the scope of the present invention. A person of ordinary skill in the art will appreciate that although the optical windows are illustrated as circular elements, they can have other shapes, for example without being limited, oval and square shapes. In some embodiments, the area of an optical window that is in alignment with an optical chamber is in an approximate range of about 1 sq. millimeter to about 100 sq. millimeters. For the sake of minimizing sample volume, a more preferred optical window area that is in alignment with the optical chamber is in an approximate range of about 1 sq. millimeter to about 10 sq. millimeters.

The biosensor conduit is located along a flow path, and the biosensor conduit may have one or more than one biosensors for analyzing the blood. Those skilled in the art will appreciate that biosensors may include various transducer arrangements that convert at least one property of the fluid sample into an electrical signal, wherein the transducer comprises at least one active surface for contacting the fluid sample. In some embodiments, the active surface is one of a chemical sensitive surface, or an ionic sensitive surface, and wherein the biosensor comprises at least one of a transistor, an ion-selective membrane, a membrane-bound enzyme, a membrane-bound antigen, a membrane-bound antibody, or a membrane-bound strand of nucleic acid. The disposable cartridge also comprises at least one biosensor electrical contact, and the cartridge slot of the analyzer also comprises at least one analyzer electrical contact. Although the examples illustrated show the cartridge electrical output contact as flat pins in an array, those skilled in the art will appreciate that the electrical contacts can mate in other ways, for example the electrical contacts described in U.S. Pat. No. 8,206,650.

Some embodiment of a joint-diagnostic spectroscopic and biosensor analyzer optionally comprises a barcode reader for reading a barcode on the disposable cartridge (not shown), the barcode containing at least information regarding calibration of a biosensor. The barcode also optionally contains information about the joint-diagnostic spectroscopic and biosensor analyzer. Some embodiments of disposable cartridges comprise radio frequency identification (RFID) tags. In some embodiments, the disposable cartridge further comprises a calibration fluid pouch containing a calibration fluid that is arranged in fluid connection with a biosensor conduit. For cartridges with calibration fluid pouches, the joint-diagnostic spectroscopic and biosensor system further comprises means for rupturing the calibration fluid pouches, for example, which should not be considered limiting in any way, a rotating cam, or a reciprocating plunger, and a spike in the cartridge housing. In some embodiments, the pouch itself contains an object with multiple spikes, which ruptures the calibration pouch when pressure is applied to a flexible member at the surface of the cartridge, over the calibration fluid pouch. In some embodiments, a portion of the seal of the calibration pouch is substantially weaker by design, than the rest of the seal, for easy rupture after pressure is applied. These weaker seal portions are sometimes referred to as frangible seals.

Some embodiments of cartridges also include at least one visible fill line or indicator serving as a marker providing a user with a visual indicator relating to the sufficiency of the blood sample in the optical chamber. Preferably the cartridge housing is made of transparent plastic for easy viewing of the blood inside the cartridge.

An embodiment of the disposable cartridge comprises: a) a housing 10; b) a cartridge inlet 43 in the housing for receiving a syringe 90 containing arterial or venous blood, or a capillary adaptor 70 engaged with the cartridge inlet 43, for transferring capillary blood from a punctured site of a patient's body part to the cartridge; c) a blood storage conduit entrance 51 for receiving arterial or venous blood contained in a syringe 90, or for receiving capillary blood directly from the punctured skin of a body part via the capillary adaptor 70; d) a blood storage conduit 52 within the housing having a proximal end 52' for receiving the blood via the blood storage conduit entrance 51, and a distal end 52" away from the blood storage conduit entrance 51; e) an optical chamber inlet 56 for receiving the blood from the distal end of the blood storage conduit 52"; f) an optical chamber 57 for receiving blood from the optical chamber inlet 56 and measuring at least two hemoglobin species; g) an optical chamber outlet 58 for releasing blood from the optical chamber; h) an optical chamber overflow chamber 59 fluidly connected with the optical chamber outlet 58 and the biosensor conduit 78; i) a biosensor conduit 78 within the housing for receiving the blood from the optical chamber overflow chamber 59, the biosensor conduit having at least one biosensor for measuring at least blood pH; j) an enlarged cavity 64, which is considered to be part of the optical chamber overflow chamber; k) an air bladder 85' and an air bladder exit port 88 within the housing for providing pressurized air for forcibly urging the blood from the blood storage conduit 52 into the biosensor conduit 78; l) a waste receptacle cavity 92 for receiving discarded liquid; m) a waste receptacle vent 93 for relieving pressure in the waste receptacle; n) means for mitigating blood flow through the air bladder exit port 88 when the blood storage conduit receives the blood from the blood storage conduit entrance 51; o) means for displacing the blood from the blood storage conduit 52 without causing any blood leakage through the cartridge inlet 43; and p) means for calibrating at least one biosensor. The means for calibrating the at least one biosensor includes a calibration fluid pouch 94 within the housing containing calibration fluid, means for rupturing the calibration pouch, and a calibration fluid conduit comprising a calibration fluid groove 98 for transporting the calibration fluid from the pouch 94 to the biosensor conduit 78. U.S. Pat. No. 5,096,669 describes analyzer means for depressing and rupturing a calibration pouch. Although the cartridge embodiments shown comprise means for calibrating the biosensors, cartridge embodiments having factory-calibrated biosensors and therefore do not require means for calibrating the biosensors, are within the scope of the invention.

In some embodiments of a disposable cartridge, the blood storage conduit begins at a the blood storage conduit entrance and terminates at the optical chamber, and the volume of the blood storage conduit is in an approximate range of about 50 microliters to about 100 microliters. A small sample size is preferred for babies, but for $pO_2$ measurement, air bubbles can create greater errors in smaller samples. Therefore the size of the samples must be balanced between allowable errors and the amount of blood the patient can provide without causing the patient harm.

Examples of means for mitigating blood flow through the air bladder exit port 88 when the blood storage conduit 52 receives the blood from the blood storage conduit entrance 51, include: a) a check valve (not shown) disposed between the air bladder 85' and the air bladder exit port 88; b) a syringe 90 inserted into the cartridge inlet 43 in order to make fluid connection with the blood storage conduit entrance 51 and to simultaneously bypass the air bladder exit port 88, wherein the air bladder exit port 88 is disposed strategically near the blood storage conduit entrance 51 for cutting off fluid communication between the blood storage conduit entrance 51 and the air bladder exit port 88; and c) a capillary adaptor 70 inserted in the cartridge inlet 43 to make fluid connection with the blood storage conduit entrance 51 and to simultaneously bypass the air bladder exit port 88, wherein the air bladder exit port 88 is disposed strategically near the blood storage conduit entrance 51 for cutting off fluid communication between the blood storage conduit entrance 51 and the air bladder exit port 88. Air bladder usually contains air, but it is understood that other gases can be used, for example nitrogen, for the purpose of urging liquid along a path. U.S. Pat. No. 5,096,669 describes analyzer means for activating the air bladder.

The system is adjustable between a sealed configuration and an unsealed configuration. In the sealed configuration, and not in the unsealed configuration, the system comprises a closed air passage connecting the air bladder exit port 88 to the blood storage conduit entrance 51 for communicating the pressurized air from the air bladder exit port 88 to the blood storage conduit entrance 51. In the unsealed configuration, and not in the sealed configuration, the blood storage conduit entrance 51 is configured to receive the blood.

An example of means for mitigating blood leakage through the cartridge inlet 43 include; a) a cap 60 for providing an air-tight covering over the cartridge inlet 43; b) an air bladder 85'; and c) an air bladder exit port 88. For illustrative purposes, a frictionally engaged cap is used, and should not be considered limiting in any way. In some embodiments of a cap, at least the top portion of the cap is sufficiently rigid so it is not depressed (relative to the rest of the cap) when the cap is pushed against the cartridge inlet. The rigidity prevents the depressed top portion of the cap from rebounding when the cap is released. The rebound would create suction, and the suction could cause regurgitation of the blood. In some embodiments of a system, the cap is tethered to the cartridge.

Although no screw caps are shown, a person of ordinary skill in the art will appreciate that, for example, a screw cap can be used to seal the cartridge inlet. Some caps used with some cartridge embodiments have additional features, and are described with specific embodiments of a cartridge.

In some embodiments, the blood storage conduit has a length dimension measured from the proximal end to the distal end and a cross-sectional area orthogonal to the length dimension, the size of the cross-sectional area being sufficiently small to receive the blood by capillary action, and the size being substantially uniform throughout a substantial portion of the length dimension. Some of the cross-sectional areas shown are circular, but a person with ordinary skill in the art will appreciate that other shapes can be used, and are therefore considered to be within the scope of the present invention.

The optical chamber of an embodiment of the cartridge has a depth dimension orthogonal to a plane of insertion of the cartridge into the slot of the analyzer, wherein the depth dimension is in an approximate range of about 50 microns to about 200 microns. In some specific embodiments described in greater details later, the optical chamber is defined by a cut-out in a gasket. In some embodiments (not shown), the depth dimension of the optical chamber is greater than the thickness of the gasket.

An embodiment of a capillary adaptor 70 comprises: a) a length in the approximate range of about 2 centimeter to about 4 centimeters; b) a capillary adaptor inlet member 71 shaped like a capillary tube having a capillary adaptor inlet port 72 for insertion into the blood sample, for example a drop of blood at the puncture site of a patient's body part; c) a capillary adaptor outlet member 75 shaped like the male end of a syringe for insertion into the cartridge inlet 43, the capillary adaptor outlet member 75 having a capillary adaptor outlet port 76 for mating with a blood storage conduit entrance 51; d) a capillary adaptor handgrip 74 disposed between the inlet port 72 and the outlet port 76 for handling the adaptor with fingers; and e) a capillary adaptor lumen 73 for fluidly connecting the inlet port 72 and the outlet port 76, the lumen having a diameter in the approximate range of about 0.5 millimeter to about 2 millimeters (see FIG. 4H).

Another aspect of the disposable cartridge for operation with a joint spectroscopic and biosensor blood analyzer for measurement of at least two hemoglobin species in blood by spectroscopy, and measurement of at least blood pH by biosensor, is a housing comprising: A) a first housing member; B) a second housing member; and C) a double-sided sticky gasket, are illustrated. Although several embodiments of the cartridge comprising the first and second housing members bonded together by the double-sided sticky gasket, it should be understood that these are non-limiting examples of disposable cartridges for operation with a joint spectroscopic and biosensor blood analyzer for measurement of at least two hemoglobin species in blood by spectroscopy, and measurement of at least blood pH. Although the embodiments of a disposable cartridge are illustrated with a single double-sided sticky gasket, some cartridge embodiments (not shown) comprise more than two housing members, and therefore require more than one double-sided sticky gasket for bonding the additional housing members.

The three components A, B and C will now be discussed first in general terms, and later specific embodiments will be discussed.

A) Some embodiments of the first housing member 20 comprise: a) a cartridge inlet in the first housing member for receiving the blood; b) a calibration fluid pouch window and a paddle overlaid with a flexible laminate for activating release of the calibration fluid from the pouch; c) an air bladder comprising an air bladder cavity and an air bladder window overlaid with a flexible laminate for activating the air bladder; d) one of a first optical window and a first reflecting member for spectroscopic measurement; and e) a biosensor conduit groove for exposing the active areas of the biosensors to the calibration fluid and blood sample sequentially. In some embodiments of the cartridge, the calibration fluid pouch window and paddle, hinged or unhinged, are disposed in the second housing member.

B) Some embodiments of the second housing member 30 comprise: a) one of a second optical window and a second reflecting member for spectroscopic measurement, positioned to at least partially align with the one of a first optical window and a first reflecting member; b) a calibration fluid pouch nest for accommodating the calibration fluid pouch; c) a calibration fluid groove for constructing a calibration fluid conduit when assembled in the cartridge; d) a biosensor receptacle for accommodating the at least one biosensor; and e) a waste receptacle cavity for receiving liquid waste. In some embodiments of the cartridge, the air bladder cavity extends into the second housing member. In other embodiments of a cartridge, the calibration fluid conduit is defined by the calibration fluid groove and the gasket described next in C).

C) The double-sided sticky gasket 100 includes a plurality of cut-outs comprising at least one of the following: 1) a first gasket cut-out positioned to provide fluid connection between the cartridge inlet and the proximal end of a blood storage conduit, for cartridge embodiments having the blood storage conduit groove disposed in the second housing member; 2) a second gasket cut-out positioned to provide fluid connection between the distal end of the blood storage conduit and an optical chamber overflow chamber; 3) a third gasket cut-out positioned to align with a first enlarged cavity in the housing, wherein the first enlarged cavity is one of a cavity in the first housing member, a cavity in the second housing member, and a combination of a cavity in the first housing member and a cavity in the second housing member; 4) a fourth gasket cut-out positioned to provide fluid connection between a calibration fluid conduit and the proximal end of the biosensor conduit; 5) a fifth gasket cut-out positioned to align with a portion of the biosensor conduit groove and the active area of at least one biosensor; 6) a sixth gasket cut-out positioned to provide fluid connection between the distal end of the biosensor conduit and a waste receptacle; 7) a seventh gasket cut-out positioned to provide fluid connection between an air bladder and an air bladder exit port; 8) an eighth gasket cut-out positioned to provide fluid connection between a waste receptacle and a waste receptacle vent; and 9) a ninth gasket cut-out positioned to align with a calibration fluid pouch. A person of ordinary skill in the art would appreciate that if the blood storage conduit in an embodiment is defined by a groove in the first housing member and the gasket, then the first gasket cut-out is not required. A person of ordinary skill in the art would also appreciate that if a calibration fluid pouch comprising a frangible seal is used in an embodiment of a cartridge, as described in a fifth embodiment of the cartridge, then the ninth gasket cut-out is not required. In some embodiments of a cartridge, the waste receptacle is defined by the waste receptacle cavity in the second housing member and the gasket or the first housing member.

In another embodiment of the disposable cartridge, the double-sided sticky gasket further comprises: 10) a tenth gasket cut-out positioned to align with a second enlarged cavity in the housing, wherein the second enlarged cavity is one of a cavity in the first housing member, a cavity in the second housing member, and a combination of a cavity in the first housing member and a cavity in the second housing member.

In yet another embodiment of the disposable cartridge, the double-sided sticky gasket further comprises: 11) an eleventh gasket cut-out positioned to align with the blood storage conduit. Further, in some embodiments of the gasket, the eleventh gasket cut-out is a single gasket cut-out extending from the first gasket cut-out to the second gasket cut-out.

The gasket of other embodiments of a disposable cartridge further comprises one or more of the following: 12) a twelfth gasket cut-out, disposed to join the second gasket cut-out and the third gasket cut-out; 13) a thirteenth gasket cut-out, disposed to join the third gasket cut-out and the tenth gasket cut-out; 14) a fourteenth gasket cut-out, disposed to join the fourth gasket cut-out and the ninth gasket cut-out; 15) a fifteenth gasket cut-out positioned to provide align with an air bladder window; 16) a sixteenth gasket cut-out positioned to align with an air bladder exit port; and 17) a seventeenth gasket cut-out, disposed to join the fifteenth gasket cut-out and the sixteenth gasket cut-out.

In some embodiments of a cartridge, the double-sided sticky gasket has a thickness in the approximate range of about 50 microns to about 200 microns. Although the gaskets are described as sticky gaskets, non-sticky gaskets are considered within the scope of the invention. In embodiments using non-sticky gaskets, some form of adhesive must be applied directly to the housing members at the areas where the gasket makes contact with the housing members, or some other means are used for sandwiching the gasket between the housing members.

The gaskets shown are flat and therefore each side of the gasket defines a plane, wherein both planes are parallel to each other. In some embodiments (not shown), the gasket is substantially flat, wherein each side substantially defines a plane, and wherein the two planes are not parallel. Therefore, it should be understood that reference to a plane orthogonal to the gasket means a plane orthogonal to either of the two planes substantially defined by the respective sides of a substantially flat gasket. As an example, a substantially flat gasket is one where most of the gasket is flat, and some sections comprise dimples and or bumps.

With respect to spectroscopic measurements, those skilled in the art will appreciate the various ways a spectroscopic measurement apparatus can be constructed, and various elements that make up such apparatus. Accordingly, for the sake of brevity, description of basic spectroscopy and a list and function of the elements that make up a spectroscopic apparatus will not be discussed here. Those skilled in the art will appreciate that when the source of EMR is a single source, the single source could be split by a multi-channel optical fiber for providing more than one light paths. An example of a system for detecting the EMR transmitted through or reflected from a sample is an array of photodiodes, but those skilled in the art will appreciate that these spectroscopic elements are just examples and should not be considered limiting for the present invention.

Still with respect to spectroscopic measurements, the examples shown describe an apparatus that operates in transmission mode. Those skilled in the art will appreciate that the spectroscopic apparatus of a joint-diagnostic spectroscopic and biosensor analyzer can also operate in reflectance mode by placing a reflecting member in the analyzer slot designed for receiving the cartridge, on one side of the optical chamber, such that the EMR transmitted through the sample would be reflected off the reflecting member, whereby the reflected EMR would enter the sample for the second time. In a diagnostic measurement instrument or analyzer operating in the reflectance mode, both the EMR source and the photodetector could be on the same side of the optical chamber. Moreover, those skilled in the art will also appreciate that instead of installing a reflecting member around the slot in the housing of the analyzer, one side of the wall-portions of the optical chamber of the cartridge could be coated with a reflecting material.

A blood storage conduit is defined by a first blood storage conduit groove in one of the housing members, and either the gasket or the other housing member with or without a second blood storage conduit groove. In the embodiments where the blood storage conduit allows the blood to make contact with a surface of the gasket, the gasket is preferably made of hydrophilic material for enhancing wetting of the gasket. The blood storage conduit in some embodiments is simply a cut-out in the gasket with no grooves in either of the housing members. For clarity, the blood storage conduit in some embodiments, comprise a groove in the first housing member aligned with the gasket cut-out, or a groove in the second housing member alignment with the gasket cut-out. In yet other embodiments, the gasket cut-out is aligned with a first groove in the first housing member and a second groove in the second housing member. The illustration of the various embodiments of the blood storage conduit can be applied to other conduits, for example the biosensor conduit, the blood shunt and the calibration fluid conduit, and are considered to be within the scope of the invention.

Because there can be so many combinations of grooves and gasket cut-outs, the ones illustrated in the specific embodiments described later, are chosen with the objective of minimizing the volume of blood required. Minimizing sample volume is particularly important with respect to neonatal care. However, sample volume is not necessarily a limiting factor, as in the case of a patient with substantial body weight having a catheter inserted in an artery. Therefore, embodiments that require substantial blood volume are considered to be within the scope of the invention, unless specified otherwise. The effect of air bubbles on $pO_2$ in a small sample must also be considered, as mentioned previously.

The housing of some embodiments of the disposable cartridge comprises a blood shunt beginning at the blood storage conduit entrance and terminating at the optical chamber. In some embodiments of a cartridge, the shunt has a cross-sectional area orthogonal to the plane of insertion of the cartridge into the slot of the analyzer, and the optical chamber has an optical depth dimension orthogonal to a plane of insertion of the cartridge into the slot of the analyzer. In these embodiments, the smallest dimension of the blood shunt cross-sectional area is substantially larger than the optical depth dimension. In other embodiments of a cartridge, the cartridge comprises a blood shunt in the housing for providing fluid connectivity between the distal end of the blood storage conduit and the optical chamber overflow chamber, the blood shunt having a maximum bypass depth dimension orthogonal to the plane of insertion of the cartridge into the slot of the analyzer, and wherein the maximum bypass depth dimension is substantially larger than the optical depth dimension, for enhancing blood flow from the distal end of the blood storage conduit to the biosensor conduit.

The details of the drawings are discussed next, to further describe specific embodiments of the invention. These embodiments are examples only, and a person of ordinary skill in the art will understand that other embodiments that are not explicitly illustrated are implied. Attempts are made to use the same reference numerals for similar elements and in some cases letters are appended to the end of the reference numerals to denote the embodiment of the invention illustrated. For example, the letters a, b, c, d, e and f are used to refer to the $2^{nd}$, $3^{rd}$, $4^{th}$, $5^{th}$, $6^{th}$ and $7^{th}$ embodiment of the invention respectively. For easy reference, Table 1 provides a list of the reference numerals used, and a brief description of the structural features referred to.

TABLE 1

| Reference Numerals | Description of Structural Features |
|---|---|
| 10 | Cartridge housing of a first embodiment of a cartridge |
| 10a | Cartridge housing of a second embodiment of a cartridge |
| 10b | Cartridge housing of a third embodiment of a cartridge |
| 10c | Cartridge housing of a fourth embodiment of a cartridge |

TABLE 1-continued

| Reference Numerals | Description of Structural Features |
|---|---|
| 10d | Cartridge housing of a fifth embodiment of a cartridge |
| 10e | Cartridge housing of a sixth embodiment of a cartridge |
| 10f | Cartridge housing of a seventh embodiment of a cartridge |
| 20 | First housing member of a first embodiment of a cartridge |
| 20a | First housing member of a second embodiment of a cartridge |
| 20b | First housing member of a third embodiment of a cartridge |
| 20c | First housing member of a fourth embodiment of a cartridge |
| 20d | First housing member of a fifth embodiment of a cartridge |
| 20e | First housing member of a sixth embodiment of a cartridge |
| 20f | First housing member of a seventh embodiment of a cartridge |
| 30 | Second housing member of a first embodiment of a cartridge |
| 30a | Second housing member of a second embodiment of a cartridge |
| 30b | Second housing member of a third embodiment of a cartridge |
| 30c | Second housing member of a fourth embodiment of a cartridge |
| 30d | Second housing member of a fifth embodiment of a cartridge |
| 30e | Second housing member of a sixth embodiment of a cartridge |
| 30f | Second housing member of a seventh embodiment of a cartridge |
| 31c | Flexible member of a fourth embodiment of a cartridge |
| 31d | Flexible member of a fifth embodiment of a cartridge |
| 31e | Flexible member of a sixth embodiment of a cartridge |
| 31f | Flexible member of a seventh embodiment of a cartridge |
| 40 | First flexible member of a cartridge |
| 41c | Snap fit lip (shown as a chamfer) of cartridge inlet of a fourth embodiment of a cartridge |
| 41d | Snap fit lip (shown as a combination of a fillet and a surface parallel to direction of cap travel) of cartridge inlet of a fifth embodiment of a cartridge |
| 42c | A discontinuous annular snap fit element of a cap used with the fourth embodiment of a cartridge |
| 42d | An annular snap fit seal of a cap used with the fifth embodiment of a cartridge |
| 43 | A cartridge inlet of a first embodiment of a cartridge |
| 43a | A cartridge inlet of a second embodiment of a cartridge |
| 43b | A cartridge inlet of a third embodiment of a cartridge |
| 43c | A cartridge inlet of a fourth embodiment of a cartridge |
| 43d | A cartridge inlet of a fifth embodiment of a cartridge |
| 43e | A cartridge inlet of a sixth embodiment of a cartridge |
| 43f | A cartridge inlet of a seventh embodiment of a cartridge |
| 44 | Hard layer below second flexible member 50 |
| 45c | Annular snap fit element of a fourth embodiment of a cartridge |
| 45d | Annular snap fit seal element of a fifth embodiment of a cartridge |
| 46 | An annular surface at the top of the cartridge inlet of a first embodiment of a cartridge |
| 46a | An annular surface at the top of the cartridge inlet of a second embodiment of a cartridge |
| 46c | An annular surface at the top of the cartridge inlet of a fourth embodiment of a cartridge |
| 46d | An annular surface at the top of the cartridge inlet of a fifth embodiment of a cartridge |
| 47 | Recess in the annular surface 46 of the cartridge inlet of a first embodiment of a cartridge |
| 47c | Recess in annular surface 46c of the cartridge inlet of a fourth embodiment of a cartridge |
| 47d | Recess in the annular surface 46d of the cartridge inlet of a fifth embodiment of a cartridge |
| 48 | Internal wall of the cartridge inlet 43 of a cartridge |
| 49 | External wall of the cartridge inlet 43 of a cartridge |
| 50 | Second flexible member of a cartridge |
| 51 | A blood storage conduit entrance of a cartridge |
| 52 | A blood storage conduit of a cartridge |
| 52' | Proximal end of a blood storage conduit of a cartridge |
| 52" | Distal end of a blood storage conduit of a cartridge |
| 53 | A blood storage conduit groove of a cartridge |
| 53f' | A blood storage conduit groove of a cartridge in a first housing member of a seventh embodiment of a cartridge |
| 53f" | A blood storage conduit groove of a cartridge in a second housing member of a seventh embodiment of a cartridge |
| 54 | A blood shunt of a cartridge |
| 54f | A blood shunt of a seventh embodiment of a cartridge |
| 55f | A capillary tube that defines most of the blood storage conduit of a seventh embodiment of a cartridge |
| 56 | An optical chamber inlet of an optical chamber of a cartridge, positioned to provide fluid connection between the distal end of the blood storage conduit and the optical chamber |
| 57 | An optical chamber in a cartridge for receiving blood from a blood storage conduit, and positioned to align at least with a portion of an optical window |
| 57f | An optical chamber in a seventh embodiment of a cartridge for receiving blood from a blood storage conduit, and positioned so that at least a portion aligns with an optical window |
| 58 | An optical chamber outlet of an optical chamber of a cartridge, positioned to provide fluid connection with an optical chamber and an optical chamber overflow chamber |
| 59 | An optical chamber overflow chamber |
| 60 | A cap for the cartridge inlet 43 of a cartridge |
| 60c | A cap for cartridge Inlet 43c of a fourth embodiment of a cartridge |
| 60d | A cap for cartridge Inlet 43d of a fifth embodiment of a cartridge |
| 60f | A cap for cartridge Inlet 43f of a seventh embodiment of a cartridge |
| 61 | Internal wall surface of cap 60 |
| 61c | Internal wall surface of cap 60c |
| 61d | Internal wall surface of cap 60d |
| 62 | Underside of cap 60 |
| 62c | Underside of cap 60c |
| 62d | Underside of cap 60d |
| 63c | Pressure release groove in cap 60c |
| 64' | Portion of an enlarged cavity in a first housing member of a cartridge, adjacent to an optical chamber |
| 64f' | Portion of an enlarged cavity in a first housing member of a seventh embodiment of a cartridge |
| 64" | Portion of an enlarged cavity in a second housing member of a cartridge, adjacent to an optical chamber |
| 64f" | Portion of an enlarged cavity in a second housing member of a seventh embodiment of a cartridge |
| 64 | A first enlarged cavity of a cartridge, comprising portions 64', 64", and a gasket cut-out 121 aligned with portions 64' and 64" |
| 64f | An enlarged cavity of a seventh embodiment of a cartridge, comprising portions 64f', 64f", and a gasket cut-out 121f aligned with portions 64f' and 64f" |
| 65 | A connecting groove positioned to provide fluid connection between an enlarged cavity and a biosensor conduit of a cartridge |
| 66 | A first optical window of a cartridge |
| 67 | A second optical window of a cartridge |
| 68' | Portion of a second enlarged cavity in first housing member of a cartridge, adjacent to a first enlarged cavity |
| 68" | Portion of a second enlarged cavity in second housing member of a cartridge, adjacent to a first enlarged cavity |
| 68 | A second enlarged cavity of a cartridge, comprising portions 68', 68" and a gasket cut-out aligned with portions 68' and 68" |
| 69 | An interconnecting groove of a cartridge positioned to provide fluid connection between a first and a second enlarged cavities |
| 70 | A capillary adaptor for use with a cartridge |
| 71 | A capillary adaptor inlet member |
| 72 | A capillary adaptor inlet port |
| 73 | A capillary adaptor lumen |
| 74 | A capillary adaptor handgrip |
| 75 | A capillary adaptor outlet member |
| 76 | A capillary adaptor outlet port |
| 77 | Biosensor substrate for printing elements of the biosensors and for facilitating thermal contact with an analyzer heating element |
| 78 | A biosensor conduit of a cartridge |
| 78f | A biosensor conduit of a seventh embodiment of a cartridge |
| 78' | Proximal end of a biosensor conduit 78 |
| 78" | Distal end of a biosensor conduit 78 |
| 79 | A biosensor conduit groove of a cartridge |

TABLE 1-continued

| Reference Numerals | Description of Structural Features |
|---|---|
| 80 | A biosensor array of a cartridge |
| 81 | Active area of a biosensor array |
| 82 | Biosensor electrical contact |
| 83 | A biosensor receptacle for arranging one or more biosensors in a cartridge |
| 84 | A biosensor receptacle for arranging one or more biosensors in a cartridge in the form of a cut-out ledge in the second housing member, and for exposing the underside of the biosensor(s) to facilitate heating |
| 85 | An air bladder cavity of a cartridge |
| 85' | An air bladder |
| 86 | An air bladder window of a cartridge for facilitating operation of the air bladder |
| 87 | An air bladder conduit of a cartridge to provide fluid connection between an air bladder and an air bladder exit port |
| 88 | An air bladder exit port of a cartridge |
| 90 | A syringe |
| 91 | A calibration fluid pouch flange of a calibration fluid pouch of a cartridge, comprising a perimeter seal |
| 91d | A calibration fluid pouch flange of a calibration fluid pouch 94d, comprising a perimeter seal |
| 91e | A calibration fluid pouch flange of a calibration fluid pouch 94e, comprising a perimeter seal |
| 92 | A waste receptacle cavity of a cartridge |
| 92f | A waste receptacle cavity of a seventh embodiment of a cartridge |
| 93 | A waste receptacle vent of a cartridge |
| 93f | A waste receptacle vent of a seventh embodiment of a cartridge |
| 94 | A calibration fluid pouch for storing and releasing calibration fluid, incorporated in a cartridge |
| 94d | A calibration fluid pouch for storing and releasing calibration fluid having a frangible seal, incorporated in a fifth embodiment of a cartridge |
| 94e | A calibration fluid pouch for storing and releasing calibration fluid, incorporated in a sixth embodiment of a cartridge |
| 94f | A calibration fluid pouch for storing and releasing calibration fluid, incorporated in a seventh embodiment of a cartridge |
| 95 | A calibration fluid pouch window of a cartridge, for facilitating operation of the calibration fluid pouch |
| 95b | A calibration fluid pouch window of a third embodiment of a cartridge, for facilitating operation of the calibration fluid pouch |
| 96 | A calibration fluid pouch nest of a cartridge |
| 96e | A calibration fluid pouch nest of a sixth embodiment of a cartridge |
| 96f | A calibration fluid pouch nest of a seventh embodiment of a cartridge |
| 97 | A calibration fluid pouch spike recess for housing the spike 99 of a cartridge |
| 97e | A calibration fluid pouch spike recess for housing the spike 99e of a sixth embodiment of a cartridge |
| 97f | A calibration fluid pouch spike recess for housing the spike 99f of a seventh embodiment of a cartridge |
| 98' | The proximal end of a calibration fluid groove of a cartridge for receiving calibration fluid from a calibration fluid pouch |
| 98e' | The proximal end of a calibration fluid groove for receiving calibration fluid from a calibration fluid pouch of a sixth embodiment of a cartridge |
| 98" | The distal end of a calibration fluid groove of a cartridge for transferring calibration fluid from the proximal end of a calibration fluid groove to the biosensor conduit |
| 98e" | The distal end of a calibration fluid groove for transferring calibration fluid from the proximal end of a calibration fluid groove to the biosensor conduit of a sixth embodiment of a cartridge |
| 98d | A calibration fluid groove for transferring calibration fluid from a calibration fluid pouch to the biosensor conduit of a fifth embodiment of a cartridge |
| 98f | A calibration fluid groove for transferring calibration fluid from a calibration fluid pouch to the biosensor conduit of a seventh embodiment of a cartridge |
| 99 | A calibration fluid pouch spike of a cartridge |
| 99e | A calibration fluid pouch spike of a sixth embodiment of a cartridge |
| 99f | A calibration fluid pouch spike of a seventh embodiment of a cartridge |
| 100 | Double-sided sticky gasket of a first embodiment of a cartridge |
| 100a | Double-sided sticky gasket of a second embodiment of a cartridge |
| 100a' | First modified form of a double-sided sticky gasket 100a, for an embodiment of a cartridge (not shown) |
| 100a" | Second modified form of a double-sided sticky gasket 100a, for an embodiment of a cartridge (not shown) |
| 100a'" | Third modified form of a double-sided sticky gasket 100a, for an embodiment of a cartridge (not shown) |
| 100b | Double-sided sticky gasket of a third embodiment of a cartridge |
| 100c | Double-sided sticky gasket of a fourth embodiment of a cartridge |
| 100d | Double-sided sticky gasket of a fifth embodiment of a cartridge |
| 100e | Double-sided sticky gasket of a sixth embodiment of a cartridge |
| 100f | Double-sided sticky gasket of a seventh embodiment of a cartridge |
| 101 | Gasket cut-out 101 positioned to provide fluid connection between a cartridge inlet and the proximal end of blood storage conduit of a cartridge |
| 102 | Gasket cut-out 102 positioned to provide fluid connection between the distal end of blood storage conduit and an optical chamber, and positioned to align with an optical chamber inlet 56 |
| 102f | Gasket cut-out 102f positioned to provide fluid connection between the distal end of blood storage conduit and an optical chamber 57f of a seventh embodiment of a cartridge |
| 103 | Gasket cut-out 103 positioned to provide fluid connection between an optical chamber inlet and an optical chamber outlet, and positioned to align with an optical chamber 57 |
| 103f | Gasket cut-out 103f positioned to provide fluid connection between an optical chamber inlet and an optical chamber outlet, and positioned to align with an optical chamber 57f of a seventh embodiment of a cartridge |
| 104 | Gasket cut-out 104 positioned to provide fluid connection between an optical chamber and an optical chamber overflow chamber, and positioned to align with an optical chamber outlet 58 |
| 104f | Gasket cut-out 104f positioned to provide fluid connection between an optical chamber and an optical chamber overflow chamber, and positioned to align with an optical chamber outlet 57f of a seventh embodiment of a cartridge |
| 105 | Gasket cut-out 105 positioned to align with a calibration fluid pouch |
| 105f | Gasket cut-out 105f positioned to align with a calibration fluid pouch of a seventh embodiment of a cartridge |
| 106 | Gasket cut-out 106 positioned to provide fluid connection between a calibration fluid conduit and the proximal end of a biosensor conduit |
| 106d | Gasket cut-out 106d positioned to provide fluid connection between a calibration fluid pouch and the proximal end of a biosensor conduit of the fifth embodiment of a cartridge |
| 106f | Gasket cut-out 106d positioned to provide fluid connection between a calibration fluid conduit and the proximal end of a biosensor conduit of the seventh embodiment of a cartridge |
| 107 | Gasket cut-out 107 positioned to align with a portion of the biosensor conduit groove and the active area of the biosensors |
| 107f | Gasket cut-out 107f positioned to align with a portion of the biosensor conduit groove and the active area of the biosensors of a seventh embodiment of a cartridge |
| 108 | Gasket cut-out 108 positioned to provide fluid connection between the distal end of the biosensor conduit and a waste receptacle cavity |
| 108f | Gasket cut-out 108f positioned to provide fluid connection between the distal end of the biosensor conduit and a waste receptacle cavity of a seventh embodiment of a cartridge |

TABLE 1-continued

| Reference Numerals | Description of Structural Features |
|---|---|
| 109 | Gasket cut-out 109 positioned to align with an air bladder |
| 111 | Gasket cut-out 111 positioned to provide fluid connection between a waste receptacle and a waste receptacle vent. |
| 121 | Gasket cut-out 121 positioned to align with a first enlarged cavity of a cartridge |
| 121f | Gasket cut-out 121f positioned to align with an enlarged cavity 64f of a seventh embodiment of a cartridge |
| 122 | Gasket cut-out 122 positioned to align with a second enlarged cavity of a cartridge |
| 124 | Gasket cut-out 124 positioned to provide fluid connection between gasket cut-out 104 and gasket cut-out 121 |
| 125 | Gasket cut-out 124 positioned to provide fluid connection between gasket cut-out 121 and gasket cut-out 122 |
| 126 | Gasket cut-out 126 positioned to provide fluid connection between gasket cut-out 101 and gasket cut-out 102 |
| 126f | Gasket cut-out 126f positioned to align with a capillary tube 55f of a seventh embodiment of a cartridge |
| 128 | Gasket cut-out 128 positioned to provide fluid connection between gasket cut-out 105 gasket cut-out 106 |
| 133 | Gasket 133 positioned to provide fluid connection between gasket cut-out 109 and gasket cut-out 136 |
| 136 | Gasket cut-out 136 positioned to provide fluid connection between an air bladder and an air bladder exit port 88 |
| 150c | Paddle in the fourth embodiment of a cartridge, for facilitating rupture of calibration fluid pouch |
| 150d | Paddle in the fifth embodiment of a cartridge, for facilitating rupture of calibration fluid pouch |
| 150e | Paddle in the sixth embodiment of a cartridge, for facilitating rupture of calibration fluid pouch |
| 150f | Paddle in the seventh embodiment of a cartridge, for facilitating rupture of calibration fluid pouch |
| 151c | Paddle hinge in the fourth embodiment of a cartridge |
| 151d | Paddle hinge in the fifth embodiment of a cartridge |
| 151e | Paddle hinge in the sixth embodiment of a cartridge |
| 195d | Flat portion of calibration fluid pouch 94d |
| 195e | Flat portion of calibration fluid pouch 94e |
| 196d | Bulging portion of calibration fluid pouch 94d |
| 196e | Bulge of calibration fluid pouch 94e |
| 203d | Calibration fluid pouch cavity of calibration fluid pouch 94d |
| 203e | Calibration fluid pouch cavity of calibration fluid pouch 94e |
| 205 | Frangible seal of calibration fluid pouch 94d to facilitate fluid connection between calibration fluid pouch cavity 203d and calibration fluid outlet 209 |
| 207 | Calibration fluid pouch flange handle of calibration fluid pouch 94d |
| 209 | Calibration fluid outlet of calibration fluid pouch 94d |
| 211 | Non-frangible seal between flat portion 195d and bulge 196d of calibration fluid pouch 94d |
| 215 | Blind hole for trapping air |
| 300 | a joint-diagnostic spectroscopic and biosensor system showing an embodiment of an analyzer and an embodiment of a capped cartridge |
| 310 | An embodiment of an analyzer 310 of a joint-diagnostic spectroscopic and biosensor system 300 |
| 315 | A slot of the analyzer 310 of a joint-diagnostic spectroscopic and biosensor system 300 |
| 400 | An embodiment of a piston assembly for a capillary adaptor |
| 410 | Head of piston assembly 400 |
| 415 | Piston rod of piston assembly 400 |
| 420 | Piston of piston assembly 400 |
| 450 | A joint-diagnostic spectroscopic and biosensor system showing an embodiment of a cartridge 10f, an embodiment of a capillary adaptor 70 engaged with the cartridge 10f, and an embodiment of a piston assembly 400 engaged with the capillary adaptor 70. |
| 454 | A blood shunt slit |

Figure 1:
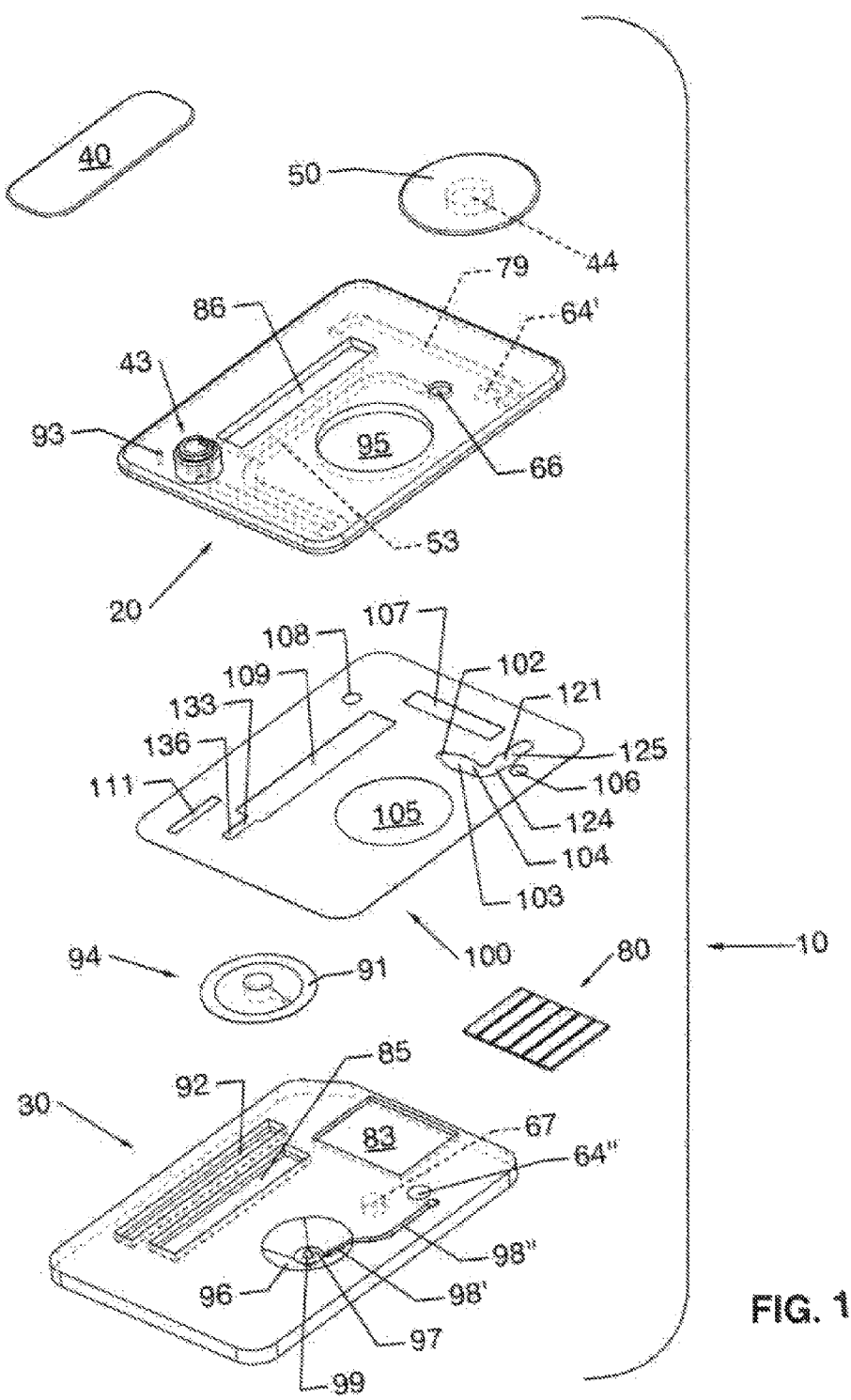
FIG. 1 is an exploded view of a spectroscopic and biosensor cartridge 10 for use with a joint-diagnostic spectroscopic and biosensor analyzer, according to a first embodiment of the cartridge.

Shown in FIG. 1 is an exploded view of the spectroscopic and biosensor cartridge 10 according to a first embodiment of a cartridge. From top to bottom components are listed. The first is flexible member 40, followed by flexible member 50 having a hard layer 44 underneath. Next is the first housing member 20 showing the calibration fluid pouch window 95, the first optical window 66, and the air bladder window 86. The first housing member 20 also reveals the following hidden details: a biosensor conduit groove 79; a blood storage conduit groove 53; and a portion 64' of an enlarged cavity 64. Also shown are a cartridge inlet 43 and a waste receptacle vent 93.

Still referring to FIG. 1, under the first housing member 20 is shown the double-sided sticky gasket 100, having a plurality of gasket cut-outs. Table 1 provides a list of the reference numerals used, and a brief description of the structural features referred to, so for the sake of brevity the description of the gasket cut-outs will not be repeated here. Other embodiments of the cartridge 10 can be made by altering the gasket cut-outs and/or the grooves in the first housing member and/or the grooves in the second housing member. By way of example, four different gaskets are illustrated in FIGS. 8A-8D, and in a second embodiment of the invention, the blood storage conduit groove is shown in the second housing member as 53 in FIG. 7C. In the gasket embodiment illustrated in FIG. 8D, gasket cut-outs 101, 126, 102, 103, 104, 124, 121, 125 and 122 are combined as a single cut-out, and gasket cut-out 136, 133 and 109 are combined as another single cut-out.

Below the gasket 100 in FIG. 1 are shown the calibration fluid pouch 94 and the biosensor array 80, which fit in a calibration fluid pouch nest 96 and a biosensor receptacle 83 respectively, in the second housing member 30. For illustrative purposes, a plurality of biosensors is shown as a biosensor array 80, but it must be understood that the biosensor array comprises one or more than one biosensors. Also shown in the second housing member 30 are: a waste receptacle cavity 92; an air bladder cavity 85; a calibration fluid pouch spike 99, a calibration fluid pouch spike recess 97 for housing the spike 99, a proximal and distal end of a calibration fluid groove for transferring calibration fluid from a calibration fluid pouch to the biosensor conduit, shown as 98' and 98" respectively; a portion 64" of an enlarged cavity 64; and the hidden second optical window 67. The combination of the distal end 98" of the calibration fluid groove and the gasket 100 defines a calibration fluid conduit.

In the first embodiment of a cartridge, the enlarged cavity 64 is shown as a spherically-shaped element (shown collectively in FIGS. 3B and 3C), but some embodiments have other shapes, for example, hemi-spherically shaped, in which case, the hemi-spherically shaped groove is located at either the first housing member or the second housing member, and no gasket cut-out in the optical chamber overflow chamber 59 is required. Other non-limiting examples of shapes of enlarged cavities are polyhedrons. In some embodiments of the cartridge, one or more enlarged cavities in a conduit are provided along the flow path at strategic locations. Some non-limiting examples of optional functions of an enlarged cavity are as follows: i) slowing down blood flow; ii) retaining calibration fluid in the biosensor conduit, and away from the blood sample; iii) retaining sample away from the biosensor conduit, for example during biosensor calibration; iv) purging the optical chamber of blood contaminated with atmospheric oxygen; v) acting as a reservoir for collecting blood when the blood is pushed towards the distal end of the blood storage conduit, after the cap is engaged and also when the piston assembly for a capillary adaptor is inserted into the capillary adaptor lumen; and vi) creating an air bubble. Some non-limiting examples of optional functions of an air bubble are as follows: a) separating calibration fluid from blood sample; and b) removing residual calibration fluid from the biosensor conduit prior to blood flow, thereby mitigating contamination of blood sample with calibration fluid.

Referring collectively to FIG. 2A to FIG. 6E, schematic drawings representing several views of a spectroscopic and biosensor cartridge 10 for use with a joint-diagnostic spectroscopic and biosensor analyzer according to a first embodiment of the disposable cartridge are shown. An example of an analyzer 310 is shown in shown collectively in FIGS. 14A-140. A person of ordinary skill in the art will appreciate that analyzer 310 is only a schematic representation of an example of an analyzer, and it should not be considered limiting in any way.

Shown in FIG. 2A is a top view of cartridge 10 showing the following details: a) electrical contacts 82 of biosensor array 80 shown in FIG. 1; b) an optical chamber inlet 56 (hidden view); c) an optical chamber 57 (hidden view); d) an optical chamber outlet 58 (hidden view); e) an optical chamber overflow chamber 59 (hidden view); f) a first housing member 20; g) a first flexible member 40, which along with an air bladder cavity 85 and the air bladder window 86, define an air bladder 85'; h) a second flexible member 50, which works with calibration fluid pouch window 95, calibration fluid pouch 94, and calibration fluid pouch spike 99, for releasing calibration fluid from the calibration pouch 94; i) a waste receptacle vent 93 for relieving pressure in the waste receptacle defined by the gasket 100 and the cavity 92; and j) a biosensor conduit 78 (hidden view). The calibration fluid is required for calibrating certain biosensors.

Shown in FIG. 2B is a right side view of the cartridge 10 shown in FIG. 2A, showing the following details: a) a first housing member 20; b) a second housing member 30; c) a cartridge inlet 43 for receiving a syringe containing blood, or a capillary adaptor for transferring capillary blood directly from the punctured skin of a body part to the cartridge; and d) the external wall 49 of the cartridge inlet 43. Shown in FIG. 2C is a bottom view of the cartridge 10 shown in FIG. 2A, showing the second housing member 30 and the second optical window 67. Shown in FIG. 2D is a front view of the cartridge 10 shown in FIG. 2A, showing the external wall 49 of the cartridge inlet 43. Shown in FIG. 2E is a cross-sectional view through the cartridge 10 shown in FIG. 2A along line E-E, showing: a) the first flexible member 40; b) the second flexible member 50; c) a waste receptacle cavity 92 for receiving waste liquid; d) an air bladder cavity 85; e) a calibration fluid pouch nest 96; f) a calibration fluid pouch spike 99; and g) blood storage groove conduit 52. Shown in FIG. 2F is a detailed view of the detail F of the cartridge 10 shown in FIG. 2A, providing additional details of the cartridge inlet 43. Shown in FIG. 2G is a perspective view of the cartridge 10 shown in FIG. 2A, and shown in FIG. 2H is a detailed view of the detail H of the cartridge 10 shown in FIG. 2G. The details of the cartridge inlet of a first embodiment of a cartridge identified in FIGS. 2F and 2H are as follows: a) an annular surface at the top of the cartridge inlet; b) a recess in the annular surface 46 of the cartridge inlet; c) a blood storage conduit entrance 51; d) an air bladder exit port 88; and e) an internal wall of the cartridge inlet 43.

In some embodiments (not shown), one or more of the internal wall 48 and the external wall 49 comprise threads for engaging a cap and/or a syringe and/or a capillary adaptor. The threads are optionally designed to function as Luer locks. The perspective view in FIG. 2G is shown absent the flexible member 40 in order to reveal the air bladder window 86, and shown absent the flexible member 50 in order to reveal the calibration fluid pouch 94 and the calibration fluid pouch window 95.

A portion of the biosensor conduit 78 (hidden view) is defined by the biosensor conduit groove 79, the active area 81 (see FIG. 10E) of the biosensor array 80 in the biosensor array section, and gasket cut-out 107, which exposes the active area of the biosensor array to blood and calibration fluid. A person of ordinary skill in the art will appreciate that although the term array is used to describe specific examples of cartridges, a single biosensor is within the scope of the invention, and sometimes reference is made to the active area of the biosensor instead of the active area of the biosensor array. Usually, the active areas of the biosensors, for example the ion-selective membrane of a pH electrode (or pH biosensor), are exposed in the biosensor conduit, and the other components of the biosensor may not be exposed in the biosensor conduit. The gasket around the cut-out 107 prevents liquid from coming into contact with other areas (i.e., the non-active area) of the biosensor array. The biosensor array is attached to the second housing member 30 in the biosensor receptacle 83, by for example, an adhesive. Some embodiments (not shown) of the cartridge 10 comprises a biosensor conduit groove in the second housing member 20, underneath the biosensor array. Also, some embodiments (not shown) of the cartridge 10 comprises a biosensor receptacle in the first housing member 20, and a biosensor conduit groove in the second housing member 30. Other forms of biosensor receptacles are illustrated in other embodiments of the cartridge Also in the embodiments provided as examples, the biosensor electrical contact 82 (see FIG. 2A) is shown at the top of the biosensor array 80, but is should be understood that the electrical contacts can be located at the underside of the biosensor array, as disclosed in U.S. Pat. No. 7,094,330.

Figure 3A:
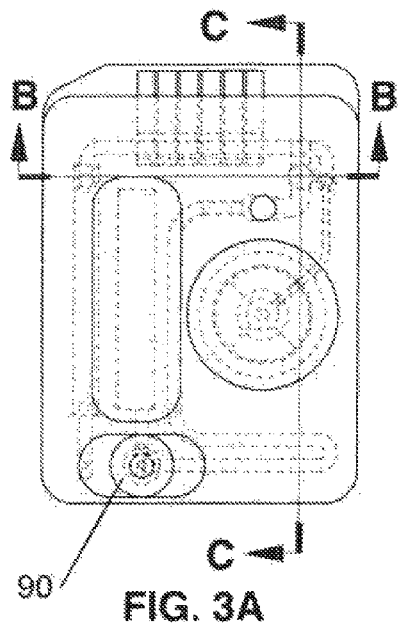
FIG. 3A is a schematic drawing showing details of a top view of the cartridge shown in FIG. 1A, with a syringe engaged at the cartridge inlet 43.
Figure 3B:
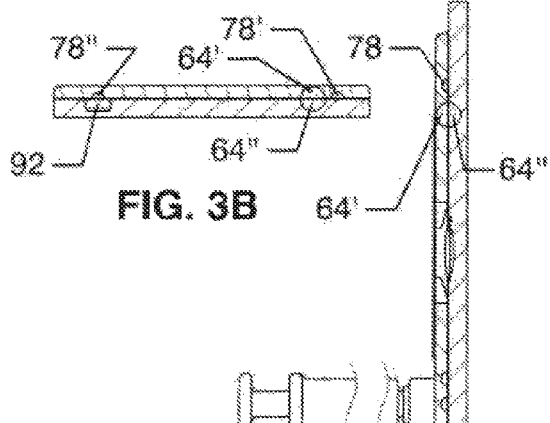
FIG. 3B is a first cross-sectional view through the cartridge shown in FIG. 3A along line B-B.
Figure 3C:
FIG. 3C is a second cross-sectional view through the cartridge shown in FIG. 3A along line C-C, and a broken right side view of the syringe.
Figure 3D:
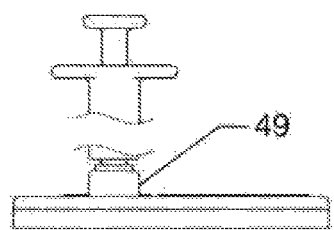
FIG. 3D is a front view of the cartridge and a broken front view of the syringe shown in FIG. 3A.
Figure 3E:
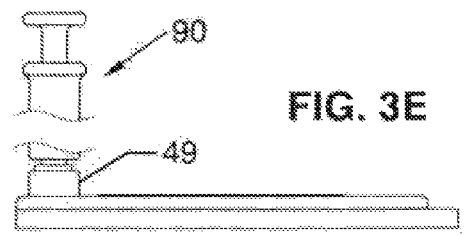
FIG. 3E is a right side view of the cartridge and a broken right side view of syringe shown in FIG. 3A.
Figure 3F:
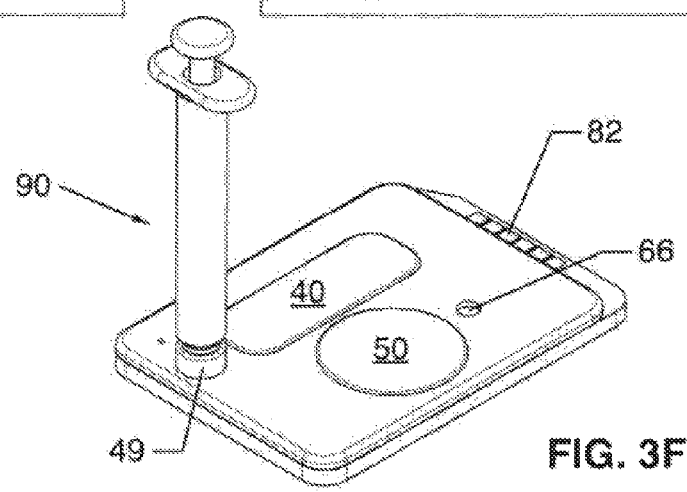
FIG. 3F is a perspective view of the cartridge and syringe shown in FIG. 3A.

Shown in FIG. 3A is a schematic drawing showing details of a top view of a spectroscopic and biosensor cartridge 10 for use with a joint-diagnostic spectroscopic and biosensor analyzer according to the first embodiment of the cartridge, with a syringe 90 engaged at the cartridge inlet 43. This embodiment of a cartridge was shown previously in FIG. 1 to FIG. 2G, absent any attachment to the cartridge inlet 43. Shown in FIG. 3B is a cross-sectional view through the cartridge 10 shown in FIG. 3A along line B-B, providing the following details: a) the proximal end of the biosensor conduit 78'; b) the distal end of the biosensor conduit groove 78"; c) a waste receptacle 92; d) a portion of the enlarged cavity 64' in the first housing member; and e) a portion of the enlarged cavity 64" in the second housing member. The portions 64' and 64" of the enlarged cavity 64 and the biosensor conduit 78 are also shown in FIG. 3C, a cross-sectional view through the cartridge 10 shown in FIG. 3A along line C-C. Shown in FIG. 3D, FIG. 3E and FIG. 3F are a front view, a right side view, and a perspective view respectively, of the cartridge 10 and a syringe 90, shown in FIG. 3A. The cartridge inlet 43 is not identified, but its external wall 49 is identified.

Shown in FIG. 4A is a schematic drawing showing details of a top view of the same cartridge 10, having a capillary adaptor 70 engaged at the cartridge inlet 43. Shown in FIG. 4B is a first cross-sectional view through the cartridge 10 shown in FIG. 4A along line B-B. Shown in FIG. 4C is a second cross-sectional view through the cartridge 10 and the capillary adaptor 70 shown in FIG. 4A along line C-C. Shown in FIG. 4D is a detailed view of detail D of the cartridge 10 shown in FIG. 4B, showing the first optical window 66, the second optical window 67, and the optical chamber 57. Shown in FIGS. 4E and 4G are a front view and a perspective view respectively, of the cartridge 10 with capillary adaptor 70 engaged with the cartridge inlet 43 shown in FIG. 4A. Shown in FIG. 4F is a detailed view of detail F of the cartridge 10 and capillary adaptor 70 shown in FIG. 4C. Shown in FIG. 4H is a perspective view of the capillary adaptor 70, providing the following details: a) a capillary adaptor inlet member 71; b) a capillary adaptor inlet port 72; c) a capillary adaptor lumen 73 (hidden view); d) a capillary adaptor handgrip 74; e) a capillary adaptor outlet member 75; and f) a capillary adaptor outlet port 76. Shown in FIG. 4F are the following details: a) the capillary adaptor outlet port 76 mating with the blood storage conduit entrance 51, whereby the lumen 73 can function as an extension of the blood storage conduit 52; b) an air bladder conduit 87; c) an air bladder exit port 88; d) the external wall 49 of the cartridge inlet 43; and e) a recess 47 in the annular surface 46 of the cartridge inlet 43 (see FIG. 2H), for keeping the exit port 88 open even when a cap 60 (see FIGS. 5A-5H) is engaged for sealing the cartridge inlet 43. In the capillary adaptor embodiment 70, the outlet member 75 is configured as the male end of syringe 90. In some embodiments (not shown), the outlet member 75 comprise threads, which are optionally designed to function as Luer locks.

Shown in FIG. 5A is a schematic drawing showing details of a top view of the same cartridge 10, having a cap 60 engaged at the cartridge inlet 43. Shown in FIG. 5B is a first cross-sectional view through the cartridge 10 and cap 60 shown in FIG. 5A along line B-B. Shown in FIGS. 5C, 5D and 5H are a right side view, a front view, and a perspective view respectively of cartridge and cap shown in FIG. 5A. Shown in FIG. 5F is a second cross-sectional view through the cartridge and cap shown in FIG. 5C along line F-F. Shown in FIG. 5E is a perspective view of an embodiment of a cap 60, showing the underside 62 and the cap internal wall surface 61. Shown in FIG. 5G is a detailed view of the detail G of the cartridge and cap shown in FIG. 5B, showing the following: a) the blood storage conduit entrance 51; b) the underside 62 of cap 60; c) the air bladder conduit 87; d) the air bladder exit port 88; and e) the recess 47 in annular surface of the cartridge inlet. In this embodiment, the cap internal wall surface 61 is frictionally engaged with the external wall 49 of the cartridge inlet 43 (see FIG. 2B). In other cartridge and cap embodiments, more optional details are provided, and their functions are explained.

Figure 6A:
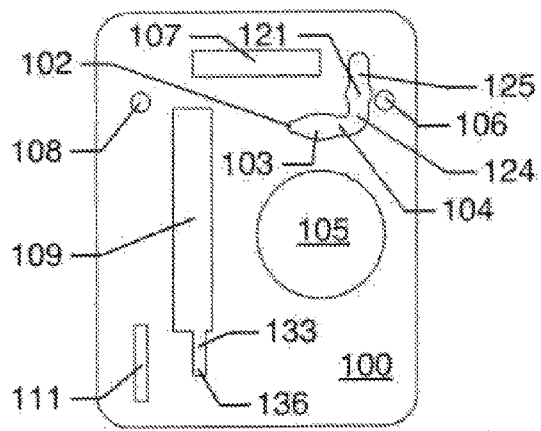
FIG. 6A is a top view of a gasket 100 of a first embodiment of the cartridge shown in FIG. 1A.
Figure 6B:
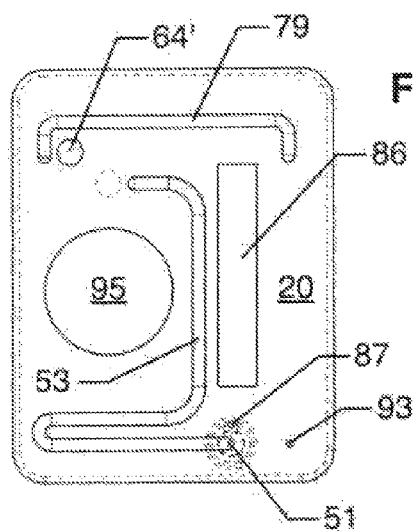
FIG. 6B is a bottom view of a first housing member 20 of a first embodiment of the cartridge shown in FIG. 1A.
Figure 6C:
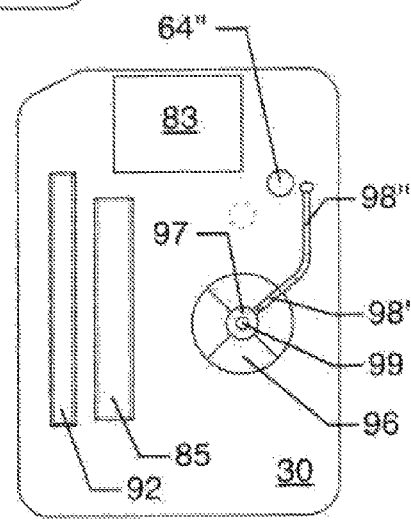
FIG. 6C is a top view of a second housing member 30 of a first embodiment of the cartridge shown in FIG. 1A.
Figure 6D:
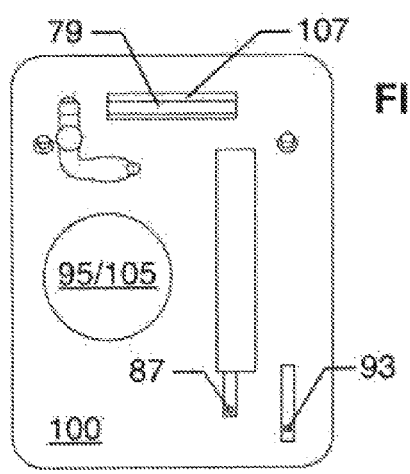
FIG. 6D is a bottom view of the first housing member 20 of the cartridge as shown in FIG. 6B, overlaid by and in alignment with the gasket 100 shown in FIG. 6A.
Figure 6E:
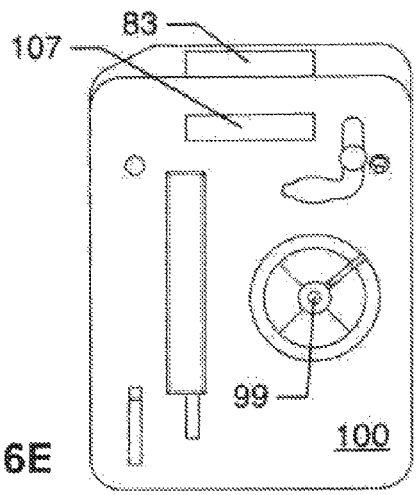
FIG. 6E is a top view of the second housing member 30 of the cartridge as shown in FIG. 6C, overlaid by and in alignment with the gasket shown 100 in FIG. 6A.

Shown in FIG. 6A is a top view of the gasket 100 of cartridge 10 shown in FIG. 1. The gasket cut-outs are numbered, and a brief description of each cut-out is provided in Table 1. Shown in FIG. 6B is a bottom view of the first housing member 20 of cartridge 10, and shown in FIG. 6C is a top view of the second housing member 30 of cartridge 10 shown in FIG. 1. FIGS. 6B and 6C can be visualized as the two housing members of cartridge 10, opening like a book. Shown in FIG. 6D is a bottom view of the first housing member of cartridge 10 shown in FIG. 6B, with the gasket 100 overlaid and aligned with the first housing member 20. Shown in FIG. 6E is a top view of the second housing member of cartridge 10 shown in FIG. 6C, with the gasket 100 overlaid and aligned with the second housing member 30.

Figures 7A, 7B, 7C:
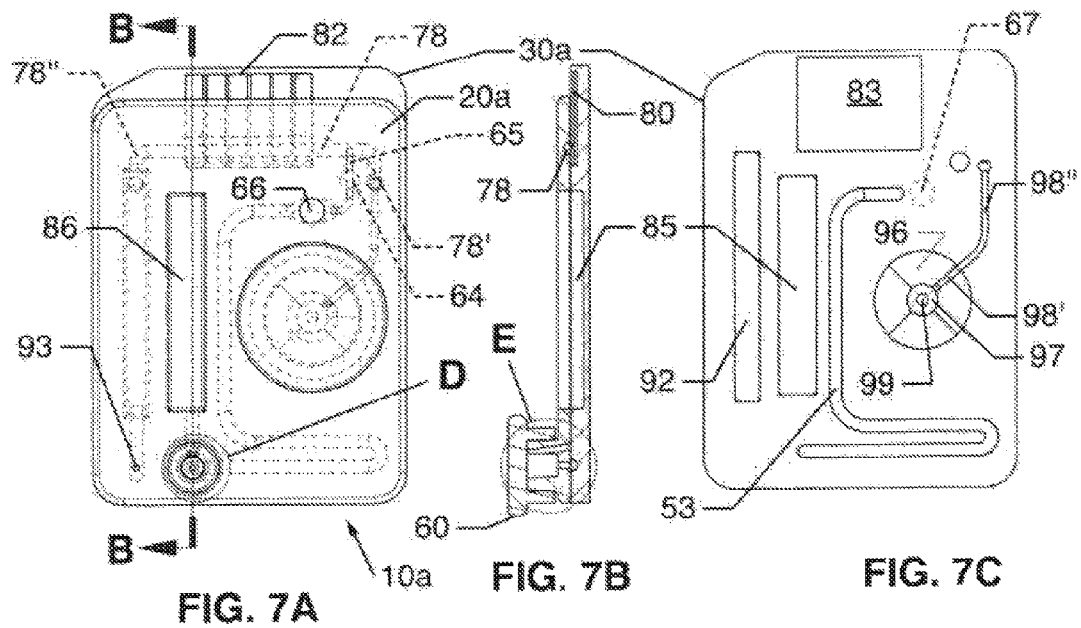
FIG. 7A is a schematic drawing showing details of a top view of a spectroscopic and biosensor cartridge 10a for use with a joint-diagnostic spectroscopic and biosensor analyzer, according to a second embodiment of the cartridge.
FIG. 7B is a cross-sectional view through the cartridge shown in FIG. 7A along line B-B.
FIG. 7C is a top view of the second housing member 30a of the cartridge shown in FIG. 7A, absent the biosensor array and the calibration fluid pouch.
Figures 7D, 7E:
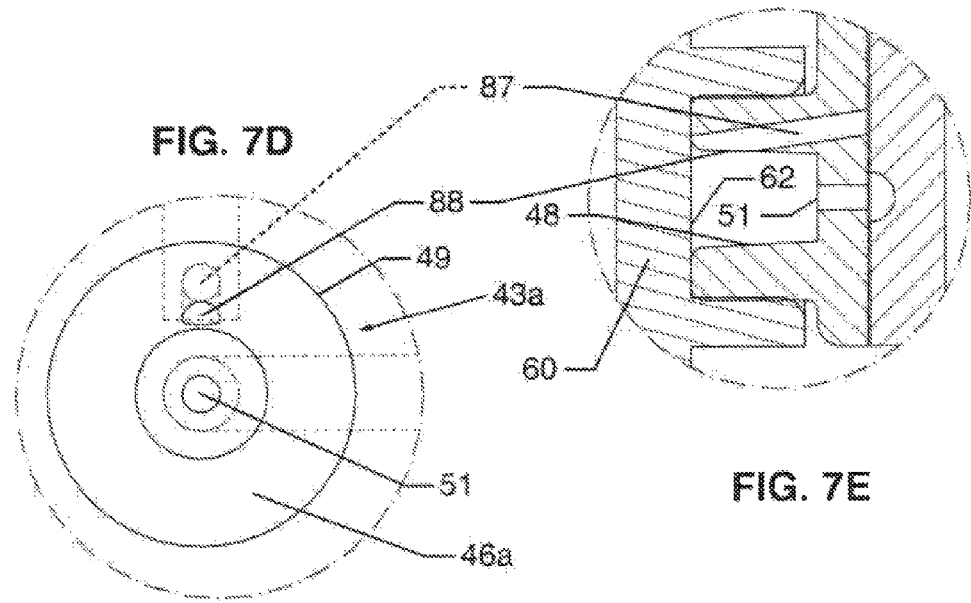
FIG. 7D is a first detailed view of the detail D of the cartridge shown in FIG. 7A.
FIG. 7E is a second detailed view of the detail E of the cartridge shown in FIG. 7B.

Shown in FIG. 7A is a schematic drawing showing details of a top view of a spectroscopic and biosensor cartridge 10a for use with a joint-diagnostic spectroscopic and biosensor analyzer according to a second embodiment of the cartridge. FIG. 7B is a cross-sectional view through the cartridge 10a shown in FIG. 7A along line B-B. FIG. 7C is a top view of the second housing member of the cartridge 10a shown in FIG. 7A, with the biosensor array and the calibration fluid pouch absent. FIG. 7D is a first detailed view of the detail D of the cartridge 10a shown in FIG. 7A. FIG. 7E is a second detailed view of the detail E of the cartridge 10a shown in FIG. 7B.

The cartridge 10a illustrated collectively in FIGS. 7A-7E is similar to the cartridge 10 illustrated collectively in FIG. 1 to FIG. 6E, and accordingly, elements common to them share common reference numerals. For some elements, the letter "a" is appended to the end of the reference numerals, in order to indicate that the elements are part of the second embodiment of the cartridge. A first difference between the first (10) and second (10a) embodiments of cartridges is that the blood storage conduit grooves 53 is disposed in the second housing member 30a instead of the first housing member 20a. A second difference is the absence of recess 47 in the annular surface 46a of the cartridge inlet 43a; the annular surface in the first embodiment comprises a recess 47 (shown in FIGS. 2F and 2H). Due to the absence of a recess like 47 in annular surface 46b, the annular surface 46a can mate with underside 62 of cap 60 to make an air-tight seal, when the cap 60 is frictionally engaged with the cartridge inlet 43a. As mentioned previously, for the first embodiment, the cap internal wall surface 61 forms a seal with the external wall 49 of the cartridge inlet 43 (see FIGS. 2B and 5G). A recess is not required in annular surface 46a because the air bladder conduit 87 is angled as shown in FIGS. 7D and 7E. Consequently, the air bladder exit port 88 is disposed substantially in the internal wall 48 of the cartridge inlet 43. Even when the cartridge inlet 43 is properly sealed with the cap 60 at the interface of the annular surface 46a and the underside 62 of the cap 60, fluid connection between the air bladder exit port 88 and the blood storage conduit entrance 51 is maintained.

The first and second embodiments of the disposable cartridge comprise gaskets 100 with similar cut-outs as shown in FIGS. 6A and 8A. Other cartridge embodiments use similar first and second housing members, and gaskets with different cut-outs, as shown collectively in FIGS. 8B-8D. Shown in FIG. 8A is a top view of a second embodiment of a gasket 100a. Shown in FIG. 8B is a top view of a third embodiment of a gasket 100a'. Shown in FIG. 8C is a top view of a fourth embodiment of a gasket 100a". Shown in FIG. 8D is a top view of a fifth embodiment of a gasket 100a'''. A brief description of the gasket cut-outs is provided in Table 1.

A third embodiment of a spectroscopic and biosensor cartridge 10b for use with a joint-diagnostic spectroscopic and biosensor analyzer is illustrated in FIG. 9A as an exploded view. Shown in FIG. 9B is a detailed view of the underside of the first housing member 20b shown in FIG. 9A, to illustrate the differences with the first embodiment (see FIG. 6B). The cartridge 10b illustrated collectively in FIGS. 9A-9B is similar to the cartridge 10 illustrated in FIG. 1, and accordingly, elements common to them share common reference numerals. For some elements, the letter "b" is appended to the end of the reference numerals, in order to indicate that the elements are part of the third embodiment of a cartridge. A first difference between the first and third embodiments of cartridge 10 is the addition of a blood shunt 54 (also identified in FIG. 10F with respect to a fourth embodiment of a cartridge 10c). The blood shunt is a tunnel having a first open end and beginning at the distal end of the blood storage conduit 52", and having a second open end and terminating at the optical chamber overflow chamber 59. In some embodiments of a cartridge, for example the seventh embodiment of a cartridge illustrated collectively in FIGS. 13A-13R the blood shunt 54f is a tunnel having a blood shunt slit 454 along the length of the tunnel, adjacent to the optical chamber, and providing fluid communication between the blood shunt 54f and the optical chamber, wherein the width of the blood shunt slit 454 is approximately equal to the optical chamber depth. In some embodiments, the length of the slit is less than the length of the blood shunt, and some embodiments comprise more than one slit, wherein the sum of the lengths of the slits is less than the length of the blood shunt (not shown).

A second difference is in the gasket 100b of cartridge 10b. A third difference is the addition of a connecting groove 65 in the first housing member 20b of cartridge 10b, positioned to provide fluid connection between an enlarged cavity 64 and a biosensor conduit 79.

The addition of a blood shunt 54 provides the advantage of increasing blood flow into the biosensor conduit 78 by bypassing the optical chamber, when the optical chamber depth, which defines the direct optical pathlength, is at the lower limit of the approximate range of about 50 microns to about 200 microns. In use, blood is allowed to flow until it reaches the enlarged cavity 64. By stopping blood flow at this time, the optical chamber becomes filled if it is not already full, because of capillary action in the shallow optical chamber. As an example, the volume of a spherical enlarged cavity is in the approximate range of about 10 to 35 microliters. In some embodiments of the cartridge, the volume of the optical chamber is in the approximate range of about 0.5 to about 10 microliters. Therefore in some embodiments, the blood storage conduit stores greater than 90% of the blood received by the cartridge, during spectroscopic measurement of the blood. It should be understood that the term analyzing a sample is sometimes referred to as testing a sample or measuring a sample.

Some other non-limiting examples of functions of the optional blood shunt are as follows: i) maintaining blood flow to the biosensor conduit, in case the optical chamber becomes plugged with fibrin strands; and ii) mitigating hemolysis that may occur when blood is squeezed through the optical chamber having a depth that is substantially smaller than the luminal diameter of a needle use to draw blood from a patient. The optical depth dimension is preferably in an approximate range of about 50 microns to about 200 microns. In comparison, the internal diameter of a 21-gauge needle, which is considered to be a fine needle for drawing blood from a patient, is about 500 microns. It is well known that hemolysis is more likely when blood is drawn using a needle having a small bore compared with blood drawn with a needle having larger bore. Therefore there are advantages to avoid forcing the blood through the optical chamber in order to get the blood to the biosensor conduit.

A spectroscopic and biosensor system comprising a cartridge 10c and a cap 60c, for use with a joint-diagnostic spectroscopic and biosensor analyzer, according to a fourth embodiment of the cartridge, are Illustrated collectively in FIG. 10A to FIG. 10U. The elements in cartridge 10c and cap 60c are similar to the previously described cartridge and cap, and accordingly, elements common to them share common reference numerals. For some elements, the letter "c" is appended to the end of the reference numerals, in order to indicate that the elements are part of a fourth embodiment of the cartridge. A brief description of the elements is provided in Table 1. A first difference in cartridge 10c is that paddle 150c is hingedly attached to the first housing member 20c, with a hinge 151c. A second difference is the inclusion of a second enlarged cavity 68, for creating an air bubble, in case blood fills the first enlarged cavity 64. A third difference is an air bladder cavity that is defined by a cavity 85 in the first housing member 20c, having an air bladder window 86. A fourth difference is a single laminate 31c that covers both the air bladder cavity 85 and the paddle 150c. A fifth difference is the snap fit lip 41c (shown as a chamfer) of cartridge inlet 43c. The cap 60c comprises a discontinuous annular snap fit 42c and a pressure release groove 63c for frictionally engaging the cap, whereby the blood in the blood storage conduit is not pushed when the cap is engaged with the cartridge inlet. This feature is useful with a capillary adaptor 70, and a piston assembly 400 for the capillary adaptor 70 (see FIGS. 13F-13N), whereby the piston assembly is used to sufficiently urge the blood in the blood storage conduit, so that the atmosphere-contaminated leading edge of the blood is displaced from the optical chamber.

A seventh difference is the recess 47c in the annular surface 46c of the cartridge inlet 43c. Note that the recess 47c does not render the annular surface 46c completely discontinuous, as is the case of the recess 47 illustrated in FIGS. 2F and 2H. In the fourth embodiment of a cartridge, the underside 62c of cap 60c mates with the annular surface 46c of the cartridge inlet 43c, sealing the cartridge inlet 43c.

The snap fit lip 41c (shown as a chamfer) of cartridge inlet 43c allows the cap to be engaged with the cartridge inlet, whereby the annular snap fit element 45c of the cartridge 10c mates with an annular snap fit seal 42d (no pressure release groove 63c required) of a cap 60d (see FIGS. 11S & 11U), creating a sealed cartridge inlet 43c. Because of the chamfer in the snap fit lip 41c, no substantial force is applied to the blood in the blood storage conduit. A person of ordinary skill will appreciate that as the lip becomes wider (along the height dimension of the cartridge), for example the lip 41d shown in FIG. 11N, there is more force applied to the blood in the blood storage conduit; the lip acts as a plunger having a stroke equivalent to the width of the lip 41d. The lip 41c is like an edge, having substantially no width dimension (along the height of the cartridge inlet). Although some embodiments of cartridges are illustrated with caps, it will be appreciated that these are just examples and the caps shown can be used with one or more cartridge embodiments.

Shown in FIG. 10A is an exploded view of the cartridge 10c and cap 60c. Shown in FIG. 10B is a bottom view of the first housing member 20c of the cartridge shown in FIG. 10A. Shown in FIG. 10C is a bottom view of the first housing member 20c shown in FIG. 10B, overlaid by and in alignment with the gasket 100c shown in FIG. 10A. Shown in FIG. 10D is a top view of the second housing member 30c of the cartridge shown in FIG. 10A. Shown in FIG. 10E is a top view of the second housing member 30c shown in FIG. 10D (including the biosensor array 80 and calibration fluid pouch 94 shown in FIG. 10A), overlaid by and in alignment with the gasket 100c shown in FIG. 10A. Shown in FIG. 10F is a top view of the cartridge shown in FIG. 10A, with a cap 60c engaged with cartridge inlet 43c. Shown in FIG. 10G is a right side view of the cartridge and cap shown in FIG. 10F. Shown in FIG. 10H is a bottom view of the cartridge and cap shown in FIG. 10F. Shown in FIG. 10J is a first cross-sectional view through the cartridge and cap shown in FIG. 10F along line J-J. Shown in FIG. 10K is a second cross-sectional view through the cartridge shown in FIG. 10F along line K-K. Shown in FIG. 10L is a third cross-sectional view through the cartridge shown in FIG. 10H along line L-L. Shown in FIG. 10M is a fourth cross-sectional view through the cartridge and cap shown in FIG. 10H along line M-M. Shown in FIG. 10N is a first detailed view of the detail N of the cartridge shown in FIG. 10M, absent the cap 60c.

Shown in FIG. 10P is a perspective view of the cartridge shown in FIG. 10A, absent the cap 60c. Shown in FIG. 10Q is a front view of the cap 60c shown in FIG. 10A. Shown in FIG. 10R is a second detailed view of the detail R of the cartridge shown in FIG. 10P, showing details of the cartridge inlet 43c. Shown in FIG. 10S is a bottom view of the cap 60c shown in FIG. 10Q. Shown in FIG. 10T is a cross-sectional view through the cap 60c shown in FIG. 10S along line T-T. Shown in FIG. 10U is a perspective view of the cap 60c shown in FIG. 10Q.

The fourth embodiment of a cartridge inlet 43c comprises: a) an external wall 49; b) an annular surface 46c at the top of the inlet 43c; c) a recess 47c in the annular surface 46c; d) a snap fit lip 41c having a chamfer; e) an annular snap fit element 45c. The cap 60c used to seal the cartridge inlet 43c comprises: i) an internal wall surface 61c; b) a pressure release groove 63c in the internal wall 61c, ii) a flat underside 62c for mating with the annular surface 46c of the cartridge inlet 43c; and iii) a discontinuous annular snap fit element 42c. When the cap 60c is engaged with the cartridge inlet 43c, the blood in the blood storage conduit is not pushed away from the blood storage conduit entrance because of the pressure release groove 63c, which makes the annular snap fit element 42c discontinuous. In other similar embodiments, the annular snap fit element is segmented, having two or more segments for locking the cap with the inlet. The cartridge annular surface 46c mates with the flat underside 62c of the cap 60c, to create a seal. It should be noted that the recess 47c does not make the annular surface 46c discontinuous, compared with the annular surface 46 and recess 47 illustrated in FIG. 2H. In the latter case, the annular surface 46 is discontinuous due to the recess 47.

A spectroscopic and biosensor system comprising a cartridge 10d and a cap 60d, for use with a joint-diagnostic spectroscopic and biosensor analyzer, according to a fifth embodiment of the cartridge, are Illustrated collectively in FIG. 11A to FIG. 11Z. The elements in cartridge 10d and cap 60d are similar to the fourth embodiment of a cartridge and cap, and accordingly, elements common to them share common reference numerals. For some elements, the letter "d" is appended to the end of the reference numerals, in order to indicate that the elements are part of a fifth embodiment of the cartridge. A brief description of the elements is provided in Table 1. A first difference is that the air bladder window 86 is disposed in the second housing member 30d of the cartridge. A second difference is that the paddle 150d is disposed in the second housing member 30d of the cartridge. A third difference is that the biosensor receptacle 83 in the fourth embodiment of a cartridge is replace with a cut-out ledge 84, for facilitating heating of the sensor array; in this embodiment, the sensor array slides over a heating element located in the analyzer 310 shown FIG. 14A as an example (no heating element shown). A fourth difference is that the cartridge comprises a second enlarged cavity 68 in a substantially rectangular sectional shape as shown in FIG. 11B and FIG. 11D, and the enlarged cavities 64 and 68 are fluidly connected by an interconnecting groove 69, disposed in the second housing member 30d of the cartridge. A fifth difference is that the calibration fluid pouch 94d for storing and releasing calibration fluid, comprises a frangible seal, whereby a spike 99 shown in FIG. 10A is not required for releasing the calibration fluid. Details of the calibration fluid pouch 94d are provided collectively in FIG. 11V to FIG. 11Z.

Figure 11F:
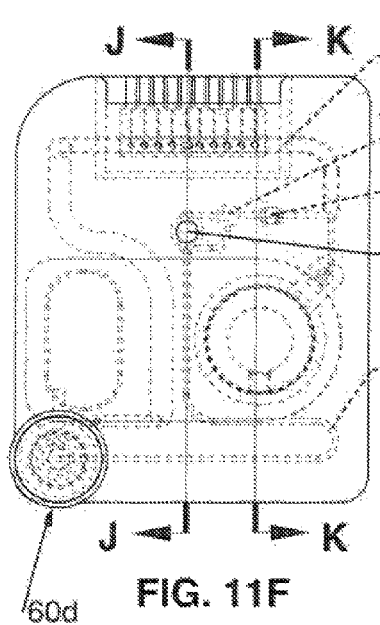
FIG. 11F is a top view of the cartridge 10d shown in FIG. 11A, with the cap 60d engaged at the cartridge inlet 43d.
Figure 11G:
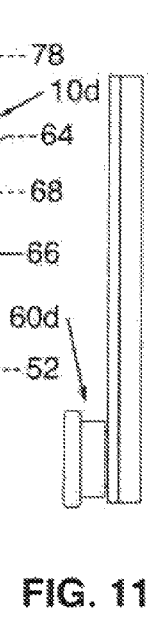
FIG. 11G is a right side view of the cartridge and cap shown in FIG. 11F.
Figure 11H:
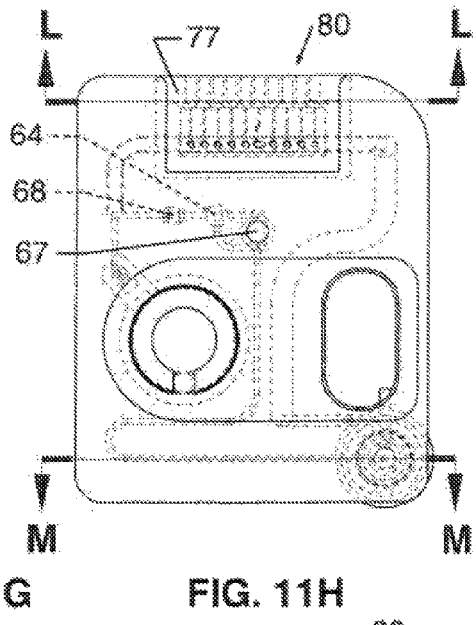
FIG. 11H is a bottom view of the cartridge and cap shown in FIG. 11F.
Figure 11L:
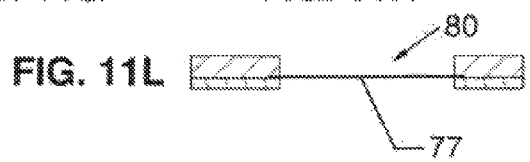
FIG. 11L is a third cross-sectional view through the cartridge shown in FIG. 11H along line L-L.
Figures 11J, 11K:
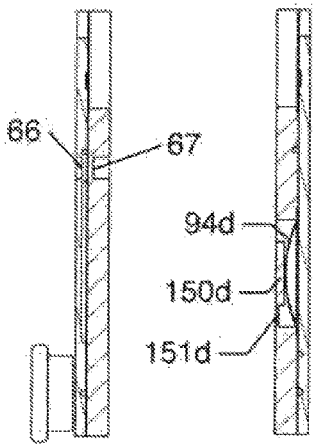
FIG. 11J is a first cross-sectional view through the cartridge shown in FIG. 11F along line J-J.
FIG. 11K is a second cross-sectional view through the cartridge shown in FIG. 11F along line K-K.
Figure 11M:
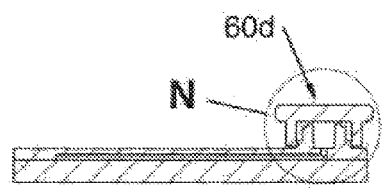
FIG. 11M is a fourth cross-sectional view through the cartridge and cap shown in FIG. 11H along line M-M.
Figure 11N:
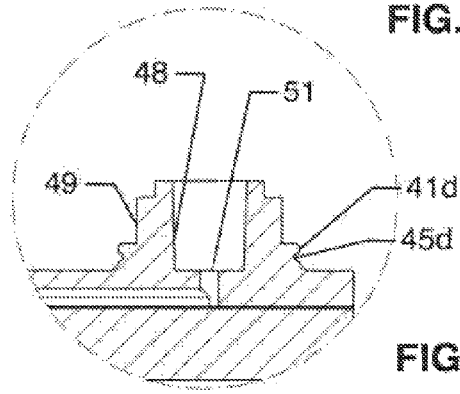
FIG. 11N is a first detailed view of the detail N of the cartridge shown in FIG. 11M, absent the cap 60d.

Shown in FIG. 11A is an exploded view of the spectroscopic and biosensor cartridge 10d and cap 60d for use with a joint-diagnostic spectroscopic and biosensor analyzer, according to a fifth embodiment of the cartridge. Shown in FIG. 11B is a bottom view of the first housing member 20d of the cartridge shown in FIG. 11A. Shown in FIG. 11C is a bottom view of the first housing member 20d shown in FIG. 11B, overlaid by and in alignment with the gasket 100d shown in FIG. 11A. Shown in FIG. 11D is a top view of the second housing member 30d of the cartridge shown in FIG. 11A. Shown in FIG. 11E is a top view of the second housing member 30d shown in FIG. 11D (including the biosensor array 80 shown in FIG. 11A), overlaid by and in alignment with the gasket 100d shown in FIG. 11A. Shown in FIG. 11F is a top view of the cartridge shown in FIG. 11A, with a cap 60d engaged at the cartridge inlet 43d. Shown in FIG. 11G is a right side view of the cartridge and cap shown in FIG. 11F. Shown in FIG. 11H is a bottom view of the cartridge and cap shown in FIG. 11F. Shown in FIG. 11J is a first cross-sectional view through the cartridge shown in FIG. 11F along line J-J. Shown in FIG. 11K is a second cross-sectional view through the cartridge shown in FIG. 11F along line K-K. Shown in FIG. 11L is a third cross-sectional view through the cartridge shown in FIG. 11H along line L-L. Shown in FIG. 11M is a fourth cross-sectional view through the cartridge and cap shown in FIG. 11H along line M-M. Shown in FIG. 11N is a first detailed view of the detail N of the cartridge shown in FIG. 11M, absent the cap 60d, showing details of the cartridge inlet 43d. Shown in FIG. 11P is a perspective view of the cartridge shown in FIG. 11A, absent the cap 60d. Shown in FIG. 11R is a second detailed view of the detail R of the cartridge shown in FIG. 11P, showing more details of the cartridge inlet 43d. Shown in FIG. 11S is a front view of the cap 60d shown in FIGS. 11A and 11F. Shown in FIG. 11T is a bottom view of the cap 60d shown in FIG. 11S. Shown in FIG. 11U is a perspective view of the cap 60d shown in FIG. 11S. Shown in FIG. 11V is a top view of a calibration fluid pouch 94d having a frangible seal 205. Shown in FIG. 11W is a front view of the calibration fluid pouch 94d shown in FIG. 11V. Shown in FIG. 11X is a bottom view of the calibration fluid pouch 94d shown in FIG. 11V. Shown in FIG. 11Y is a cross-sectional view of the calibration fluid pouch 94d shown in FIG. 11V along line Y-Y. Shown in FIG. 11Z is a detailed view of the detail Z of the calibration fluid pouch 94d shown in FIG. 11Y.

The fifth embodiment of the cartridge inlet 43d comprises: a) an external wall 49; b) an internal wall 48; c) an annular surface 46d at the top of the inlet 43d; d) a recess 47d in the annular surface 46d; e) a snap fit lip 41d disposed in the external wall 49 of the cartridge inlet 43d; f) a snap fit seal element 45d in the external wall 49 of the cartridge inlet 43d. The cap 60d comprises: i) an internal wall surface 61d; ii) an annular snap fit seal 42d for frictionally engaging the cap and creating a seal at the interface of the snap fit seal element 45d of the cartridge inlet and the annular snap fit seal 42d of the cap 60d. The snap fit lip 41d is sufficiently wide (along the height of the cartridge inlet) for frictionally engaging the cap sufficiently to displace atmosphere-contaminated leading end of the blood sample from the optical chamber. For comparison, the snap fit lip 41c shown in FIG. 10N is shown as an edge, i.e., a lip with substantially no width dimension. Also, at least the top portion of the cap is sufficiently rigid to prevent rebounding of the top portion of the cap when the cap is released, whereby avoiding the formation of suction that could cause regurgitation of the blood. The recess 47d in the annular surface 46d provides access to the air bladder exit port 88, whereby when the cap 60d is properly engaged with the cartridge inlet 43d, the air bladder exit port 88 becomes fluidly connected with the blood storage conduit entrance 51.

The systems described before provide several examples of interaction between the cartridge inlet 43 and the cap 60, for providing various functions. In one system the cartridge inlet comprises: a) a snap fit lip disposed in the external wall of the cartridge inlet; b) a snap fit seal element in the external wall of the cartridge inlet; and c) an annular surface at the top of the cartridge inlet. The annular surface comprises a recess. The cap comprises: i) an internal wall having an annular snap fit seal for frictionally engaging the cap and creating a seal at the interface of the snap fit seal element of the cartridge inlet and the annular snap fit seal of the cap; and ii) at least the top portion of the cap is sufficiently rigid to prevent rebounding of the top portion of the cap when the cap is released. The snap fit lip is sufficiently wide for frictionally engaging the cap sufficiently to displace atmosphere-contaminated leading end of the blood sample from the optical chamber. The rigid cap top prevents the formation of suction that could cause regurgitation of the blood.

In another system, the cartridge inlet comprises an annular surface at the top of the cartridge inlet, and the cap comprises a flat underside for mating with the annular surface of the cartridge inlet for sealing the cartridge inlet. The cap further comprises an internal wall surface for frictionally engaging the cap, and the cap internal wall comprising a pressure release groove, whereby when the cap is engaging with the cartridge inlet, the blood in the blood storage conduit is not pushed away from the blood storage conduit entrance.

In yet another system, the cartridge inlet further comprises one of a cartridge inlet top having an annular surface, and a cartridge inlet internal wall comprising at least a portion of the air bladder exit port. When the cap is properly engaged with the cartridge inlet for sealing the cartridge inlet, the air bladder exit port maintains fluid connectivity with the blood storage conduit entrance, but is sealed from the external atmosphere by the cap. In other words, the cap provides a pathway for pressurized air between the air bladder exit port and the blood storage conduit entrance.

Some systems further comprise a capillary adaptor for transferring blood from a punctured site of a body part of a patient, to a cartridge for testing. The capillary adaptor comprises: a) a capillary adaptor inlet member configured as a piece of a capillary tube, having a capillary adaptor inlet port for insertion into the blood sample; b) a capillary adaptor outlet member configured as the male end of a syringe; c) a capillary adaptor outlet port for substantially mating with the blood storage conduit entrance; d) a capillary adaptor lumen for fluidly connecting the capillary adaptor inlet port and the capillary adaptor outlet port; and e) a handgrip for handling the capillary adaptor. When the capillary adaptor is properly engaged with the cartridge inlet, the capillary adaptor lumen becomes an extension of the blood storage conduit. The system further comprising means for conserving blood trapped in the capillary adaptor lumen, the means comprising a piston assembly having a piston sized to slide into the capillary adaptor lumen, a head and a rod for connecting the piston and the head, and force applied to the head with the piston inside the lumen, whereby the force on the head pushes the trapped blood out of the capillary adaptor lumen through the blood storage conduit entrance. The system further comprises means for displacing the atmosphere-contaminated leading end of the blood sample from the optical chamber, whereby the optical chamber becomes occupied with blood that is protected from atmospheric contamination. The means comprises: i) the capillary adaptor lumen; ii) a piston assembly having a piston sized to slide into the capillary adaptor lumen; iii) a head and a rod for connecting the piston and the head; and iv) nd force applied to the head with the piston inside the lumen.

In another system, the cartridge inlet comprises an external wall surface and an inlet annular snap fit seal disposed at the external wall surface of the cartridge inlet, and the cap comprises an internal wall surface and a cap annular snap fit seal disposed at the internal wall surface of the cap for engaging with the inlet annular snap fit seal and for sealing the cartridge inlet at the interface of the inlet annular snap fit seal and the cap annular snap fit seal.

As an example, a disposable cartridge comprises: a) a housing; b) a cartridge inlet in the housing for receiving the blood sample; c) a blood storage conduit within the housing having a proximal end close to the cartridge inlet and a distal end away from the cartridge inlet; d) an optical chamber within the housing for receiving the blood from the distal end of the blood storage conduit and for measuring the at least two hemoglobin species, the optical chamber comprising an optical depth dimension orthogonal to the insertion plane; e) at least one optical window in the housing positioned to align with at least a portion of the optical chamber for collecting spectroscopic data from blood in that portion of the optical chamber; f) an optical chamber overflow chamber in fluid connection with the optical chamber for receiving blood from the optical chamber; g) a blood shunt for providing fluid connectivity between the distal end of the blood storage conduit and the optical chamber overflow chamber, the blood shunt having a maximum shunt depth dimension orthogonal to the insertion plane, and wherein the maximum shunt depth dimension is substantially larger than the optical chamber depth dimension, for a more efficient blood flow from the distal end of the blood storage conduit to the biosensor conduit; h) a biosensor conduit within the housing for receiving the blood from the optical chamber overflow chamber, the biosensor conduit having at least one biosensor for measuring the at least pH of the blood sample; i) an air bladder and an air bladder exit port within the housing for providing pressurized air for urging blood from the blood storage conduit into the biosensor conduit; j) a waste receptacle for receiving waste liquid from the biosensor conduit; and k) a waste receptacle vent for relieving pressure in the waste receptacle.

In some embodiments, the blood shunt further comprises a slit adjacent to the optical chamber, the slit having a length not greater than the length of the blood shunt and a slit width approximately equal to the optical depth. Since the optical chamber is vented via the waste receptacle vent, the slit facilitates flow of blood into the optical chamber. A spectroscopic and biosensor system comprising a cartridge 10*e*, for use with a joint-diagnostic spectroscopic and biosensor analyzer, according to a sixth embodiment of the cartridge, are Illustrated collectively in FIG. 12A to FIG. 12R. The elements in cartridge 10*e* are similar to elements in the fourth and fifth embodiments of a cartridge, and accordingly, elements common to them share common reference numerals. For some elements, the letter "e" is appended to the end of the reference numerals, in order to indicate that the elements are part of a sixth embodiment of the cartridge. A brief description of the elements is provided in Table 1. A first difference is that the calibration fluid pouch 94*e* comprises a bulging portion 196*e*, which comprises a first foil outer layer and a first polymer inner layer, and a flat portion 195*e*, which comprises a second foil outer layer and a second polymer inner layer. Details of the calibration fluid pouch 94e are provided in FIG. 12L to FIG. 12R. The first and second foil outer layers are similar, but the first polymer inner layer is substantially thicker than the second polymer inner layer. The first polymer inner layer is of sufficient thickness to allow formation of the bulging portion so as to protect the first foil outer layer from damage during the forming process. The second polymer inner layer is of sufficient thickness to allow bonding of the first and second polymer inner layers along the pouch flange 91e, thereby creating a perimeter seal, but thin enough to be easily pierced by a spike 99e. A second difference is the shape of the pouch nest 96e and the pouch spike recess 97e for housing the spike 99e, shown in FIG. 12A and FIG. 12M. The pouch nest 96e is substantially flat for mating with the pouch flange 91e comprising a perimeter seal. The tip of the pouch spike 99e is slightly below the pouch nest 96e so that the flat portion 195e of the pouch 94e is not accidentally pierced when the pouch 94e is assembled in the nest 96e. The recess 97e is preferably shaped like a bowl so as to minimize air trapped in the recess during activation of the paddle 150e. By pressing on the paddle 150e, the pressure exerted on the calibration fluid pouch causes the flat portion 195e to bulge sufficiently into the tip of the spike 99e, whereby the spike 99e pierces the flat portion 195e of the pouch 94e.

A third difference in the sixth embodiment of the cartridge is that the biosensor array comprises at least an oxygen biosensor for measuring $pO_2$, and a pH biosensor. A fourth difference in the sixth embodiment of the cartridge is the inclusion of a plurality of blind holes 215 at the roof in the biosensor conduit groove 79, of sufficient size and number, whereby sufficient air is trapped for equilibrating the atmospheric oxygen with the oxygen in the calibration fluid. By using calibration fluid equilibrated with atmospheric oxygen, and measuring the atmospheric pressure, the $pO_2$ in the calibration fluid can be determined at the time of calibration of an oxygen biosensor. Therefore, an embodiment of an analyzer used with cartridge 10e, comprises means for measuring atmospheric pressure. In the cartridge 10e, the plurality of blind holes 215 are disposed so that they are substantially close to the oxygen biosensor. Determination of a suitable volume of trapped air is disclosed in U.S. Pat. No. 5,614,416 to Lauks.

Shown in FIG. 12A is an exploded view of the spectroscopic and biosensor cartridge 10e for use with a joint-diagnostic spectroscopic and biosensor analyzer, according to a sixth embodiment of the cartridge. Shown in FIG. 12B is a bottom view of the first housing member 20e of the cartridge shown in FIG. 12A. Shown in FIG. 12C is a bottom view of the first housing member 20e shown in FIG. 12B, overlaid by and in alignment with the gasket 100e shown in FIG. 12A. Shown in FIG. 12D is a top view of the second housing member 30e of the cartridge shown in FIG. 12A. Shown in FIG. 12E is a top view of the second housing member 30e shown in FIG. 12D (including the biosensor array 80 and the calibration fluid pouch 94e shown in FIG. 12A), overlaid by and in alignment with the gasket 100e shown in FIG. 12A. Shown in FIG. 12F is a detailed view of the detail F of the cartridge shown in FIG. 12B, showing the plurality of blind holes 215. Shown in FIG. 12G is a right side view of the cartridge 10e shown in FIG. 12A. Shown in FIG. 12H is a back view of the cartridge 10e shown in FIG. 12G. Shown in FIG. 12J is a top view of the cartridge 10e shown in FIG. 12G. Shown in FIG. 12K is a perspective view of the cartridge 10e shown in FIG. 12A. Shown in FIG. 12L is a cross-sectional view through the cartridge shown in FIG. 12J along line L-L. Shown in FIG. 12M is a detailed view of the detail M of the cartridge shown in FIG. 12L. Shown in FIG. 12N is a top view of a calibration fluid pouch 94e shown in FIG. 12A. Shown in FIG. 12P is a front view of a calibration fluid pouch 94e shown in FIG. 12N. Shown in FIG. 12Q is a bottom view of a calibration fluid pouch 94e shown in FIG. 12N. Shown in FIG. 12R is a cross-sectional view through the calibration fluid pouch 94e shown in FIG. 12Q along line R-R, showing the calibration fluid pouch cavity 203e. Other examples of calibration fluid pouches are disclosed in U.S. Pat. No. 8,449,843 to Ade. Ade discloses a dimple on the bulged side of the pouch, as the puncture site. The dimple is supposed to protect the pouch from premature rupture by the spike in the cartridge. The pouch nest is not flat but contoured to fit the bulge side with the dimple.

In an embodiment 10e of a cartridge, the calibration fluid pouch comprises: a) a bulging side comprising a first foil outer layer and a first polymer inner layer; b) a flat side comprising a second foil outer layer and a second polymer inner layer; c) a flange comprising a perimeter seal for holding the bulging side and the flat side together; and c) a cavity between the bulging side and the flat side, created by the bulge and containing calibration fluid. The first polymer inner layer is of sufficient thickness to allow formation of a bulge in the bulging side, and the second polymer inner layer is of sufficient thickness to allow bonding of the first and second polymer inner layers so as to make a perimeter seal along the flange, but sufficiently thin for easy piercing to release the calibration fluid. This cartridge embodiment also comprises a substantially flat calibration fluid pouch nest 96e having a recess 97e disposed around the middle for housing a spike 99e. The spike 99e has a tip at the top for piercing the pouch. The flat side of the pouch 195e mates with the flat calibration fluid pouch nest 96e and the tip of the spike is sufficiently below the flat portion of the calibration fluid pouch nest, in order to protect the pouch from accidental puncture at the flat side 195e of the pouch, by the spike 99e.

A spectroscopic and biosensor system for use with a joint-diagnostic spectroscopic and biosensor analyzer, comprising a cartridge 10f according to a seventh embodiment of the cartridge, a capillary adaptor 70, and an embodiment of a piston assembly 400 for the capillary adaptor 70, are Illustrated collectively in FIG. 13A to FIG. 13R. The elements in cartridge 10f are similar to elements in the sixth embodiment of a cartridge, and accordingly, elements common to them share common reference numerals. For some elements, the letter "f" is appended to the end of the reference numerals, in order to indicate that the elements are part of a seventh embodiment of the cartridge. A brief description of the elements is provided in Table 1. A first difference is that the blood shunt 54f is a tunnel having a blood shunt slit 454 along the length of the tunnel, wherein the width of the blood shunt slit 454 is approximately equal to the thickness of the gasket 100f. The blood shunt slit 454 provides fluid communication between the blood shunt 54f, the optical chamber 57f, and the enlarged cavity 64. Since the enlarged cavity 64 is fluidly connected to the vent 93f via the waste receptacle 92f and the biosensor conduit 78f, a function of the blood shunt slit 454 is to enhance filling of the optical chamber. The optical chamber 57f, the enlarged cavity 64f and the blood shunt 54f substantially define a single compartment, illustrated in FIG. 13F (hidden view) in conjunction with the gasket cut out labeled as cut outs 102f, 103f, 104f and 121f in combination, shown in FIG. 13A. A second difference is that the blood storage conduit 52 is the lumen of a capillary tube 55f, which is nested in capillary tube grooves 53*f'* shown in FIG. 13B and 53*f''* shown in FIG. 13D. In this embodiment, the lumen of the capillary tube 55*f* is heparinized to mitigate early clotting of blood, and the capillary tube is preferably made of plastic, for example PETG (glycol modified polyethylene terephthalate), which should not be considered limiting in any way. A person of skill in the art will appreciate that "heparinized" implies a coating of heparin on the lumen of the capillary tube 55*f*, or deposition of either a fluff of lyophilized heparin or liquid heparin at the proximal end of the capillary tube. Regarding some plastics capillary tubes, more diffusion of gasses across the walls of tubes are observed, when compared to glass capillary tubes, but plastic provides safety advantages over glass, which can be broken easily. PETG is a plastic commonly used to make capillary tubes for blood gas analysis. The advantage of prefabricating the blood storage conduit in the form of a capillary tube 55*f*, is that there are more choices of plastic used to mold the cartridge housing members.

Shown in FIG. 13A is an exploded view of the spectroscopic and biosensor cartridge for use with a joint-diagnostic spectroscopic and biosensor analyzer, according to a seventh embodiment of the cartridge. Shown in FIG. 13B is a bottom view of the first housing member 20*f* of the cartridge shown in FIG. 13A. Shown in FIG. 13C is a bottom view of the first housing member 20*f* shown in FIG. 13B, overlaid by and in alignment with the gasket 100*f* shown in FIG. 13A. Shown in FIG. 13D is a top view of the second housing member 30*f* of the cartridge shown in FIG. 13A. Shown in FIG. 13E is a top view of the second housing member 30*f* shown in FIG. 13D (including the biosensor array 80 and calibration fluid pouch 94*f* shown in FIG. 13A), overlaid by and in alignment with the gasket 100*f* shown in FIG. 13A.

Shown in FIG. 13F is a top view of joint-diagnostic spectroscopic and biosensor system 450 showing an embodiment of a cartridge 10*f* shown collectively in FIGS. 13A-13E, and an embodiment of a piston assembly 400 shown in FIG. 13J for a capillary adaptor 70 shown in FIG. 4H. Shown in FIG. 13G is a first cross-sectional view through the system 450 shown in FIG. 13F along line G-G. Shown in FIG. 13H is a second cross-sectional view through the system 450 shown in FIG. 13F along line H-H. Shown in FIG. 13J is a front view of an embodiment 400 of a piston assembly for a capillary adaptor 70, showing a head 410, a piston 420, and a piston rod 415 that connects the head 410 and piston 420. Shown in FIG. 13K is a cross-sectional view through the piston assembly 400 shown in FIG. 13J along line K-K. Shown in FIG. 13L is a top view of the embodiment 400 of a piston assembly shown in FIG. 13J. Shown in FIG. 13M is a third cross-sectional view through the system 450 shown in FIG. 13F along line M-M. Shown in FIG. 13N is a detailed view of the detail N of the system 450 shown in FIG. 13M. Shown in FIG. 13P is a perspective view of the system 450 shown in FIG. 13F. Shown in FIG. 13R is a partially exploded view of the system 450 shown in FIG. 13P; an exploded view of the cartridge 10*f* is shown in FIG. 13A.

A function of the embodiment 400 of a piston assembly for a capillary adaptor 70 is to eject blood from the lumen 73 of the capillary adaptor 70. Details about the capillary adaptor 70 are provided in FIGS. 4F and 4H. Another function of the piston assembly 400 is to exert positive pressure on the blood in the blood storage conduit 52, to force blood into the optical chamber 57*f*, whereby the leading end of the blood in the optical chamber 57*f* that may be contaminated with atmospheric oxygen, is flushed out of the optical chamber 57*f*. Flushing out the optical chamber can also be accomplished during the process of engaging a cap with the cartridge inlet 43*f*, as already described.

Shown in FIG. 14A is a perspective view of a joint-diagnostic spectroscopic and biosensor system showing an embodiment of an analyzer, and an embodiment of a cartridge. For illustration, the interaction between the seventh embodiment 10*f* of a cartridge and an embodiment 310 of an analyzer is shown. Shown in FIG. 14B is a front view of the joint-diagnostic spectroscopic and biosensor system show in FIG. 14A, with the cartridge fully inserted into the slot 315 of the analyzer 310. Shown in FIG. 14C is a top view of the joint-diagnostic spectroscopic and biosensor system show in FIG. 14A, with the cartridge 10*f* fully inserted into the slot 315 of the analyzer 310. It should be noted that although the plane of insertion of the cartridge 10*f* into slot 315 of the analyzer 310 is parallel to the page, other analyzers with a plane of insertion of the cartridge in a slot perpendicular or at other angles to the page are also within the scope of the invention.

An example of a method for assessing a patient's oxygenation and acid-base status using the system described is now provided. The method comprises: 1) providing a disposable cartridge. The cartridge comprises: a) a cartridge inlet for receiving blood from one of a syringe containing the blood from the patient and a capillary adaptor for transferring portion of blood from a puncture site of a body part of the patient to the cartridge; b) a blood storage conduit having a proximal end and a distal end, wherein the proximal end is fluidly connected to the cartridge inlet; c) an optical chamber fluidly connected to the blood storage conduit at the distal end; d) a biosensor conduit comprising at least a pH biosensor to measure blood pH, the biosensor conduit being fluidly connected to the optical chamber; e) a calibration fluid pouch containing calibration fluid; and f) an air bladder.

The method further comprises: 2) providing a cap for sealing the cartridge inlet; and 3) providing an analyzer. The analyzer comprising: a) a slot; b) a source of EMR; c) a processor comprising at least two calibration algorithms for facilitating measurement of at least two hemoglobin species. The method further comprises: 3) filling the blood storage conduit and the optical chamber with blood from the patient; and, 4) sealing the cartridge inlet with the cap to provide a sealed cartridge, after filling. Sealing the cartridge inlet with the cap, and not when filling the blood storage conduit with blood, (as blood has typically already been added to the blood storage conduit), constitutes, in this embodiment, providing a pathway for pressurized air from the air bladder exit port to the proximal end of the blood storage conduit. When filling the blood storage conduit with blood and not when the cartridge inlet is sealed (typically before the cartridge inlet is sealed), the method further comprises blocking a portion of the blood storage conduit receiving the blood from the air bladder exit port to isolate the air bladder exit port from the blood.

The method further comprises: 5) inserting the sealed cartridge into the slot of the analyzer; 6) irradiating the blood in the optical chamber with the source of EMR and collecting spectroscopic data; 7) applying the at least two calibration algorithms to the spectroscopic data and obtaining concentrations of the at least two hemoglobin species; 8) calculating hemoglobin oxygen saturation from the concentrations of the at least two hemoglobin species; 9) calibrating the pH biosensor by at least releasing calibration fluid from the calibration fluid pouch and bringing the calibration fluid in contact with the pH biosensor; 10) activating the air bladder to provide a pressurized air flow through the pathway for the pressurized air to the proximal end of the blood storage conduit to bring some of the blood sample in contact with the pH biosensor, after the step of calibrating; and 11) measuring the blood pH, after the steps of irradiating the optical chamber and activating the air bladder, whereby the hemoglobin oxygen saturation and the blood pH provide an assessment of the patients oxygenation and acid-base status.

In another example of a method for assessing a patient's oxygenation and acid-base status, the cartridge inlet comprises a blood storage conduit entrance disposed inside the cartridge inlet at the proximal end of the blood storage conduit and an air bladder exit port fluidly connected to the air bladder. The method comprises blocking the portion of the blood storage conduit receiving the blood from the air bladder exit port to isolate the air bladder exit port from the blood. The method further comprises: 1) providing one of the syringe containing the blood and the capillary adaptor for transferring a portion of the blood from a puncture site of a body part of the patient to the cartridge; and 2) inserting the one of the syringe and the capillary adaptor inside the cartridge inlet before the step of filling, cutting off fluid communication between the storage conduit entrance and the air bladder exit port whereby blood flow into the air bladder during the step of filling the blood storage conduit and the optical chamber with blood from the patient, is mitigated.

In another example of a method for assessing a patient's oxygenation and acid-base status, the cartridge inlet is adapted to receive a capillary adaptor for transferring a portion of the blood from a puncture site of a body part of the patient to the cartridge. The capillary adaptor comprises: a) a capillary adaptor inlet member configured as a piece of a capillary tube, having a capillary adaptor inlet port for insertion into the blood sample; b) a capillary adaptor outlet member configured as the male end of a syringe; c) a capillary adaptor outlet port for substantially mating with the blood storage conduit entrance; d) a capillary adaptor lumen for fluidly connecting the capillary adaptor inlet port and the capillary adaptor outlet port; and e) a handgrip for handling the capillary adaptor. The method further comprises the step of: extending the blood storage conduit by the length of the capillary adaptor lumen by properly engaging the capillary adaptor lumen with the cartridge inlet.

In yet another example of a method for assessing a patient's oxygenation and acid-base status, the capillary adaptor further comprises: a) a piston assembly having a piston sized to slide into the capillary adaptor lumen; b) a head; and c) a rod for connecting the piston and the head. The method further comprises the step of: pushing the trapped blood out of the capillary adaptor lumen through the blood storage conduit entrance, with the piston assembly, whereby blood is conserved and the atmosphere-contaminated leading end of the blood sample is displaced from the optical chamber, allowing blood that is protected from atmospheric contamination to occupy the optical chamber.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

I claim:

1. A system for measurement of at least two hemoglobin species in a patient's blood sample by spectroscopy, and measurement of at least pH of the blood sample by biosensor, for assessing the patient's oxygenation and acid-base status, the system comprising:
   a disposable cartridge for processing a portion of the blood sample, the cartridge comprising a housing having:
      a cartridge inlet for engaging one of a syringe containing the blood sample and a capillary adaptor for transferring a portion of the blood sample from a puncture site of a body part of the patient to the cartridge;
      a blood storage conduit having a proximal end close to the cartridge inlet and a distal end away from the cartridge inlet;
      a blood storage conduit entrance at the proximal end of the blood storage conduit;
      an optical chamber for receiving the blood from the distal end of the blood storage conduit and for measuring the at least two hemoglobin species;
      an optical chamber overflow chamber fluidly connected with the optical chamber;
      at least one optical window, wherein at least a portion of the at least one optical window is in alignment with at least a portion of the optical chamber;
      a biosensor conduit for receiving the blood from the optical chamber overflow chamber, the biosensor conduit comprising at least a portion of a pH biosensor;
      an air bladder;
      an air bladder exit port, having an arrangement with the blood storage conduit entrance for providing pressurized air to the blood storage conduit via the blood storage conduit entrance, for urging the blood into the biosensor conduit;
      a waste receptacle for receiving liquid waste from the biosensor conduit; and
      a waste receptacle vent for relieving pressure in the waste receptacle;
   a cap for sealing the cartridge inlet; and,
   an analyzer comprising:
      an analyzer housing;
      a slot in the analyzer housing for receiving the disposable cartridge containing the blood sample;
      a source of electromagnetic radiation;
      at least one photodetector;
      a processor for controlling the analyzer; and
      at least two calibration algorithms installed on the processor for measuring the at least two hemoglobin species;
   wherein
   the system is adjustable between a sealed configuration and an unsealed configuration;
   in the sealed configuration, and not in the unsealed configuration, the system comprises a closed air passage connecting the air bladder exit port to the blood storage conduit entrance for communicating the pressurized air from the air bladder exit port to the blood storage conduit entrance; and,
   in the unsealed configuration, and not in the sealed configuration, the blood storage conduit entrance is configured to receive the blood.

2. The system according to claim 1, further comprising means for mitigating blood flow through the air bladder exit port when the blood storage conduit receives the blood, the means comprising:
one of the syringe and the capillary adaptor inserted in the cartridge inlet;
the blood storage conduit entrance, wherein the blood storage conduit entrance is disposed inside the cartridge inlet; and
the air bladder exit port arrangement with the blood storage conduit entrance is further arranged so that when the one of the syringe and the capillary adaptor is inserted in the cartridge inlet, fluid communication between the air bladder exit port and the blood storage conduit entrance is substantially cut off.

3. The system according to claim 1, wherein the cartridge inlet further comprises one of:
a cartridge inlet top having an annular surface; and
the annular surface comprising at least a portion of the air bladder exit port.
whereby when the cap is properly engaged with the cartridge inlet for sealing the cartridge inlet, the air bladder exit port maintains fluid connectivity with the blood storage conduit entrance.

4. The system according to claim 1, wherein the overflow chamber comprising at least one enlarged cavity for at least slowing down blood flow.

5. The system according to claim 1, wherein the blood storage conduit has a length dimension measured from the blood storage conduit entrance to the optical chamber and a cross-sectional area orthogonal to the length dimension, the size of the cross-sectional area being sufficiently small to receive the blood by capillary action.

6. The system according to claim 1, wherein the optical chamber comprises an optical chamber depth dimension orthogonal to a plane of insertion of the cartridge into the slot of the analyzer, wherein the optical chamber depth dimension is in an approximate range of about 50 microns to about 200 microns and wherein the optical chamber depth dimension is substantially uniform across the portion of the optical window and the portion of the optical chamber in alignment with each other.

7. The system according to claim 6, wherein the disposable cartridge further comprises a blood shunt in the housing for providing fluid connectivity between the distal end of the blood storage conduit and the optical chamber overflow chamber, the blood shunt having a maximum shunt depth dimension orthogonal to the plane of insertion of the cartridge into the slot of the analyzer, and wherein the maximum shunt depth dimension is substantially larger than the optical chamber depth dimension, whereby the blood shunt provides a more efficient blood flow from the distal end of the blood storage conduit to the biosensor conduit.

8. The system according to claim 1, wherein the blood storage conduit comprises a pre-fabricated heparinized capillary tube.

9. A disposable cartridge for operation with a joint spectroscopic and biosensor blood analyzer for measurement of at least two hemoglobin species in a patient's blood sample by spectroscopy, and measurement of at least pH of the blood sample by biosensor, for assessing the patient's oxygenation and acid-base status, the cartridge comprising a housing having at least a first housing member and a second housing member bonded together by a gasket, wherein the housing comprises:
a cartridge inlet;
a blood storage conduit within the housing having a proximal end close to the cartridge inlet and a distal end away from the cartridge inlet;
an optical chamber within the housing for receiving the blood from the distal end of the blood storage conduit and for measuring the at least two hemoglobin species, the optical chamber comprising an optical chamber depth dimension orthogonal to the gasket;
an optical chamber overflow chamber fluidly connected with the optical chamber;
a biosensor conduit within the housing for receiving the blood from the optical chamber overflow chamber, the biosensor conduit comprising a proximal end, a distal end and at least a portion of a pH biosensor;
a calibration fluid pouch nested in the housing and containing calibration fluid for at least calibrating the pH biosensor;
a calibration fluid conduit for transporting released calibration fluid to the biosensor conduit;
a waste receptacle for receiving liquid waste from the biosensor conduit;
a vent for relieving pressure in the waste receptacle;
an air bladder and an air bladder exit port within the housing for providing pressurized air for urging blood from the blood storage conduit into the biosensor conduit; and
a blood shunt for providing fluid connectivity between the distal end of the blood storage conduit and the optical chamber overflow chamber, the blood shunt having a maximum shunt depth dimension orthogonal to the gasket, and wherein the maximum shunt depth dimension is substantially larger than the optical chamber depth dimension, whereby the blood shunt provides a more efficient blood flow from the distal end of the blood storage conduit to the biosensor conduit;

the first housing member comprises:
one of a first optical window and a first reflecting member;
the second housing member comprises:
one of a second optical window and a second reflecting member, positioned to align with at least a portion of the optical chamber and at least a portion of the one of a first optical window and a first reflecting member;
the gasket having a plurality of cut-outs comprising at least:
a first gasket cut-out positioned to provide fluid connection between the blood storage conduit and the optical chamber, wherein at least a portion of the first gasket cut-out is positioned to align with at least a portion of the optical chamber for collecting spectroscopic data from blood in that portion of the optical chamber;
a second gasket cut-out positioned to provide fluid connection between the calibration fluid conduit and the biosensor conduit, the second gasket cut-out disposed around the proximal end of the biosensor conduit;
a third gasket cut-out positioned to at least align with the active area of the pH biosensor; and
a fourth gasket cut-out positioned to provide fluid connection between the distal end of the biosensor conduit and the waste receptacle.

10. The disposable cartridge according to claim 9, wherein the depth dimension of the optical chamber is substantially uniform across the at least one optical window in an approximate range of about 50 microns to about 200 microns.

11. The disposable cartridge according to claim 9, wherein the thickness of the gasket is in the approximate range of about 50 microns to 200 microns.

12. A disposable cartridge adapted for insertion along an insertion plane into the slot of a joint spectroscopic and biosensor analyzer for measurement of at least two hemoglobin species in a patient's blood sample by spectroscopy, and measurement of at least pH of the blood sample by biosensor, for assessing the patient's oxygenation and acid-base status, the cartridge comprising:
- a housing;
- a cartridge inlet in the housing for receiving the blood sample;
- a blood storage conduit within the housing having a proximal end close to the cartridge inlet and a distal end away from the cartridge inlet;
- an optical chamber within the housing for receiving the blood from the distal end of the blood storage conduit and for measuring the at least two hemoglobin species, the optical chamber comprising an optical depth dimension orthogonal to the insertion plane;
- at least one optical window in the housing positioned to align with at least a portion of the optical chamber for collecting spectroscopic data from blood in that portion of the optical chamber;
- an optical chamber overflow chamber in fluid connection with the optical chamber for receiving blood from the optical chamber;
- a biosensor conduit within the housing for receiving the blood from the optical chamber overflow chamber, the biosensor conduit having at least one biosensor for measuring the at least pH of the blood sample;
- a blood shunt for providing fluid connectivity between the distal end of the blood storage conduit and the optical chamber overflow chamber, the blood shunt having a maximum shunt depth dimension orthogonal to the insertion plane, and wherein the maximum shunt depth dimension is substantially larger than the optical chamber depth dimension, for a more efficient blood flow from the distal end of the blood storage conduit to the biosensor conduit;
- an air bladder and an air bladder exit port within the housing for providing pressurized air for urging blood from the blood storage conduit into the biosensor conduit;
- a waste receptacle for receiving waste liquid from the biosensor conduit; and
- a waste receptacle vent for relieving pressure in the waste receptacle.

13. The disposable cartridge according to claim 12, wherein the blood shunt further comprises a slit adjacent to the optical chamber, the slit having a length not greater than the length of the blood shunt and a slit width approximately equal to the optical depth, whereby since the optical chamber is vented via the waste receptacle vent, the slit facilitates flow of blood into the optical chamber.

14. The disposable cartridge according to claim 12, wherein the blood storage conduit begins at a the blood storage conduit entrance and terminates at the optical chamber, and the volume of the blood storage conduit is in an approximate range of about 50 microliters to about 100 microliters.

15. The disposable cartridge according to claim 12, wherein the optical depth is in an approximate range of about 50 microns to about 200 microns.

16. The disposable cartridge according to claim 12, wherein a portion of the optical chamber that is aligned with the at least one optical window has an area in an approximate range of about 1 sq. millimeter to about 100 sq. millimeters.

17. The disposable cartridge according to claim 12, wherein the biosensor conduit further comprises an oxygen biosensor for measuring $pO_2$ in the blood sample and a plurality of blind holes disposed approximately above the oxygen biosensor and disposed at the roof of the biosensor conduit, the blind holes of sufficient size and number for trapping sufficient air for equilibrating the calibration fluid with atmospheric oxygen, in order to assign a $pO_2$ to the calibration fluid used to calibrate the oxygen biosensor.

18. The disposable cartridge according to claim 12, further comprising a calibration fluid pouch nested in a calibration fluid pouch nest, the calibration fluid pouch comprises:
- a bulging side comprising a first foil outer layer and a first polymer inner layer;
- a flat side comprising a second foil outer layer and a second polymer inner layer;
- a flange comprising a perimeter seal for holding the bulging side and the flat side together; and
- a cavity between the bulging side and the flat side containing calibration fluid for at least calibrating the pH biosensor, wherein the first polymer inner layer is of sufficient thickness to allow formation of a bulge in the bulging side, and wherein the second polymer inner layer is of sufficient thickness to allow bonding of the first and second polymer inner layers along the flange, but sufficiently thin for easy piercing to release the calibration fluid; and, the calibration fluid pouch nest comprises:
- a calibration fluid pouch nest having a recess disposed around the middle;
- the flat side of the pouch nesting in the calibration fluid pouch nest; and
- a spike having a tip disposed in the recess for piercing the pouch, wherein the tip of the spike is sufficiently below the flat portion of the pouch nest, to prevent accidental premature pouch rupture.

19. A method for assessing a patient's oxygenation and acid-base status, the method comprising:
providing a disposable cartridge comprising:
- a cartridge inlet for receiving blood from one of a syringe containing the blood from the patient and a capillary adaptor for transferring a portion of blood from a puncture site of a body part of the patient to the cartridge;
- a blood storage conduit having a proximal end and a distal end, wherein the proximal end is fluidly connected to the cartridge inlet;
- an optical chamber fluidly connected to the blood storage conduit at the distal end;
- a biosensor conduit comprising at least a pH biosensor to measure blood pH, the biosensor conduit being fluidly connected to the blood storage conduit;
- a calibration fluid pouch containing calibration fluid; and
- an air bladder having an air bladder exit port;

providing a cap for sealing the cartridge inlet;
providing an analyzer comprising:
  a slot;
  a source of electromagnetic radiation; and
  a processor comprising at least two calibration algorithms for facilitating measurement of at least two hemoglobin species;
filling the blood storage conduit and the optical chamber with blood from the patient;
sealing the cartridge inlet with the cap to provide a sealed cartridge, after filling;
when the cartridge inlet is sealed and not when filling the blood storage conduit with blood, providing a pathway for pressurized air from the air bladder exit port to the proximal end of the blood storage conduit;
when filling the blood storage conduit with blood and not when the cartridge inlet is sealed, substantially blocking a portion of the blood storage conduit receiving the blood from the air bladder exit port to substantially isolate the air bladder exit port from the blood;
inserting the sealed cartridge into the slot of the analyzer;
irradiating the blood in the optical chamber with the source of electromagnetic radiation and collecting spectroscopic data;
applying the at least two calibration algorithms to the spectroscopic data and obtaining concentrations of the at least two hemoglobin species;
calculating hemoglobin oxygen saturation from the concentrations of the at least two hemoglobin species;
calibrating the pH biosensor by at least releasing calibration fluid from the calibration fluid pouch and bringing the calibration fluid in contact with the pH biosensor, after the step of inserting the sealed cartridge;
activating the air bladder to provide a pressurized air flow through the pathway for the pressurized air to the proximal end of the blood storage conduit to bring some of the blood sample in contact with the pH biosensor, after the step of calibrating; and
measuring the blood pH, after the steps of irradiating the optical chamber and activating the air bladder,
whereby the hemoglobin oxygen saturation and the blood pH provide an assessment of the patients oxygenation and acid-base status.

20. The method for assessing a patient's oxygenation and acid-base status of claim 19, wherein the cartridge inlet comprises a blood storage conduit entrance disposed inside the cartridge inlet at the proximal end of the blood storage conduit and an air bladder exit port fluidly connected to the air bladder, and the blocking the portion of the blood storage conduit receiving the blood from the air bladder exit port to isolate the air bladder exit port from the blood comprises:
  providing one of the syringe containing the blood and the capillary adaptor for transferring a portion of the blood from a puncture site of a body part of the patient to the cartridge; and
  inserting the one of the syringe and the capillary adaptor inside the cartridge inlet before the step of filling, substantially cutting off fluid communication between the blood storage conduit and the air bladder exit port,
whereby blood flow into the air bladder during the step of filling the blood storage conduit and the optical chamber with blood from the patient, is mitigated.

21. The method for assessing a patient's oxygenation and acid-base status of claim 19, wherein the cartridge inlet is adapted to receive a capillary adaptor for transferring a portion of the blood from a puncture site of a body part of the patient to the cartridge, and wherein the capillary adaptor comprises:
  a capillary adaptor inlet member configured as a piece of a capillary tube, having a capillary adaptor inlet port for insertion into the blood sample;
  a capillary adaptor outlet port for substantially mating with the proximal end of the blood storage conduit;
  a capillary adaptor lumen for fluidly connecting the capillary adaptor inlet port and the capillary adaptor outlet port; and
  a handgrip for handling the capillary adaptor,
and the method further comprises:
  extending the blood storage conduit by the length of the capillary adaptor lumen by properly engaging the capillary adaptor lumen with the cartridge inlet.

* * * * *